(12) United States Patent
Zahradka

(10) Patent No.: US 6,544,541 B1
(45) Date of Patent: Apr. 8, 2003

(54) DEVICES AND COMPOUNDS FOR TREATING ARTERIAL RESTENOSIS

(75) Inventor: Peter Zahradka, Winnipeg (CA)

(73) Assignee: Cardiovascular Solutions, Inc., Winnipeg (CA)

( * ) Notice: Subject to any disclaimer, the term of this patent is extended or adjusted under 35 U.S.C. 154(b) by 0 days.

(21) Appl. No.: 09/585,886

(22) Filed: May 31, 2000

Related U.S. Application Data

(60) Provisional application No. 60/150,696, filed on Jun. 2, 1999.

(51) Int. Cl.[7] ............................. A61F 13/00; A61F 2/00
(52) U.S. Cl. ..................... 424/422; 424/423; 424/424; 424/425
(58) Field of Search .................. 424/422, 423, 424/424, 425

(56) References Cited

U.S. PATENT DOCUMENTS

| | | |
|---|---|---|
| 3,427,931 A | 2/1969 | Wainberg |
| 3,527,864 A | 9/1970 | MacMillan et al. |
| 3,896,238 A | 7/1975 | Smith |
| 3,903,256 A | 9/1975 | MacMillan et al. |
| 3,952,099 A | 4/1976 | Smith |
| 4,046,886 A | 9/1977 | Smith |
| 4,130,643 A | 12/1978 | Smith |
| 4,130,667 A | 12/1978 | Smith |
| 4,299,826 A | 11/1981 | Luedders |
| 4,335,115 A | 6/1982 | Thompson et al. |
| 4,343,798 A | 8/1982 | Fawzi |
| 4,379,454 A | 4/1983 | Campbell et al. |
| 4,405,616 A | 9/1983 | Rajadhyaksha |
| 4,746,515 A | 5/1988 | Cheng et al. |
| 4,788,062 A | 11/1988 | Gale et al. |
| 4,820,720 A | 4/1989 | Sanders et al. |
| 4,863,738 A | 9/1989 | Taskovich |
| 4,863,970 A | 9/1989 | Patel et al. |
| 5,378,730 A | 1/1995 | Lee et al. |
| 5,455,039 A | 10/1995 | Edelman et al. |
| 5,527,532 A | 6/1996 | Edelman et al. |
| 5,574,059 A | 11/1996 | Regunathan et al. |
| 5,591,227 A * | 1/1997 | Dinh et al. ............... 623/1 |
| 5,792,769 A | 8/1998 | Lu et al. |
| 5,861,168 A * | 1/1999 | Cooke et al. ............ 424/424 |

FOREIGN PATENT DOCUMENTS

| | | |
|---|---|---|
| GB | 1011949 | 10/1964 |
| WO | WO 98/23565 A3 * | 6/1998 |
| WO | WO 98/23565 A2 * | 6/1998 |
| WO | WO 99/09912 A1 | 3/1999 |

OTHER PUBLICATIONS

Thyberg et al. Inhibitors of ADP–ribosylation suppress phenotypic modulation and proliferation of smooth muscle cell cultered from rat aorta. Differentiation (1995) 59:243–252.*

Taguchi et al. L–arginine inhibits neointimal formation following balloon injury. Life Science 1993; 53 (23): PL387–392. (abstract).*

Akle, C.A. et al. (1997). "nIBG Diagnosis and Therapy in Smooth Muscle Tumors of the Small Bowel," *Eur. J. Nucl. Med.* 24(9):1196.

(List continued on next page.)

*Primary Examiner*—Thurman K. Page
*Assistant Examiner*—Rachel M. Bennett
(74) *Attorney, Agent, or Firm*—Morrison & Foerster LLP

(57) ABSTRACT

Described herein is the use of ADPRT decoy substrates to treat or prevent proliferative disorders. In one example, MIBG is shown to prevent restenosis in damaged vessels. In one embodiment, MIBG is combined with an adhesive agent for localizing the mixture to the site of injury. As a result of this arrangement, MIBG is not systemically released.

6 Claims, 34 Drawing Sheets

OTHER PUBLICATIONS

Alhonen–Hongisto, L. et al. (1980). "Inhibition by Derivatives of Diguanidines of Cell Proliferation in Ehrlich Ascites Cells Grown in Culture," *Biochem. J.* 188:491–501.

Autieri, M.V. et al. (1995). "Antisense Oligonucleotides to the P65 Subunit of NF–kB Inhibit Human Vascular Smooth Muscle Cell Adherence and Proliferation and Prevent Neointima Formation in Rat Carotid Arteries," *Biochem. Biophys. Res. Commun.* 213:827–836.

Babich, J.W. et al. (1997). "Effect of Adrenergic Receptor Ligands on Metaiodobenylguanidine Uptake and Storage in Neuroblastoma Cells," *Eur. J. Nucl. Med.* 24:538–543.

Banasik, M. et al. (Jan. 25, 1992). "Specific Inhibitors of Poly(ADP–Ribose) Synthetase and Mono(ADP–Ribosyl)transferase," *J. Biol. Chem.* 267:1569–1575.

Bauriedel, G. et al. (Feb. 1992). "Migratory Activity of Human Smooth Muscle Cells Cultivated from Coronary and Peripheral Primary and Restenotic Lesions Removed by Percutaneous Atherectomy," *Circulation* 85(2):554–564.

Bousquet, P. (1997). "Imidazoline Receptors," *Neurochem. Int.* 30(1):3–7.

Braun–Dallaeus, R.C. et al. (Jul. 7, 1998). "Cell Cycle Progression. New Therapeutic Target for Vascular Proliferative Disease," *Circulation* 98(1):82–89.

Burzio, V.A. et al. (1996). "Mussel Adhesive Enhances the Immobilization of Human Chorionic Gonadotrophin to a Solid Support," *Anal. Biochem.* 241:190–4.

Casscells, W. (Sep. 1992). "Migration of Smooth Muscle and Endothelial Cells," *Circulation* 86(3):723–729.

Chen, T.K. et al. (1996). "Activation and Inibition of the AP–1 Complex in Human Breast Cancer Cells," *Mol. Carcinog.* 15:215–226.

Child, S.J. et al. (1993). "Further Characterization of an Adenosine–Containing Modification of Vaccina Virus Proteins," *Biochim. Biophys. Acta* 1157:217–228.

Cornelissen, J. et al. (1995). "Meta–Iodobenylguanidine Inhibits Complex I and III of the Respiratory Chain in the Human Cell Line MOLT–4," *Biochem. Pharmacol.* 49:471–477.

Dagani, R. (Jun. 9, 1997). "Intelligent Gels," *Chemical & Engineering News* 26–37.

de Murcia, G. et al. (May 25, 1986). "Modulation of Chromatin Superstructure Induced by Poly(ADP–ribose) Synthesis and Degradation," *J. Biol. Chem.* 261(15):7011–7017.

Duriez, P.J. et al. (1997). "Cleavage of Poly(ADP–Ribose) Polymerase: A Sensitive Parameter to Study Cell Death," *Biochem. Cell Biol.* 75:337–349.

Fasol, R. et al. (Jun. 1994). "Experimental Use of a Modified Fibrin Glue to Induce Site–Directed Angiogenesis from the Aorta to the Heart," *J. Thorac. Cardiovasc. Surg.* 107(6):1432–1439.

Freed, M. et al. (Dec. 1, 1995). "Combination of Lovastatin, Enalapril, and Colchicine Does Not Prevent Restenosis after Percutaneous Transluminal Coronary Angioplasty," *Am. J. Cardiol.* 76:1185–1188.

Furukawa, Y. et al. (Feb. 19, 1999). "Anti–Monocyte Chemoattractant Protein–1/Monocyte Chemotactic and Activating Factor Antibody Inhibits Neointimal Hyperplasia in Injured Rat Carotid Arteries," *Circ. Res.* 84(3):306–314.

Gasnier, B. et al. (1986). "Uptake of Meta–Iodobenyguanidine by Bovine Chromaffin Granule Membranes," *Mol. Pharmacol.* 29:275–280.

Geary, R.L. et al. (Jun. 15, 1995). "Failure of Heparin to Inhibit Intimal Hyperplasia in Injured Baboon Arteries," *Circulation* 91(12):2972–2981.

George, S.J. et al. (Apr. 10, 1998) "Adenovirus–Mediated Gene Transfer of the Human TIMP–1 Gene Inhibits Smooth Muscle Cell Migration and Neointimal Formation in Human Saphenous Vein," *Hum. Gene Ther.* 9:867–877.

Giasson, E. et al. (Oct. 24, 1997). "Cyclic AMP–Mediated Inhibition of Angiotensin II–Induced Protein Synthesis Is Associated with Suppression of Tyrosine Phosphorylation Signaling in Vascular Smooth Muscle Tissue," *J. Biol. Chem.* 272(43):26879–26886.

Gradus–Pizlo, I. (Nov. 15, 1995). "Local Delivery of Biodegradable Microparticles Containing Colchine or a Cholchine Analogue: Effects on Restenosis and Implications for Catheter–Based Drug Delivery," *J. Am. Coll. Cardiol.* 26(6):1549–1557.

Greco, F. et al. (1991). "Fibrin–Antibiotic Mixtures: An In Vitro Study Assessing the Possibility of Using a Biologic Carrier for Local Drug Delivery," *J. Biomed. Mater. Res.* 25: 39–51.

Gu, W. et al. (1993). "Interaction of Myogenic Factors and the Retinoblastoma Protein Mediates Muscle Cell Commitment and Differentiation," *Cell* 72:309–324.

Hadrich, D. et al. (1999). "Synthesis and Characterization of Fluorescent Ligands for the Norepinephrine Transporter: Potential Neuroblastoma Imaging Agents," *J. Med. Chem.* 42:3101–3108.

Halldorsson, H. et al. (Dec. 1992). "Role of ADP–Ribosylation in Endothelial Signal Transduction and Prostacyclin Production," *FEBS Lett.* 314(3):322–326.

Hauschildt, S. et al. (1998). "ADP–Ribosylation: Role in LPS–Induced Phosphorylation of Two Cytosolic Proteins (p36/38 in Monocytes)," in *Endotoxin and Sepsis: Molecular Mechanisms of Pathogenesis Host Resistance, and Therapy*, J. Levin et al. ed., John Wiley & Sons, Inc., Publication: New York, 397:147–155. (Proceedings of the 4th Conference of the Internation Endotoxin Society, Nagoya, Japan, held Oct. 23–27, 1996).

Hoefnagel, C.A. et al. (1987). "The Role of I–131–MIBG in the Diagnosis and Therapy of Cacinoids," *Eur. J. Nucl. Med.* 13:187–191.

Idson, B. (Jun. 1975). "Percutaneous Absorption," *J. Pharm. Sci.* 64(6):901–924.

Inageda, K. et al. (May 15, 1991). "Mono–ADP–Ribosylation of Gs by an Eukaryotic Arginine–Specific ADP–Ribosyltransferase Stimulates the Adenylate Cyclase System," *Biochem. Biophys. Res. Commun.* 176(3):1014–1019.

Jonsson, O. et al. (1998). "Inhibitory Effects of Meta–Iodo–Benzylguanidine (MIBG) on Endothelial Histamine Receptor Binding," *Biochim. Biophys. Acta* 1379:143–150.

Juedes, M.J. et al. (Nov. 1992). "m–Iodobenylguanidine Increases the Mitochondrial Ca2+ Pool in Isolated Hepatocytes," *FEBS Lett.* 313(1):39–42.

Kanoh, H. et al. (Feb. 28, 1997). "Arfaptin 1, a Putative Cytosolic Target Protein of ADP–Ribosylation Factor, Is Recruited to Golgi Membranes," *J. Biol. Chem.* 272(9):5421–5429.

Katz, J. et al. (Apr. 1998). "Biomaterial Research Focuses on Developing New Applications," *Medical Device and Diagnostic Industry Magazine* 40–47.

Kharadia, S.V. et al. (1992). "Effect of an Arginine–Specific ADP–Ribosyltransferase Inhibitor on Differentiation of Embyronic Chick Skeletal Muscle Cells in Culture," *Exp. Cell Res.* 201: 33–42.

Knight III, W.A.T. et al. (1983). "Methyl–Glyoxal Bis Guanyl Hydrazone (Methyl–GAG, MGBG) in Lymphoma and Hodgkins' Disease," *Invest. New Drugs* 1:235–237.

Kornowski, R. et al. (Jan. 1998). "In–Stent Restenosis: Contributions of Inflammatory Responses and Arterial Injury to Neointimal Hyperplasia," *J. Am. Coll. Cardiol.* 31(1):224–230.

Kuin, A. et al. (1998). "Renal Toxicity of the Neuron–Blocking and Mitochondriotropic Agent m–Iodobenzylguanidine," *Cancer Chemother. Pharmacol.* 42:37–45.

Kuin, A. et al. (1999). "Potentiation of Anti–Cancer Drug Activity at Low Intratumoral pH Induced by the Mitochrondrial Inhibitor m–Iodobenzylguanidine (MIBG) and Its Analogue Benzylguanidine (BG)," *Brit. J. Cancer* 79(5/6):793–801.

Lassar, A.B. et al. (1989). "Transformation by Activated Ras or Fos Prevents Myogenesis by Inhibiting Expression of MyoD1," *Cell* 58:659–667.

Le Feuvre, C. et al. (1998). "Arterial Response to Mild Balloon Injury in the Normal Rabbit: Evidence for Low Proliferation Rate in the Adventitia," *Cor. Artery. Dis.* 9:805–814.

Lehtinen, S.K. et al. (1996). "Down–Regulation of Transcription Factors Ap–1, SP–1, and NF–kB Preceeds Myocyte Differentiation," *Biochem Biophys Res Comm.* 229:36–43.

Libby, P. et al. (Dec. 1992). "A Cascade Model for Restenosis. A Special Case of Atherosclerosis Progression," *Circulation* 86(6):111–47–111–52.

Lindahl, T. et al. (1995). "Enzymes Acting at Strand Interruptions in DNA," *Phil. Trans. R. Soc. Lond. B.* 347:57–62.

Lindahl, T. et al. (Oct. 1995). "Post–Translational Modification of Poly(ADP–Ribose) Polymerase Induced by DNA Strand Breaks," *TIBS* 20:405–411.

Lindner, V. (1998). "The NF–IkB and IkB System in Injured Arteries," *Pathobiology* 66:311–320.

Loesberg, C. et al. (1990). "Meta–Iodobenzyguanidine (MIBG), a Novel High–Affinity Substrate for Cholera Toxin that Interferes with Cellular Mono(ADP–Ribosylation)," *Biochim. et Biophys. Acta* 1037:92–99.

Loesberg, C. et al. (1991). "Mitochondrial Effects of the Guanidino Group–Containing Cytostatic Drugs, m–Iodobenzylguanidine and Methylglyoxal Bis (Guanylhydrazone)," *Biochem. Paramacol.* 42:793–798.

Maehama, T. et al. (1994). "Characterization of Botulinum C3–Catalyzed ADP–Ribosylation of Rho Proteins and Identification of Mammalian C3–Like ADP–Ribosyltransferase," *Mol. Cell. Biochem.* 138:135–140.

Mallat, A. et al. (Oct. 16, 1998). "Platelet–Derived Growth Factor–BB and Thrombin Generate Positive and Negative Signals for Human Hepatic Stellate Cell Proliferation," *J. Biol. Chem.* 273:27300–27305.

Mandel, J.–L. (1978). "Isolation of Mutant Mammalian Cells Altered in Polyamine Transport," *J. Cell Physiol.* 97:335–344.

Mihich, E. (1975). "Bis–Guanylhydrazones" Chapter 71 in *Handbook of Experimental Pharmacology*. O. Eichler, Heidelberg Ed., Springer: Berlin. pp. 766–788.

Morgan, D. (Apr. 30, 1990). "Primer Offered for Scientists Bringing Drugs to Market," *The Scientist* 4:7,13.

Moss, J., Ed. (1994). *ADP–Ribosylation: Metabolic Effects and Regulatory Functions*. Boston: Kluwer Academic Publishers. (Table of Contents).

Negoro, N. et al. (1999). "The Kinase Inhibitor Fasudil (HA–1077) Reduces Intimal Hyperplasia Through Inhibiting Miagration and Enhancing Cell Loss of Vascular Smooth Cells," *Biochem. Biophys. Res. Comm.* 262:211–215.

O'Brien, E.R. et al. (1993). "Proliferation in Primary and Restenotic Coronary Atherectomy Tissue," *Circ. Res.* 73:223–231.

Okazaki, I.J. et al. (Sep. 11, 1998). "Glycosylphosphatdylinositol–Anchored Secretory Isoforms of Mono–ADP–Ribosyltransferase," *J. Biol. Chem.* 273(37):23617–23620.

Oppenheimer, N.J. (1984). "ADP–Ribosylarginine," *Methods in Enzymology* 106:399–403.

Pappas, P.J. et al. (1998). "Retinoblastoma Protein: A Molecular Regulator of Chronic Venous Insufficiency," *J. Surg. Res.* 76:149–153.

Pellat–Deceuynck, C. et al. (1994). "Nicotinamide Inhibits Nitric Oxide Synthase mRNA Induction in Activated Macrophages," *Biochem. J.* 297:53–58.

Pitman, M.I. et al. (1989). "The Use of Adhesives in Chondrocyte Transplantation Surgery: In Vivo Studies," *Bull. Hosp. Jt. Dis. Orthop. Inst.* 49(2):213–20.

Rahm, M. et al. (1989). "Elevated c–Fos Expression Inhibits Differentiation of L6 Rat Myoblasts," *J. Cell. Physiol.* 139:237–244.

Rankin, P.W. et al. (Mar. 15, 1989) "Quantitative Studies of Inhibitors of ADP–Ribosylation In Vitro and In Vivo," *J. Biol. Chem.* 264(8):4312–4317.

Regunathan, S. et al. (1996). "Imidazoline Receptors and Their Endogenous Ligands," *Annu. Rev. Pharmacol. Toxicol.* 36:511–544.

Regunathan, S. et al. (1997) "Stimulation of Imidazoline Receptors Inhibits Proliferation of Human Coronary Artery Vascular Smooth Muscle Cells," *Hypertension* 30:295–300.

Regunathan, S. et al. (1996). "Imidazoline Receptors and Agmatine in Blood Vessels: A Novel System Inhibiting Vascular Smooth Muscle Proliferation," *J. Pharmacol. Expt. Ther.* 276(3):1272–1282.

Reidy, M.A. (1985). "Biology of Disease. A Reassessment of Endothelial Injury and Arterial Lesion Formation," *Lab. Invest.* 53(5):513–520.

Sarkar, R. et al. (1997). "Cell Cycle Effects of Nitric Oxide on Vascular Smooth Muscle Cells," *Am. J. Physiol.* 272:H1810–H1818.

Saward, L. et al. (1996). "The Angiotensin Type 2 Receptor Mediates RNA Synthesis in A10 Vascular Smooth Muscle Cells," *J. Mol. Cell. Cardiol.* 28:499–506.

Saward, L et al. (Aug. 1997). "Angiotensin II Activates Phosphatidylinositol 3–Kinase in Vascular Smooth Muscle Cells," *Circ. Res.* 81:249–257.

Saward, L. et al. (1997). "Coronary Artery Muscle in Culture: Migration of Heterogeneous Cell Populations from Vessel Wall," *Mol. Cell. Biochem.* 176:53–59.

Schwartz, S.M. et al. (Sep. 1995). "The Intima: Soil for Atherosclerosis and Restenosis," *Circ. Res.* 77(3):445–465.

Schwartz, S.M. (Jun. 15, 1997). "Smooth Muscle Migration in Atherosclerosis and Restenosis," *J. Clin. Invest.* 99(12):2814–2817.

Senderoff, R.I. et al. (Jan.–Feb. 1991). "Fibrin Based Drug Delivery Systems," *J. Parenteral. Sci. Technol.* 45(1):2–6.

Serruys, P.W. et al. (Apr. 4, 2000). "Carvedilol for Prevention of Restenosis After Directional Coronary Atherectomy," *Circulation* 101(13):1512–1518.

Shainkin–Kestenbaum, R. et al. (1987). "Effect of Guanidino–Propionic Acid on Lymphocyte Proliferation," *Nephron* 44:295–298.

Shapiro, B. et al. (1995). "The Current Status of Radioiodinated Metaiodobenzylguanidine Therapy of Neuro–Endocrine Tumors," *Q. J. Nucl. Med.* 39:55–57.

Short, J.H. et al. (Sep. 1967). "Sympathetic Nervous System Blocking Agents. III. Derivatives of Benzyguanidine," *J. Med. Chem.* 10(5):833–840.

Short, J.H. et al. (May 1963). "Sympathetic Nervous System Blocking Agents. Derivatives of Guanidine and Related Compounds," *J. Med. Chem.* 6(3):275–283.

Simon, A.D. et al. (1999). "Porous Balloon Delivery of S–dC28 Does Not Prevent Restenosis in the Porcine Coronary Artery Model of Balloon Injury," *Antisense Nucl. Acid Drug Dev.* 9:549–553.

Smets, L.A. et al. (1988). "Cytotoxic and Antitumor Effects of the Norepinephrine Analogue Meta–Iodo–Benzylguanidine (MIBG)," *Cancer Chemother. Pharmacol.* 21:9–13.

Smets, L.A. et al. (1990). "Extragranular Storage of the Neuron Blocking Agent Meta–Iodobenzylguanidine (MIBG) in Human Neuroblastoma Cells," *Biochem. Pharmacol.* 39:1959–1964.

Smets, L.A. et al. (1990). "Intracellular Inhibition of Mono(ADP–Ribosylation) by Meta–Iodobenzylguanidine: Specificity, Intracellular Concentration and Effects on Glucocorticoid–Mediated Cell Lysis," *Biochim. Biophys. Acta* 1054:49–55.

Soman, G. et al. (1983). "Assay of Mono ADP–Ribosyltransferase Activity by Using Guanylhydrazones," *Anal. Biochem.* 134:101–110.

Soman, G. et al. (1986). "Use of Substituted (Benzylidineamino)guanidines in the Study of Guanidino Group Specific ADP–Ribosyltransferase," *Biochemistry* 25:4113–4119.

Somsen, G.A. et al. (1996). "Neuronal Dysfunction in Heart Failure Assessed by Cardiac 123–Iodine Metaiodobenzylguanidine Scintigraphy," *Int. J. Card. Imaging* 12:305–310.

Taal, B.G. et al. (1996). "Palliative Effect of Metaiodobenzylguanidine in Metastatic Carcinoid Tumors," *J. Clin. Oncol.* 14:1829–1838.

Tamaki, N. et al. (1997). "Recent Advances in Nuclear Cardiology in the Study of Coronary Artery Disease," *Ann. Nucl. Med.* 11(2):55–66.

Tanuma, S. et al. (1988). "Eukaryotic Mono(ADP–Ribosyl)transferase that ADP–Ribosylates GTP–Binding Regulatory Gi Protein," *J. Biol. Chem.* 263:5485–5489.

Thyberg, J. et al. (1995). "Inhibitors of ADP–Ribosylation Suppress Phenotypic Modulation and Proliferation of Smooth Muscle Cells Cultured from Rat Aorta," *Differentiation* 59:243–252.

Trucco, C. et al. (1998). "DNA Repair Defect in Poly(ADP–Ribose) Polymerase –Deficient Cell Lines," *Nucl. Acids Res.* 26:2644–2649.

Walsh, K. et al. (1996). "Molecular Strategies to Inhibit Restenosis: Modulation of the Vascular Myocyte Phenotype," *Semin. Intervent. Cardiol.* 1:173–179.

Wei, L. et al. (1998). RhoA Signaling via Serum Response Factor Plays an Obligatory Role in Myogenic Differentiation, *J. Biol. Chem.* 273:30287–30294.

Wieland, D.M. et al. (1980). "Radiolabeled Adrenergic Neuron–Blocking Agents: Adrenomedullary Imaging with [$^{131}$I]Iodobenzylguanidine," *J. Nucl. Med.* 21(4):349–353.

Wieland, D.M. et al. (1981). "Myocardial Imaging with a Radioiodinated Norepinephrine Storage Analog," *J. Nucl. Med.* 22(1):22–31.

Wilson, D.P. et al. (1999). "Angiotensin II Receptor Antagonists Prevent Neointimal Proliferation in a Porcine Coronary Artery Organ Culture Model," *Cardiac. Res.* 42:761–772.

Yau, L. et al. (1997). "Immunodetection of Activated Mitogen–Activated Protein Kinase in Vascular Tissues," *Mol. Cell. Biochem.* 172:59–66.

Yau, L. et al. (1998). "Repression of Phosphoenolpyruvate Carboxykinase Gene Activity by Insulin Is Blocked by 3–Aminobenzmide but Not by PD 128763, a Selective Inhibitor of Poly (ADP–Ribose) Polymerase," *Eur. J. Biochem.* 253:91–100.

Yokozawa, T. et al. (1989). "Comparison of Toxic Effects of Methyguanidine, Guanidinosuccinic Acid and Creatinine in Rats with Adenine–Induced Chronic Renal Failure," *Nephron* 51:388–392.

Zahradka, P. et al. (1982). "A Shuttle Mechanism for DNA–Protein Interactions. The Regulation of Poly(ADP–Ribose) Polymerase," *Eur. J. Biochem.* 127:579–585.

Zahradka, P. et al. (1994). "ADP–Ribosylation and Gene Expression." *Mol. Cell. Biol.* 138:91–98.

Zarge, J.I. et al. (1997). "Fibrin Glue Containing Fibroblast Growth Factor Type 1 and Heparin with Autologous Endothelial Cells Reduces Intimal Hyperplasia in a Canine Carotid Artery Balloon Injury Model," *J. Vasc. Surg.* 25:840–849.

Zilch, H. et al. (1986). "The Sustained Release of Cefotaxim from a Fibrin–Cefotaxim Compounds in Treatment of Osteitis," *Arch. Orthop. Trauma Surg.* 106:36–41.

* cited by examiner

FIGURE 4
A 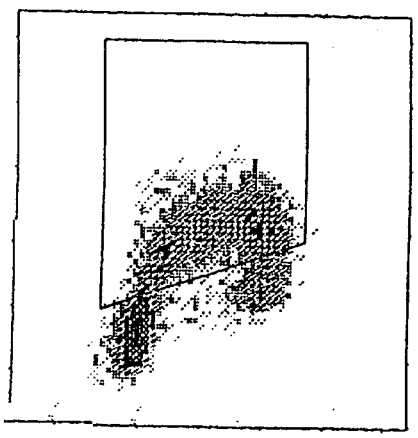  B 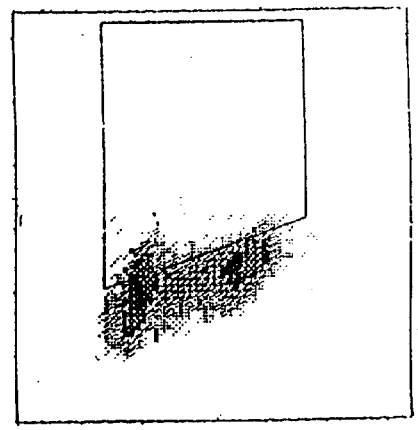
Propidium Iodide   Propidium Iodide

FIGURE 5
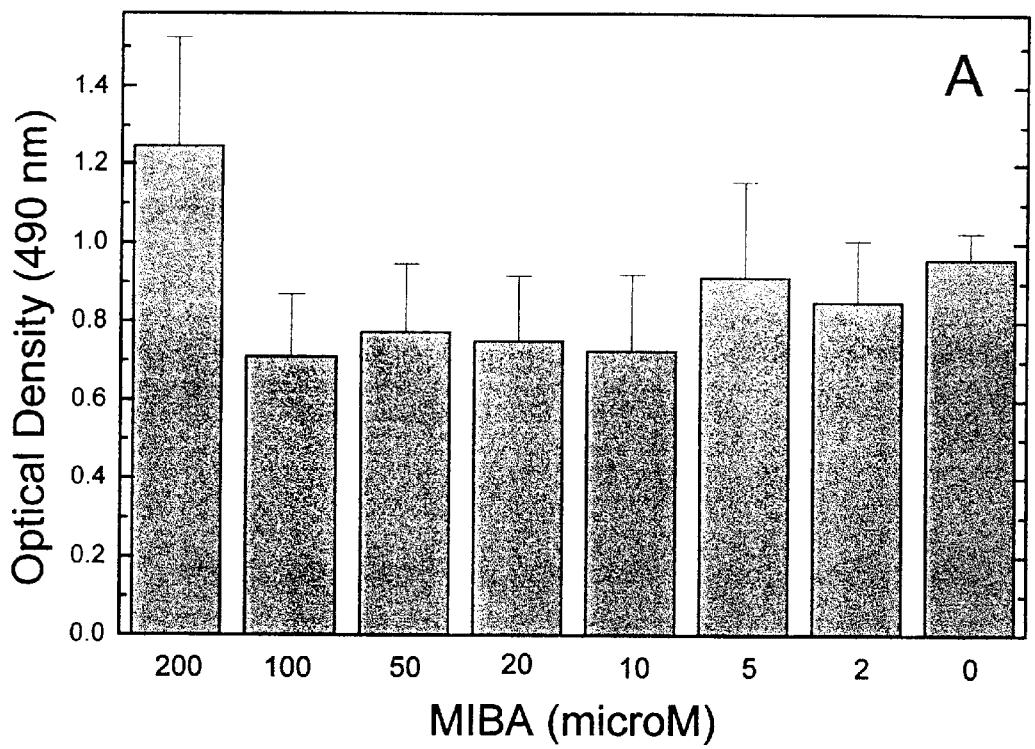
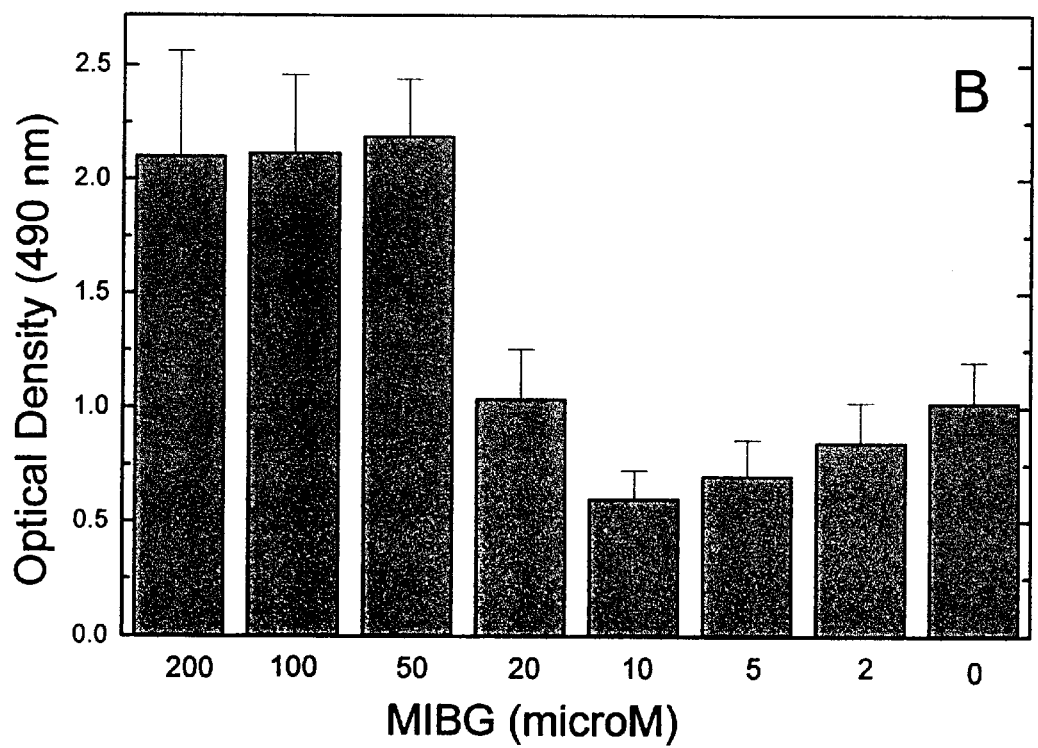

FIGURE 6
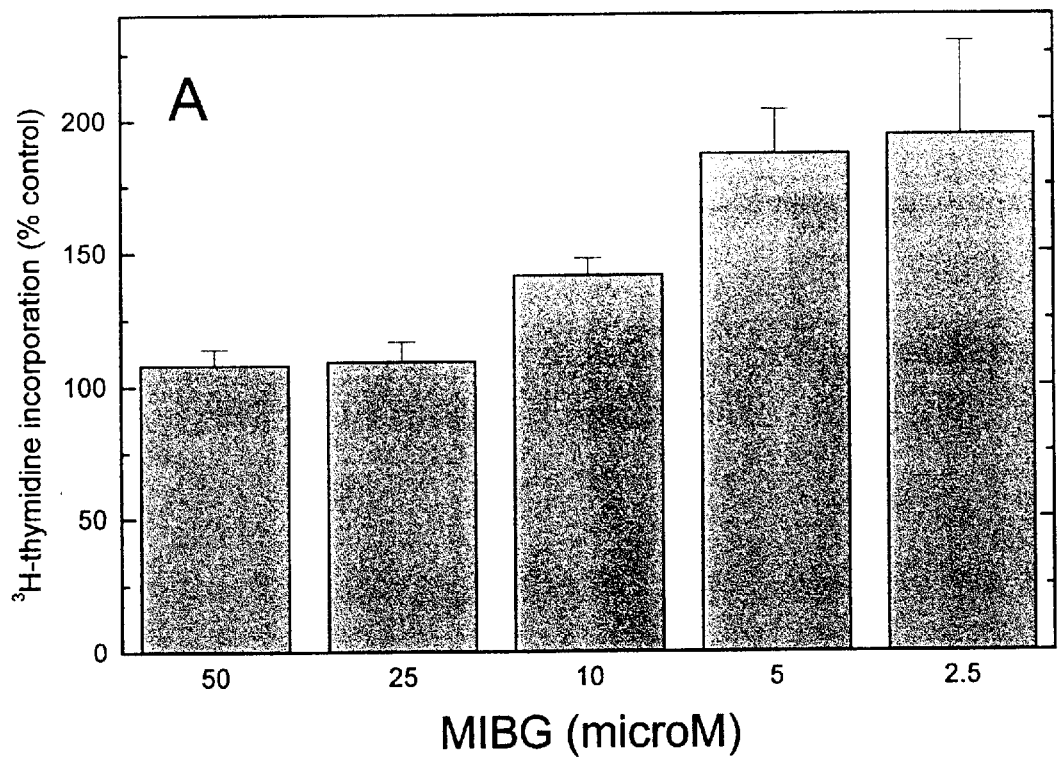
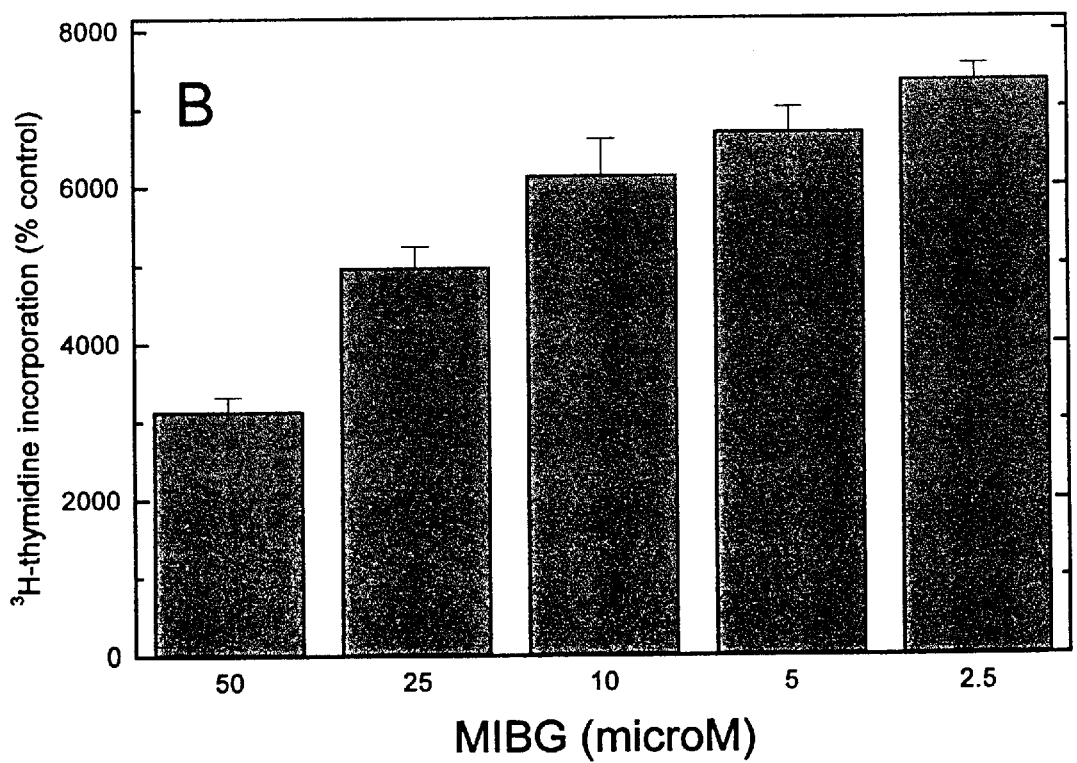

FIGURE 7
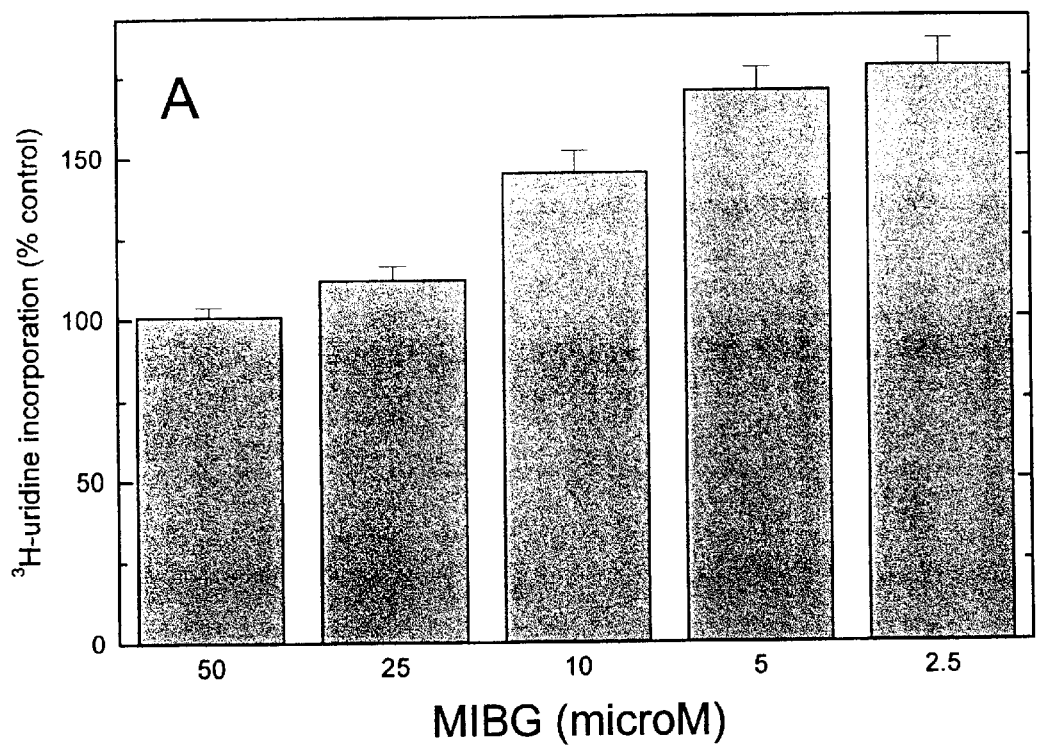
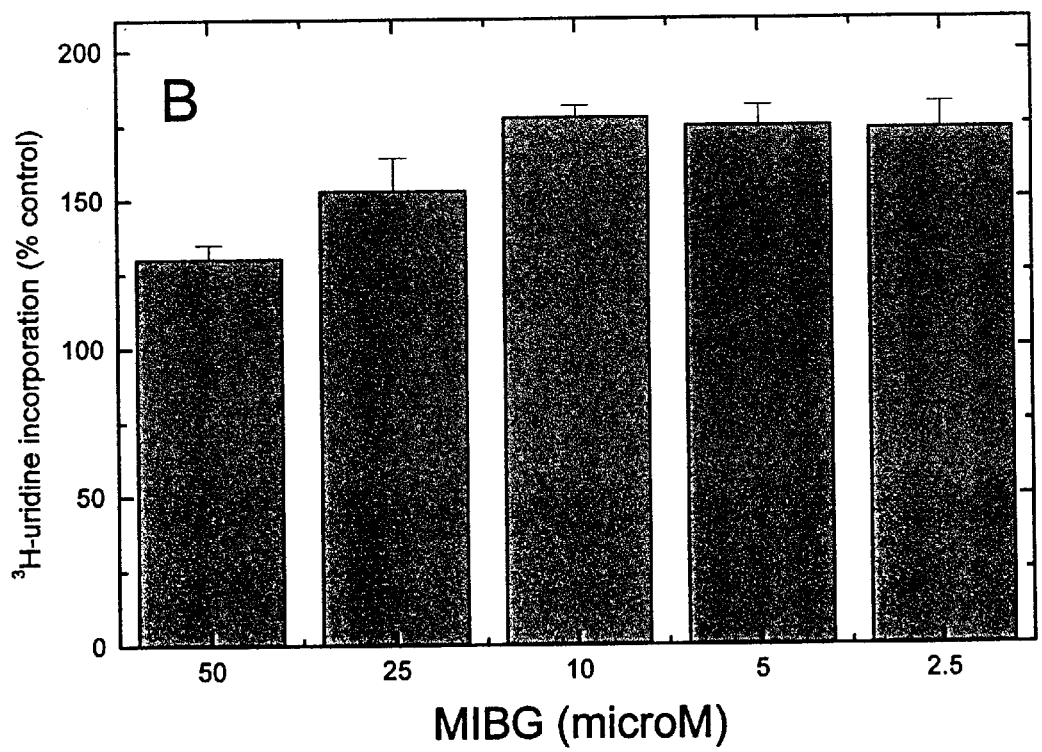

FIGURE 8
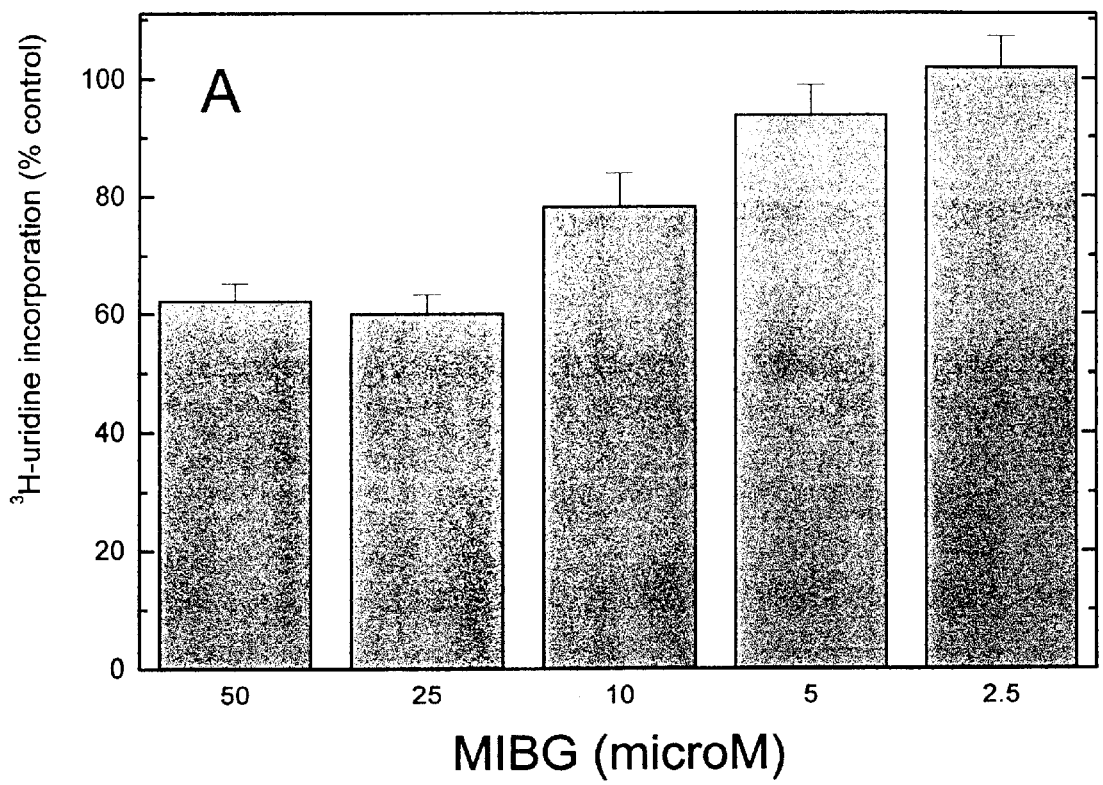
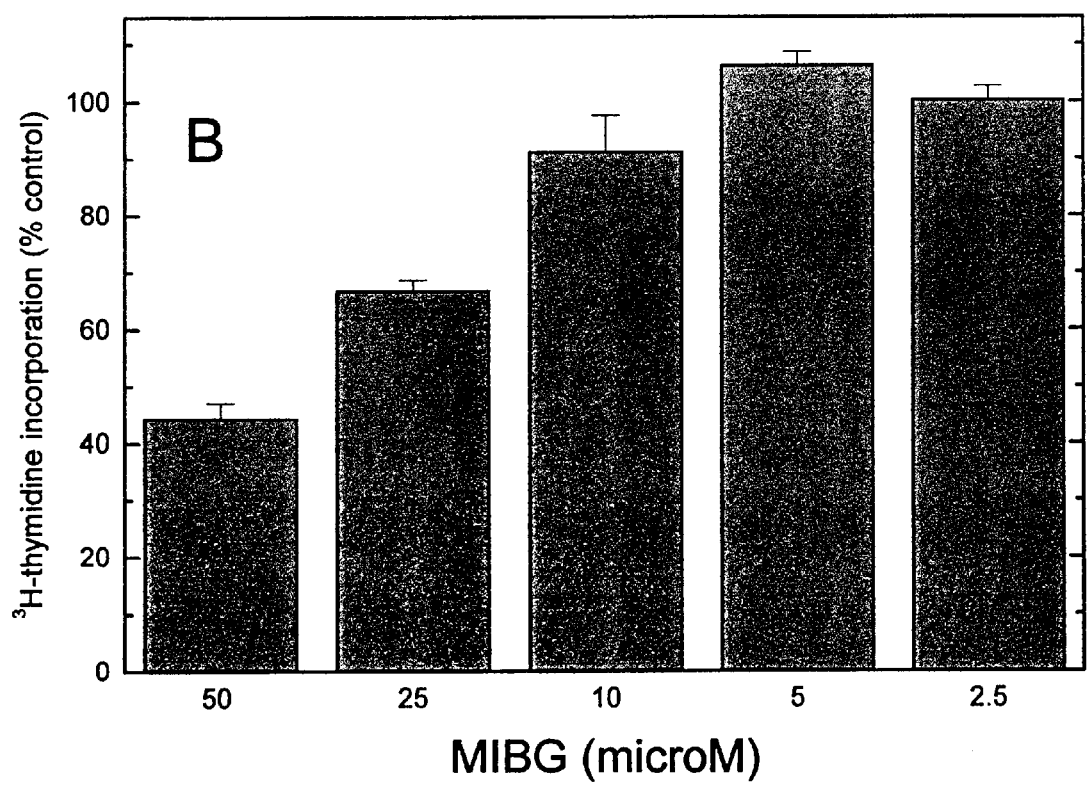

FIGURE 11
Control
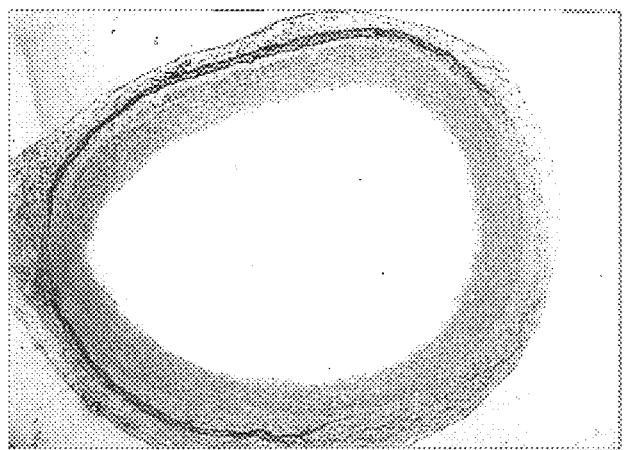
Injured
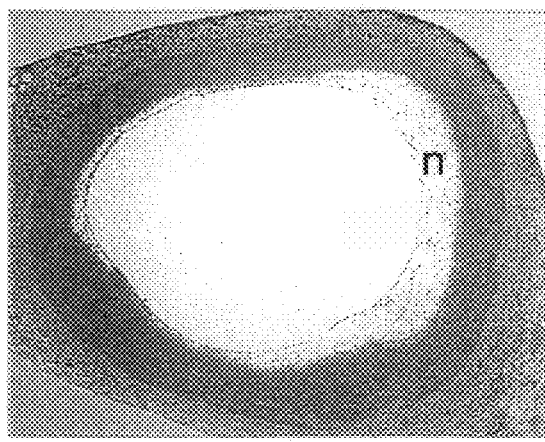
MIBG
Treated
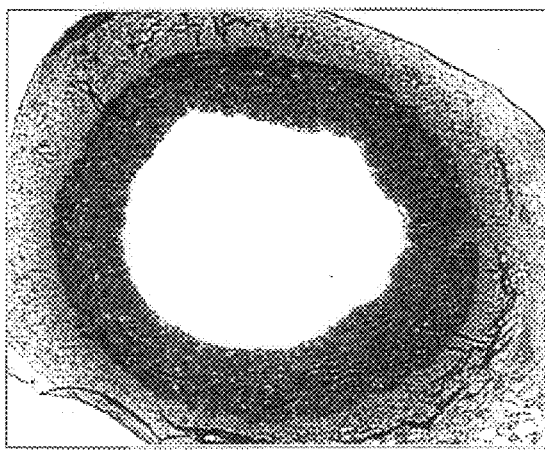

methylglyoxal *bis*-(guanylhydrazone)
(methylGAG)

meta-iodobenzylguanidine
(MIBG)

3-aminobenzamide

FIGURE 22
GUANIDINES
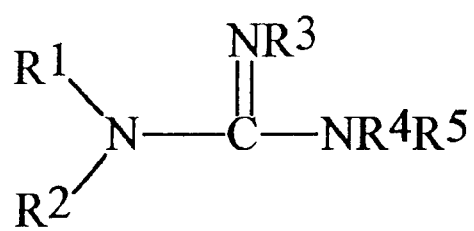
General Structure
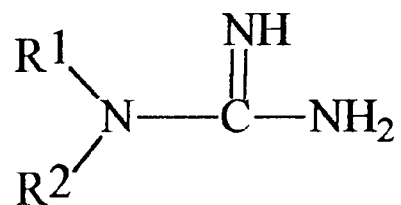
ADPRT Inhibitor Structure FIGURE 23  GUANYLHYDRAZONES
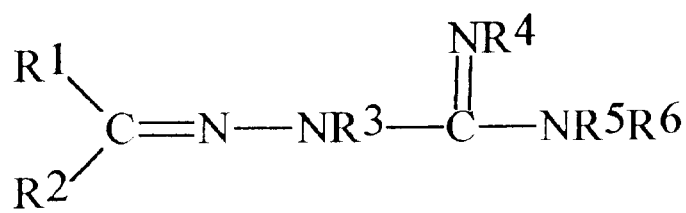
General Structure
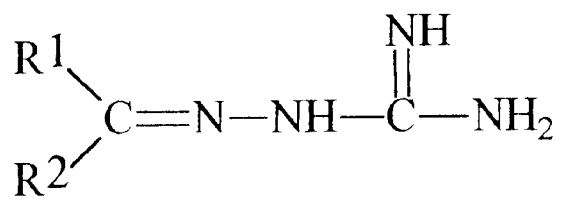
ADPRT Inhibitor Structure FIGURE 29
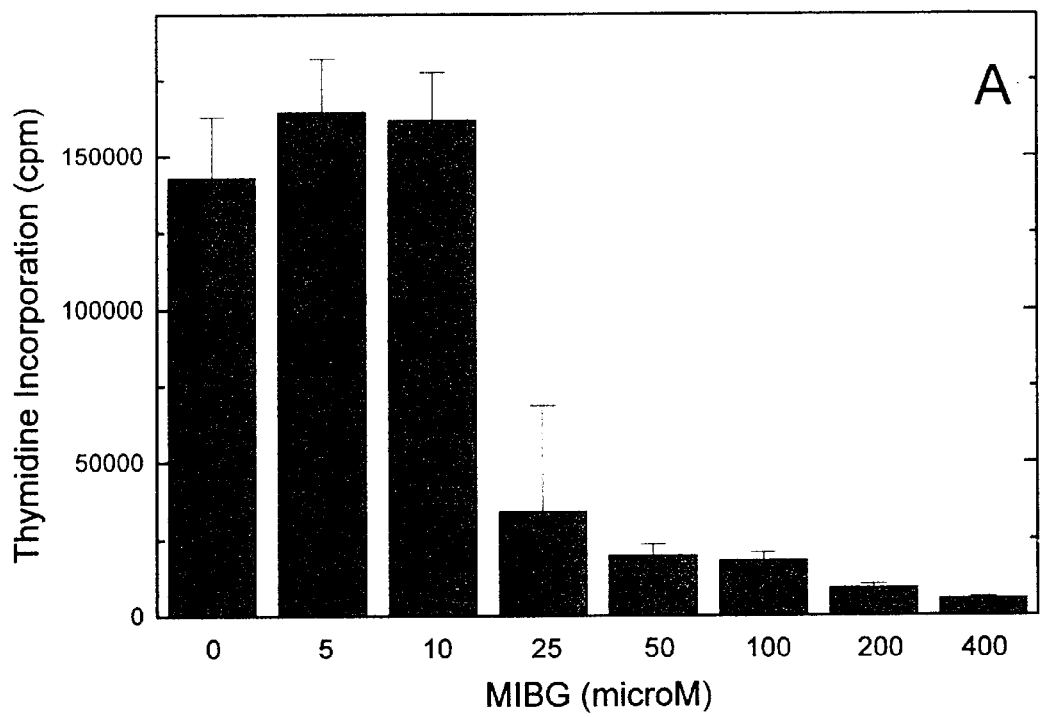
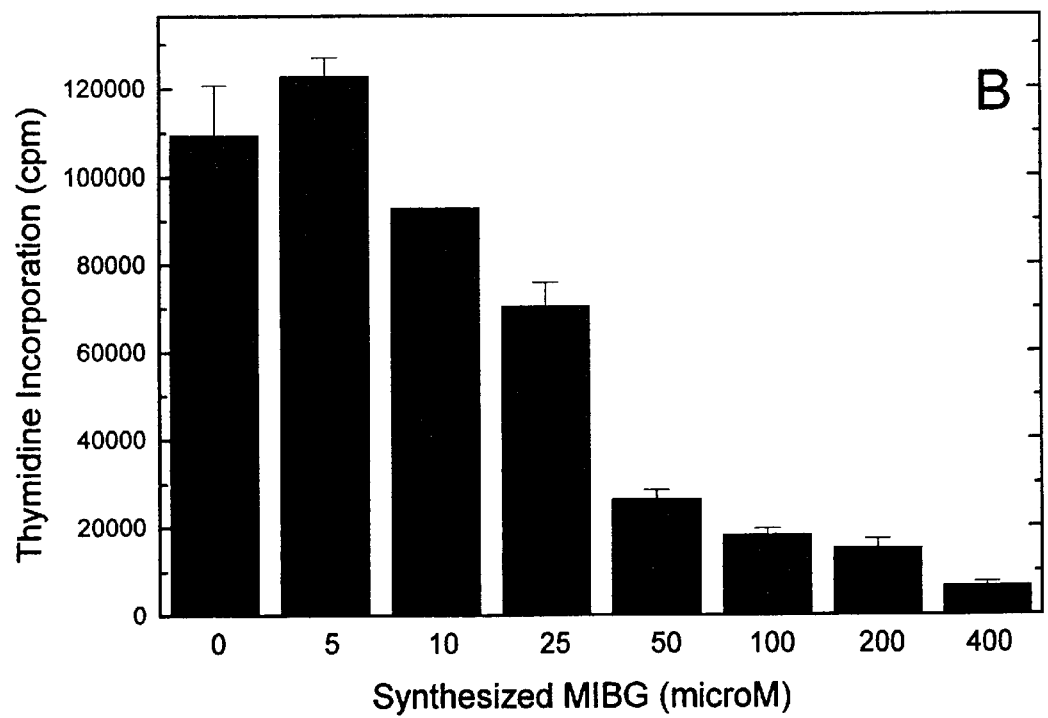

FIGURE 29(cont.)
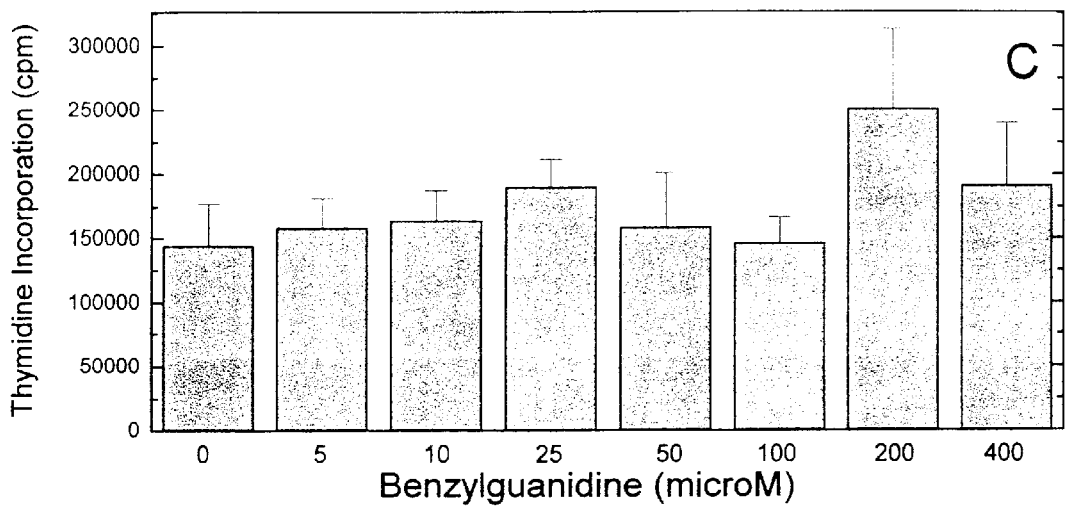
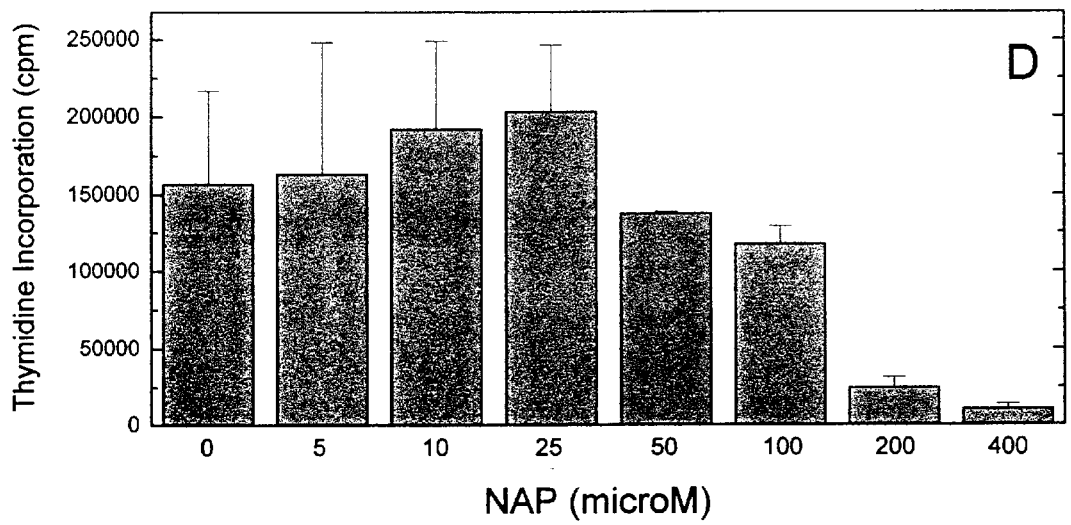
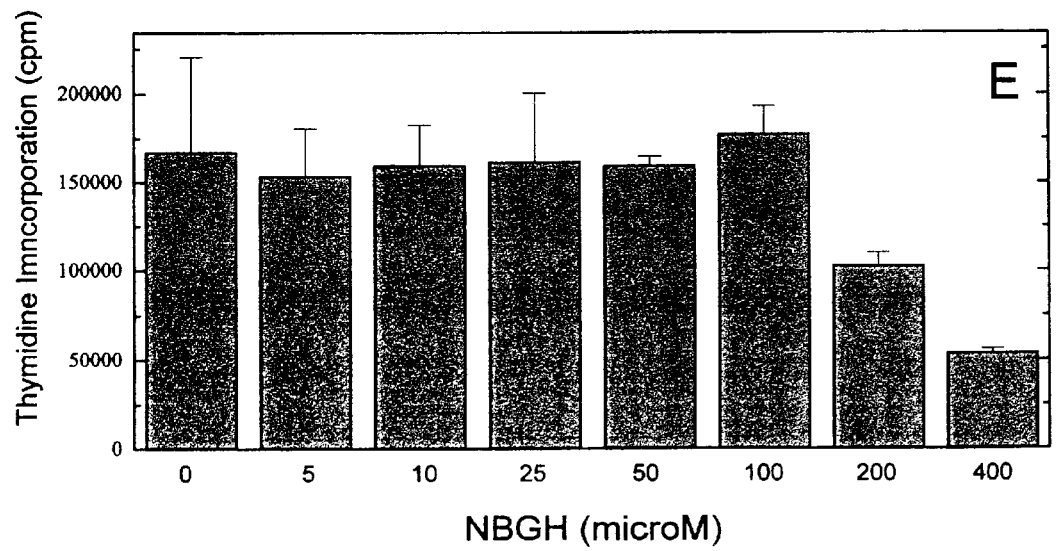

FIGURE 30
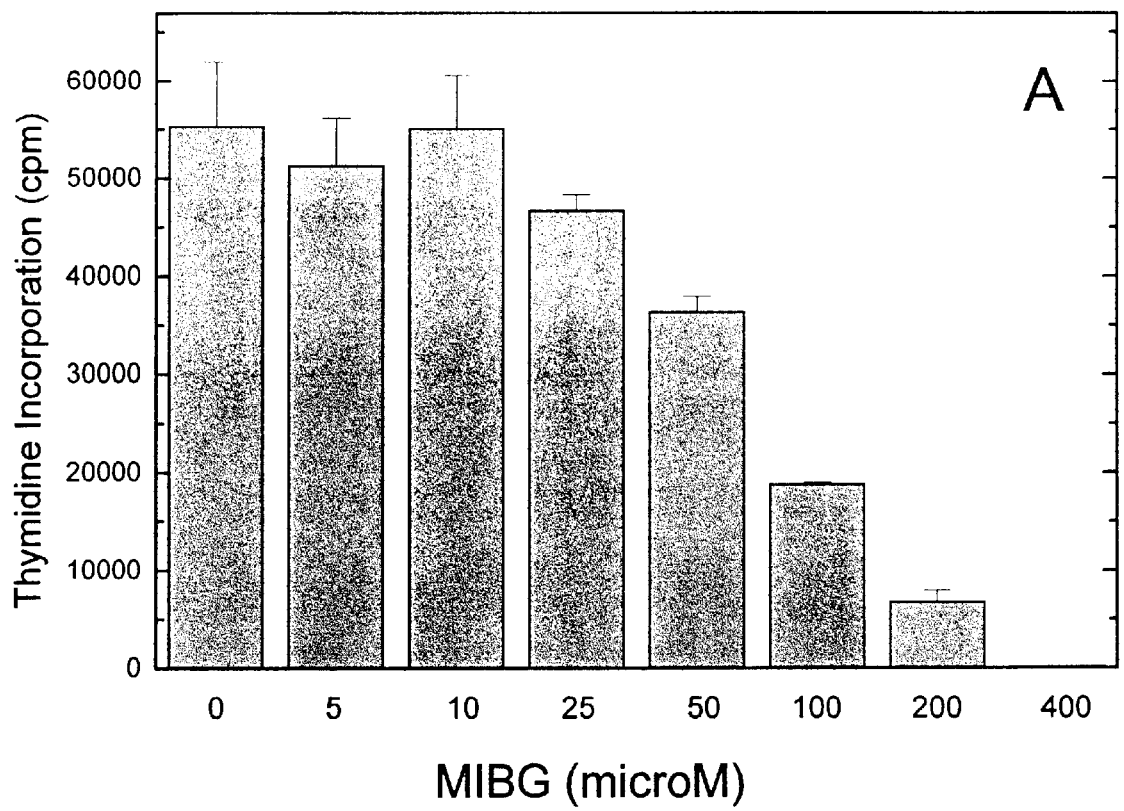
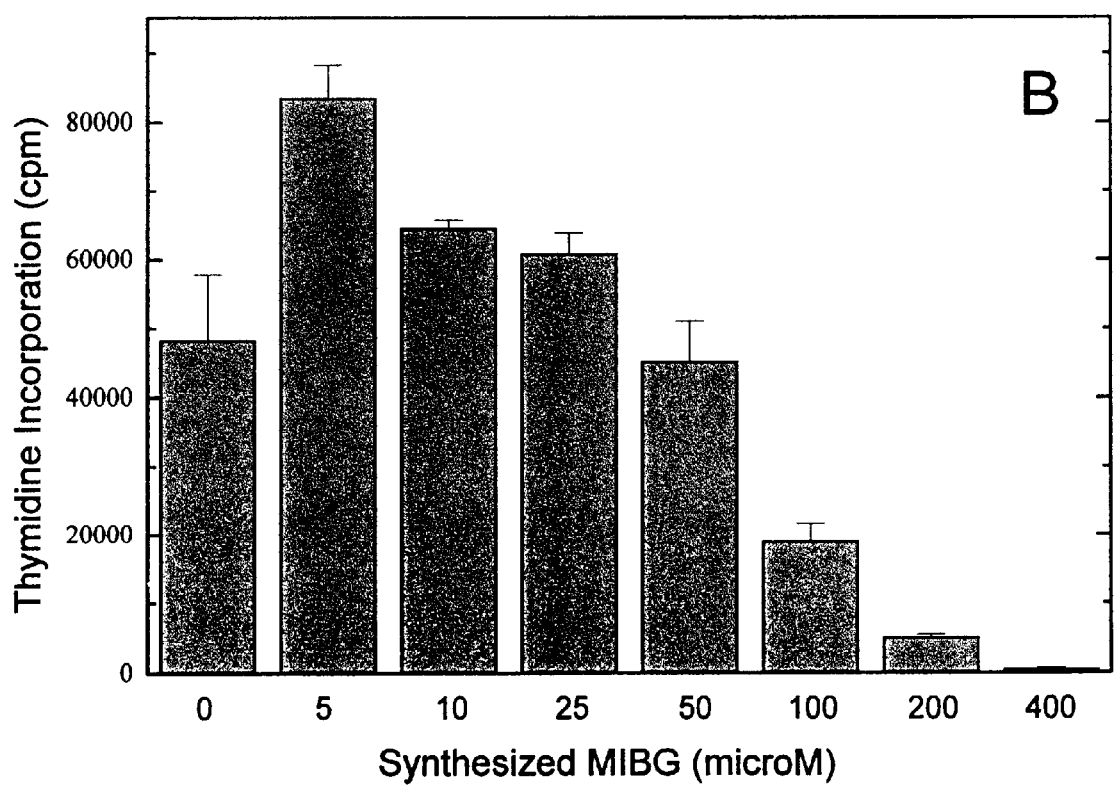

DEVICES AND COMPOUNDS FOR TREATING ARTERIAL RESTENOSIS

CROSS-REFERENCE TO RELATED APPLICATIONS

This application claims priority under 35 USC §119(e) to Provisional patent application Ser. No.60/150,696 filed on Jun. 2, 1999.

FIELD OF THE INVENTION

The present invention relates generally to the field of chemical compounds for medical treatments. More specifically, the present invention relates to compounds and devices for treating diseases or disorders associated with tissue damage due to environmental, interventional or autogenous injury.

BACKGROUND OF THE INVENTION

Diseases and disorders induced by tissue damage are a growing concern in the healthcare industry. Typically, these diseases are characterized by prolonged or unwanted response to injury, including inflammation of a tissue portion, secretion of degrading enzymes and/or compounds resulting in tissue destruction within the region and attempted tissue repair. Examples of such conditions include proliferative and/or inflammatory disorders, for example, restenosis, psoriasis, graft rejection, arthritis and multiple sclerosis.

Psoriasis is an inflammatory skin disease characterized by raised scaly lesions. Specifically, skin cells are pushed to the skin surface more quickly than the skin surface can shed dead skin cells. The end result is the formation of scaly lesions which are invaded by macrophage, lymphocytes and neutrophils, creating inflammation and soreness of the tissue region. In addition, these cells may produce growth factors which may in fact cause skin cells to be produced even more rapidly, thereby worsening the condition. While the exact cause is unknown, psoriasis is hypothesized to be an autoimmune disorder.

Multiple sclerosis is an inflammatory disease that affects the nervous system of an individual. Typically, the disease causes demyelination in the brain which in turn leads to a progressive loss of motor functions. While the cellular mechanism triggering destruction of the myelin is not understood, it is known that there is a localized increase in astrocyte proliferation and protease activity in afflicted regions. As with psoriasis, the exact cause of multiple sclerosis is unknown although it is also hypothesized to be an autoimmune disorder.

Inflammatory bowel disease includes a number of specific diseases which cause intestinal inflammation or ulceration. For example, in ulcerative colitis, an inflammatory reaction involving the colonic mucosa leads to ulcerations. Furthermore, repeated inflammatory responses lead to fibrosis and a subsequent shortening of the colon. Similarly, Crohn's disease is characterized by chronic inflammation of all layers of the intestinal wall.

Polycystic kidney disease is characterized by the formation of multiple cysts throughout the kidneys which progressively cause compression and destruction of kidney parenchyma. The disease appears to be caused by proliferation of epithelial cells in tubule segments within the kidneys, which in turn lead to fluid accumulation and enlargement of the kidneys.

Rheumatoid arthritis is a chronic inflammatory disease which causes pain, swelling and destruction of joints and can also lead to organ damage. Specifically, the disease is characterized by infiltration of the synovial membrane with white blood cells and a thickening of the synovial membrane. There is subsequent tissue growth within the joints as well as the release of degrading enzymes and compounds associated with the inflammatory response which leads to progressive destruction of the cartilage tissue. It is of note that rheumatoid arthritis is also hypothesized to be an autoimmune disorder.

Asthma is characterized by recurring airway obstruction caused by inflammatory cell infiltration, smooth muscle cell proliferation and hypertrophy in the airway and mucus secretion into the airway lumen.

Graft rejection occurs when the grafted tissue is recognized as foreign by the host's immune system. This rejection leads to inflammation and arteriosclerosis in the graft tissue and surrounding area.

Hypertrophic disease involves cell growth in the absence of increased cell number. This definition applies to a number of conditions associated with trauma, including hypertrophic gastropathy, hypertrophic burn scars, keloids, or postoperative hypertrophy affecting numerous tissues. For example, hypertension is an increase in smooth muscle cell volume within a blood vessel due to excessive pressure, lack of oxygen/nutrients or enhanced production of hypertrophy-inducing factors released as a result of trauma distinct from the site of action (for example, kidney disease). Also, hypertrophic cardiac disease (for example, congestive heart failure, hypertrophic cardiomyopathy, valve replacement surgery) results from an increase in cardiomyocyte volume as a result of hypoxia, surgical intervention or genetic defect. Cellular hypertrophy and inflammation occur in the region affected by the causative factor.

Cutaneous fibrosis is an integral component of a variety of human disorders including keloids, hypertrophic scars, and most notably, scleroderma. Each has its own etiology and unique clinical characteristics, but all involve the disregulation of connective tissue metabolism, in particular, the activation of dermal fibroblasts. Atrophic scars also occur secondary to surgery, trauma, and common conditions such as acne vulgaris and varicella. Hypertrophic scars and keloids occur as the result of an exaggerated wound healing response of the skin following injury. Keloids and hypertrophic scars are benign fibrous growths that occur after trauma or wounding of the skin which are frequently pruritic, painful and occasionally form strictures. Keloid and hypertrophic scarring develops as a result of a proliferation of dermal tissue following skin injury. These proliferative scars are characterized by increased collagen and glycosaminoglycan content, as well as increased collagen turnover. Excision only of hypertrophic scars and keloids results in 45–100% recurrence. The current objective is to decrease scar height and reduce the number of post-operative recurrences.

Vascular lesions that develop in autologous saphenous vein grafts (SVG) after transplantation into the aorto-coronary circulation or the peripheral vascular circulation share elements of smooth muscle migration, proliferation, and fibrous tissue deposition in common with nibrointimal proliferation, post-operative recurrences of the fibrovascular proliferations of pterygia and keloids.

Restenosis is caused by vascular stress or injury and leads to vessel wall thickening and loss of blood flow. These stresses may be, for example, mechanical, hypoxia, injury, shear-stress, pharmacological, infectious, inflammatory, oxidative, immunogenic, diabetic or pressure. The normal arterial vessel wall consists of a regular arrangement of endothelial, smooth muscle and fibroblast cells, present in three distinct layers of endothelium, media and adventitia. A single layer of endothelial cells forms the luminal barrier to blood-borne signals that modulate vascular function. The adventitia, which forms the outer layer around the artery, consists primarily of extracellular matrix as well as some fibroblasts, nerve fibres and microvessels. The media consists of numerous layers of smooth muscle cells (SMCs) intermixed with extracellular matrix that is bound by the internal and external elastic lamina.

The response to injury or other stress stimuli varies between the different cellular components of the vessel. Endothelial cells are capable of proliferation and migration, properties that permit re-endothelialization of the vessel after denudation or injury (Reidy, 1985, *Lab Invest* 53: 513–520). Medial SMCs are also able to reversibly modulate their phenotype which allows for their proliferation and/or migration into the intima at the site of injury (Schwartz et al, 1995, *Circ Res* 77: 445–465). It is these characteristics that lead to the adaptive and pathogenic growth of SMCs which is key to vascular remodelling and lesion formation.

This is of particular concern for the treatment of coronary disease, wherein a common treatment for constricted, clogged or narrowed coronary arteries is balloon angioplasty. Angioplasty involves the use of a balloon-tipped catheter which is inserted into the heart's vessels to open partially blocked, or stenotic, coronary arteries. While balloon angioplasty does widen the restricted artery, a significant number of patients have renewed narrowing of the widened segment soon after the procedure. This subsequent narrowing of the artery is called restenosis and can necessitate the repetition of the angioplasty procedure or require alternative treatment such as coronary bypass graft surgery. Furthermore, restenosis occurs as a result of trauma to the vessel regardless of the method by which the injury is inflicted. Therefore, restenosis is not exclusive to angioplasty and is a common result of other (cardiac or peripheral) revascularization procedures (eg. stenting) or procedures involving vascular grafting (eg. bypass surgery, organ transplantation). It is also a problem associated with hemoaccess and other procedures involving long term intravenous delivery.

Restenosis appears to be a response to injury of arterial wall, and appears to consist of the following events: platelet adhesion and aggregation on the damaged endothelium; release of platelet-derived growth factors; inflammation of the injured zone (Kornowski et al, 1998, *J Am Coll Cardiaol* 31: 224–230); secretion of specification chemotactic proteins from the damaged cells leading to recruitment of monocytes to the site of injury (Furukawa et al, 1999, *Circ Res* 84: 306–314); differentiation of monocytes into macrophages that produce matrix metalloproteinases required for cell migration; dedifferentiation of the smooth muscle cells after their activation by the growth factors; migration and proliferation of transformed smooth muscle cells, with secretion of extracellular matrix material; and re-growth of endothelium over the injured area.

U.S. Pat. No. 5,527,532 and 5,455,039 teach methods of regulating repair following injury to the lumen. In these patents, a modulator of cell or tissue growth, for example, heparin, is applied to an extraluminal site adjacent the injured tissue in a polymer release matrix such that the heparin is administered over a prolonged period. Other examples of growth modulating agents provided are angiotensin converting enzyme inhibitors, angiotensin, angiogenic growth factors, heparin binding growth factors, FGF, PDGF, TGF-$\beta$, immunosuppressants, calcium channel inhibitor, cytokines and interleukins. The polymer release matrix is preferably composed of ethylene-vinyl acetate copolymer although other polyorthoester systems are also described.

There have been several proposed treatments for preventing restenosis, such as treatment with antioxidants or placing collapsible supports (i.e. stents) inside arteries, with varying success. As a consequence, there is an on-going search for compounds useful in treating proliferative disorders. For example, preliminary studies with 3-aminobenzamide, a potent ($K_i$=10 $\mu$m) inhibitor of poly(ADP-ribose) polymerase (PARP), indicated this compound could inhibit cell growth at concentrations of 1 mM and greater (Zahradka and Yau, 1994).

It is important to note however that restenosis involves a number of distinct processes, including cell proliferation, cell migration and alterations in differentiated state (i.e. phenotype) of the medial smooth muscle cells, any of which could be a target for preventing restenosis. A major controversy still rages with respect to the relative importance of each process. It has become evident, however, that the rate of cell proliferation is infrequent in vessels undergoing restenosis (O'Brien et al, 1993, *Circ Res* 73: 223–231). Nevertheless, some inhibitors of cell proliferation have been shown to inhibit restenosis (Braun-Dullaeus et al, 1998, *Circulation* 98: 82–89). This discrepancy may be attributed to the effect of antiproliferative compounds on the other processes. For example, it has been demonstrated that the retinoblastoma protein regulates both the proliferation and the differentiation of skeletal muscles (Gu et al, 1993, *Cell* 72: 309–324), and a similar role in smooth muscle cells has been proposed (Pappas et al, 1998, *J Surg Res* 76: 149153). Similarly, a process necessary for proliferation may also be important for stimulating cell migration. For example, the transcription factor NF-$\kappa$KB has been shown to mediate events associated with both cell migration and cell proliferation (Lindner, 1998, *Pathobiology* 66: 311–320; Autieri et al, 1995, *Biochem Biophys Res Commun* 213: 827–836). Other intracellular factors also have dual functions. The role of cell migration has therefore become a focus of interest (Schwartz, 1997, *J Clin Invest* 99: 2814–2817; Casscells, 1992, *Circulation* 86: 723–729). Two lines of evidence suggest that migration has a greater contribution to restenosis than proliferation. One study (Bauriedel et al, 1992, *Circulation* 85: 554–564) suggests the smooth muscle cells of restenotic lesions migrate faster than their normal counterparts. Another study (Le Feuvre et al, 1998, *CorArtery Dis* 9: 805–814) showed that remodelling of the vessel after angioplasty occurred with minimal proliferation. Furthermore, this report suggests the majority of proliferating cells were not of smooth muscle origin. These observations support the results reported in several other studies relating to migration versus proliferation. First, inhibition of matrix metalloproteinases, the enzymes responsible for degrading the extracellular matrix and therefore freeing the cells for migration, prevents inhibit restenosis (George et al, 1998, *Hum Gene Ther* 9: 867–877). These agents do not inhibit cell proliferation. Similarly, the kinase inhibitor fasudil has been shown to reduce restenosis while lacking anti-proliferation activity (Negoro et al, 1999, *Biochem Biophys Res Comm* 262: 211–215). Second, various agents have been demonstrated to inhibit smooth muscle cell proliferation without having any effect in blocking restenosis. Among these compounds are lovastatin and fluvastin (two of several HMG-COA reductase inhibitors), enalapril (a typical ACE inhibitor), colchicine, carvedilol, heparin and phosporothioate oligonucleotides (Freed et al, 1995, *Am J Cardiol* 76: 1185–1188; Geary et al, 1995, *Circulation* 91: 2972–2981; Serruys et al, 2000, *Circulation* 101: 1512–1518; Gradus-Pizio, 1995, *J Am Coll Cardiol* 6: 15491–1557; Simon et al, 1999, *Antisense Nuci Acid Drug Dev* 9: 549–553). It must also be stressed that arterial remodelling during restenosis does not require cell proliferation (Le Feuvre et al, 1998).

These data therefore support the premise that modulation of smooth muscle phenotype, exclusive of the change in proliferative potential of these cells, is the most important facet for therapeutic intervention. It is nevertheless unclear what component of the change is most important. Migration is considered to be essential. However, the deposition of extracellular matrix proteins is integral to formation of the neointima. Infiltration by inflammatory cells contributes as well. Thus, approaches directly focused upon inhibiting cell proliferation may not be successful.

As discussed above, a major emphasis for the treatment of restenosis has been placed on the prevention of either cell proliferation or migration. Alternatively, the aim has been to prevent inflammation. When one examines the etiology of restenosis, which results from an exaggerated wound healing process, a number of distinct responses are evident such as, for example, proliferation, migration, inflammation and fibrosis. In all cases, these events occur as a result of phenotypic reprogramming of the smooth muscle cells. For instance, the release of metalloproteinases that degrade the extracellular matrix permits migration. Migration into the vascular lumen allows proliferation. The cells also synthesize and secrete abundant collagen and fibronectin once they enter the lumen. Inflammation due to invasion by monocytes and leukocytes results from the expression of specific adhesion molecules that direct infiltration. Their entry is also enhanced by the secretion of specific chemattractant molecules. All of these events result from modulation of smooth muscle cell phenotype due to trauma or stress. Inhibition of the differentiation process would therefore accomplish all of the relevant objectives since each event would be blocked as well. As such, an anti-differentiation agent would likely be an effective treatment for the diseases and disorders induced by tissue damage discussed above.

ADP-ribosylation is a post-translational modification comprising the attachment of ADP-ribose to proteins (shown in FIG. 16), either as single moieties or as a long polymer (Zahradka and Yau, 1994, *Mol Cell Biol* 138: 91–98). ADP-ribosylation occurs in two distinct forms: nuclear poly(ADP-ribosyl)ation and mono(ADP-ribosyl)ation (Moss and Zahradka in ADP-ribosylation: Metabolic Effects and Regulatory Functions (Boston: Kluwer Academic Publishers, 1994)). Nuclear poly(ADP-ribosyl)ation regulates protein-DNA interactions (Zahradka and Ebisuzaki, 1982, *Eur J Biochem* 127: 579–585) and is proposed to be involved in for example the modulation of chromatin condensation via histone modification (de Murcia et al, 1986, *J Biol Chem* 261: 7011–7017) and the regulation of DNA repair activity following damage by alkylating agents and high energy irradiation (Lindahl et al, 1995, *TIBS* 20: 405–411). In addition, proteolytic cleavage of poly(ADP-ribose) polymerase (PARP) has also been recently identified as one of the earliest events in apoptosis, or programmed cell death (Duriez and Shah, 1997, *Biochem Cel Biol* 75: 337–349). Mono(ADP-ribosyl)ation, on the other hand, is a process associated primarily with the cytoplasmic and membrane fractions of a cell. The best understood of the mono (AD-Pribosyl)ation reactions are those of bacterial toxins.

Several eukaryotic mono(ADP-ribosyl)ation transferases (ADPRTs), however, have also been identified and characterized. For example, cysteine-dependent ADPRT modifies G, while an arginine-dependent ADPRT modifies $G_s$ (Tanuma et al, 1988, *J Biol Chem* 263: 5485–5489; Inageda et al, 1991, *Biochem Biophys Res Commun* 176: 1014–1019). As well, a phosphatidylinositol-linked arginine-dependent ADPRT is present on the external surface of skeletal and cardiac cells, and controls cell attachment by modifying α7-integrin (Okazaki and Moss, 1998, *J Biol Chem* 273: 23617–23620). Other ADPRTs are associated with vesicular movement in the Golgi, since ARFs (ADP-ribosylation factors) are essential for these events (Kanoh et al, 1997, *J Biol Chem* 272: 5421–5429). ADPRTs have also been linked to the activation of small GTP-binding proteins such as ras, rho and raf, key components in signal transduction (Maehama et al, 1994, *Mol Cell Biochem* 138: 135–140). The ubiquitous presence of ADPRTs in all cell types suggests that they are crucial elements in normal cell function.

As stated above, preliminary studies with 3-aminobenzamide, a potent ($K_1=10 \mu M$) inhibitor of PARP, indicated this compound could inhibit cell growth at concentrations of 1 mM and greater (Zahradka and Yau, 1994). These observations, as well as the findings reported by other laboratories, did not fit the pattern expected for PARP. Specifically, while there was considerable evidence to link PARP with DNA recombination events and DNA repair (Lindahl et al, 1995, *Philos Trans R Soc Lond B Biol Sci* 347: 57–62), there was only limited evidence to link PARP directly with cell proliferation. The studies by Rankin et al (Rankin et al, 1989, *J Biol Chem* 264: 4312–4317) and Banasik et al (Banasik et al, 1992, *J Biol Chem* 267: 1569–1575) clearly showed that 3-aminobenzamide inhibited mono(ADP-ribosyl)ation at high concentrations (>1 mM). Based on these observations, it was postulated that inhibition of mono(ADP-ribosyl)ation was the mechanism by which 3-aminobenzamide inhibited cell growth (Zahradka and Yau, 1994; Yau et al, 1998, *Eur J Biochem* 253: 91–100).

As a consequence, decoy substrates of mono(ADP-ribosyl)ation were sought to be tested as anti-inductive agents. Meta-iodobenzylguanidine (MIBG) is a norepinephrine analogue that also belongs to a class of compounds distinguished by a guanidino moiety. MIBG has also been shown to be a selective inhibitor of normal function of arginine-dependent mono(ADP-ribosyl)ation (Loesberg et al, 1990, *Biochim Biophys Acta* 1037: 92–99) and it is the guanidino group that is the functional portion with respect to modification by ADP-ribosylation.

It has also been shown that while MIBG apparently prevents an increase in cell number, it had no effect on DNA synthesis, based on thymidine uptake experiments (Thyberg et al, 1995, *Differentiation* 59: 243–252). On this basis, it was concluded that MIBG inhibits progression through the cell cycle, although no evidence for this mechanism was presented. Instead, there was commentary about the involvement of c-ras, a critical mediator of cell progression that may be a target for mono(ADP-ribosyl)ation. On the other hand, Thyberg et al observed that MIBG decreased the production of collagen type I, the most abundant component of the extracellular matrix. Similarly, there was a lesser conversion of the cells to the dedifferentiated (synthetic) state in the presence of MIBG. It is argued that MIBG may therefore affect the interaction of smooth muscle cells with the extracellular matrix and that in view of this, MIBG may be a tool for investigating the role of smooth muscle cells in connection with atherogenesis and restenosis. However, it is important to note that Thyberg does not teach or suggest the use of MIBG as a treatment for restenosis.

MIBG has previously been shown to be selectively accumulated in adrenal glands following injection into dogs (Wieland et al, 1981, *J Nucl Med* 22: 22–31). This study was based on observations that aralkylguanidines are potent neuron blocking agents that apparently act on adrenergic nerves (Short and Darby, 1967, *J Med Chem* 10: 833–840). Since that time, MIBG has been used as an imaging agent for the detection of pheochromocytoma (tumors of the adrenal gland) via scintillography (Hoefnagel et al, 1987, *Eur J Nucl Med* 13: 187–191). It is of note that in these imaging experiments, MIBG combined with a label was used at a maximum concentration of approximately 0.065 mg/kg of the test subject. As such, MIBG itself was used as a carrier for delivering radiation doses and not as an actual treatment. Its application to other neuroendocrine tumors, particularly neuroblastomas, has also been tested, and it has been found to be an extremely sensitive diagnostic tool. Other carcinomas are also detected with MIBG, but other imaging agents have been shown to provide greater sensitivity. Radiolabelled MIBG is employed in scintillography, however, the amounts that are utilized are quite small and pose no danger to the patient or the organ. Trials with MIBG as a radiopharmaceutical agent have been designed on the basis that accumulation of high doses of radioactivity can inhibit tumor growth (Shapiro et al, 1995, *Q J Nucl Med* 39: 55–57). Thus higher doses of radiolabelled MIBG may be useful in treatment. To date, there have been encouraging results, but insufficient to support first line use (Taal et al, 1996, *J Clin Oncol* 14:1829–1836). Nevertheless, it has been found useful for treating inoperable tumors. Furthermore, there is evidence that it may be more effective when combined with other therapies. However, it is important to note that MIBG was selected based on its accumulation in fast-growing cells and not on its activity as an ADPRT inhibitor.

Furthermore, MIBG's accumulation in sympathetic neurons led to tests for its utility in identifying changes in cardiac function. This reasoning was based on the fact that cardiac innervation is altered in the hypertrophied heart. In part this is considered a result of sympathetic neuron loss after myocardial infarction. Thus a reduction in MIBG uptake by cardiac tissues, called an MIBG defect, is deemed to correlate with cardiac disfunction (Somsen et al, 1996, *Int J Card Imaging* 12: 305–310; Tamaki et al, 1997, *Ann Nucl Med* 11: 55–66). No clear consensus on the utility of MIBG in the diagnosis of heart failure has yet been reached, although there are still numerous attempts to identify the conditions for which MIBG may be useful. However, it is once again the uptake characteristics of MIBG that are being utilized.

In other studies, MIBG has been used as an anti-cancer drug at a concentration of approximately 1.5 mg/kg of subject (Kuin et al, 1998, *Cancer Chemother Pharmacol* 42: 37–45; Kuin et al, 1999, *Brit J Cancer* 79: 793–801). However, it is important to note that in these studies, MIBG and BG were selected based on its activity as a mitochondrial inhibitor. Furthermore, the MIBG analogue MIBA is also a mitochondrial inhibitor and would also have been suitable.

Clearly, there is a need for improved treatments and methods for preventing disorders that occur as a result of alterations in the migratory, proliferative and inflammatory responses of cells within tissues. In particular, the treatments should prevent the shift into the inductive state and the cell phenotype modification associated with tissue repair. Ideally, these treatments should be designed to target the area at risk preferentially or to be localized thereabouts. In this manner, potential side effects and/or complications from treatment could be minimized.

SUMMARY OF THE INVENTION

According to a first aspect of the invention, there is provided a pharmaceutical composition for treating or preventing an injury-related disorder comprising an ADPRT decoy substrate and a suitable excipient.

According to a second aspect of the invention, there is provided an ADPRT decoy substrate for treating or preventing an injury-related disorder.

According to a third aspect of the invention, there is provided a method of treating or preventing an injury-related disorder comprising: providing a pharmacologically effective amount of a pharmaceutical composition comprising an ADPRT decoy substrate and a suitable excipient; and administering the pharmaceutical composition to an individual inflicted with the injury-related disorder.

According to a fourth aspect of the invention, there is provided a method of inhibiting restenosis comprising: providing a pharmaceutical composition comprising an ADPRT decoy substrate in admixture with an adhesive agent; providing a damaged vessel; and applying the pharmaceutical composition to the damaged vessel, thereby inhibiting smooth muscle cell differentiation, migration and proliferation.

According to a fifth aspect of the invention, there is provided a kit comprising an ADPRT decoy substrate for treating or preventing an injury-related disorder and instructions for utilizing the ADPRT decoy substrate for treating or preventing the injury related disorder.

BRIEF DESCRIPTION OF THE DRAWINGS

FIG. 4A shows results of flow cytometry analysis of H4IIE cells after insulin stimulation in the absence of MIBG; FIG. 4B shows results of flow cytometry analysis of H4IIE cells after insulin stimulation in the presence of MIBG.

FIG. 5 is a bar graph showing cellular toxicity of varying concentrations of MIBA and MIBG in H4IIE cells based on colorimetric detection of lactate dehydrogenase at $OD_{490}$.

FIG. 6A is a bar graph showing the effect of varying concentrations of MIBG on DNA synthesis in smooth muscle cells following stimulation by angiotensin II; FIG. 6B is a bar graph showing the effect of varying concentrations of MIBG on DNA synthesis in smooth muscle cells following stimulation by 2% serum.

FIG. 7A is a bar graph showing the effect of varying concentrations of MIBG on RNA synthesis in smooth muscle cells following stimulation angiotensin A; FIG. 7B is a bar graph showing the effect of varying concentrations of MIBG on RNA synthesis in smooth muscle cells following stimulation 2% serum.

FIG. 8A is a bar graph showing the effect of varying concentrations of MIBG on DNA synthesis in quiescent porcine coronary artery smooth muscle cells; FIG. 8B is a bar graph showing the effect of varying concentrations of MIBG on RNA synthesis in quiescent porcine coronary artery smooth muscle cells.

FIG. 11 is a histology of porcine coronary arteries after organ culture.

FIG. 22 shows the general chemical structure of the guanidine family (Panel A) and the subset capable of inhibiting ADPRT (Panel B).

FIG. 23 shows the general chemical structure of guanylhydrazones (Panel A) and the subset capable of inhibiting ADPRT (Panel B).

FIG. 29 is a bar graph of thymidine incorporation in H4IIE cells at various concentrations of (A) synthesized MIBG, (B) BG, (C) NAP and (D) o-nitrobenzylguanylhydrazone.

DESCRIPTION OF THE PREFERRED EMBODIMENTS

Figure 1:
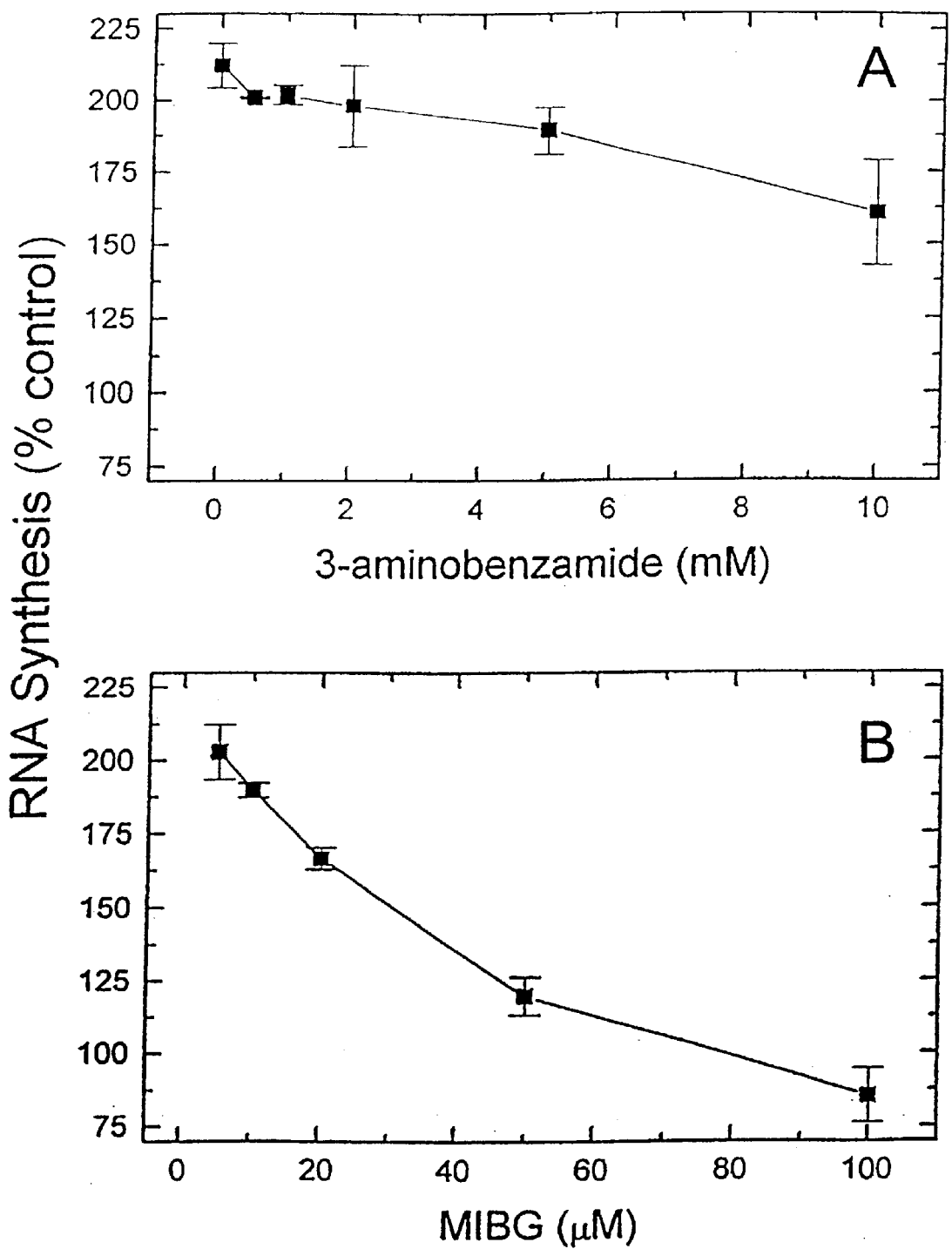
FIG. 1 is a graph showing the effect of varying concentrations of 3-aminobenzamide and MIBG on RNA synthesis in H4IIE cells.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

As used herein, "decoy substrate" refers to a compound that serves as a substrate in an enzymatic reaction in place of the endogenous substrate. The presence of this compound therefore reduces the utilization of the endogenous substrate and reduces the effect of that enzyme on cellular metabolism (i.e., the ADPRT decoy substrate competes with the endogenous substrate). Examples of ADPRT substrates are provided herein and in FIGS. 14, 15, 22 and 23.

As used herein, "proliferation" refers to the sum of numerous processes controlling the duplication (increase in number) of cells. Proliferation, which can also be termed hyperplasia, is distinct from hypertrophy which is distinguished by enlargement of the cells in the absence of cell division.

As used herein, "inflammatory disease" refers to any disease which is characterized by vascular changes, for example, edema, tissue destruction and attempts at repair by connective tissue replacement. Examples of such diseases include for example restenosis, fibrosis, myocardial infarction-induced hypertrophy, arthritis, multiple sclerosis and graft rejection.

As used herein, "migration" refers to the process by which cells move from one location to another.

As used herein, "phenotype" refers to the characteristics expressed by a specific cell as a result of its genetic program and its local environment.

As used herein, "injury-related disease or disorder" or "inductive disease or disorder" refers to a disease or disorder characterized by conditions similar to injury response. These include disorders wherein unwanted repair is occurring as well as auto-immune diseases. Exemplary examples include, but are by no means limited to, restenosis, psoriasis, graft rejection, arthritis, multiple sclerosis, inflammatory bowel disease, polycystic kidney disease, asthma, autoimmune disorders, hypertrophic diseases, cutaneous fibrosis and vascular lesions.

As used herein, "inflammation" refers to a response to injury that involves the recruitment of cells important for both the destruction of bacterial/viral particles and the stimulation of cellular repair. There tends to be an accumulation of inflammatory cells (i.e. white blood cells such as macrophages, leukocytes, granulocytes) in the affected region.

As used herein, "chemotactic proteins" refers to proteins synthesized and secreted by cells that induce migration of cells towards the region from which the chemotactic agent originates. Smooth muscle cells can produce the protein MCP-1 (monocyte chemotactic protein-1) which stimulates the movement of monocytes from the bloodstream into the vessel where they subsequently differentiate into macrophages.

As used herein, "differentiation" refers to the conversion of a cell from its normal phenotype to one that presents different properties. In the case of vascular smooth muscle, these cells can undergo a reversal, of the differentiation process that led to their formation. This "dedifferentiation" results in the conversion of the cells from a quiescent, contractile phenotype to one characterized by cell proliferation and the synthesis of enzymes required for cell migration (inductive state).

As used herein, "extracellular matrix" refers to the protein network that surrounds all cells and serves as a matrix for their attachment to each other. The ECM is typically composed of collagen, fibronectin and laminin.

As used herein, "effective amount" refers to the administration of an amount of a given compound that achieves the desired effect.

As used herein and as discussed above, "vascular stenosis" refers to vessel wall thickening, clogging or constriction and loss of blood flow. The stresses leading to stenosis may be, for example, mechanical, hypoxia, injury, shear-stress, pharmacological, infectious, inflammatory, oxidative, immunogenic, diabetic or pressure.

As used herein and as discussed above, "angioplasty" refers to procedures and methods involved in the opening or unclogging of blocked arteries. In some instances, angioplasty involves the use of a balloon-tipped catheter which is inserted into the heart's vessels to open partially blocked, or stenotic, coronary arteries. While balloon angioplasty does widen the restricted artery, a significant number of patients have renewed narrowing of the widened segment soon after the procedure. This subsequent narrowing of the artery is called restenosis and can necessitate the repetition of the angioplasty procedure or require alternative treatment such as coronary bypass graft surgery.

Described herein are results indicating that Meta-iodobenzylguanidine (MIBG), a norepinephrine analogue that also belongs to a class of compounds distinguished by a guanidino moiety, has significant anti-differentiation activity that consequently prevents proliferation, migration and inflammation. Specifically, it is shown that MIBG blocks DNA and RNA synthesis and arrests cells irrespective of cell cycle stage without causing cell death. This is very important, as it indicates that MIBG is an effective anti-proliferative and anti-inflammation agent at concentrations that are non-toxic. Specifically, MIBG contains a guanidino group which is acted upon by ADPRT. Thus, MIBG acts as a decoy substrate, preventing ADPRT from acting on its cellular substrates. As a result, ADPRT is unable to carry out its normal functions within the cell, causing the cell to arrest. In an exemplary use of MIBG that is herein described, MIBG is used to prevent and/or inhibit restenosis. Specifically, MIBG in combination with an adhesive agent is applied to the wall of a vessel having undergone recent trauma, for example, balloon angioplasty. As discussed below, MIBG prevents differentiation and proliferation of the smooth muscle cells, thereby preventing restenosis from occurring. Furthermore, the adhesive agent acts to localize MIBG to the site of injury, thereby limiting potential side effects. These results indicate that MIBG has a wide range of potential uses as an anti-proliferative and/or antiinflammation agent, particularly in combination with the adhesive agent, which allows for the delivery and localization of MIBG to the site of interest. It is also important to note that, as discussed herein, MIBG preferentially localizes to fast-growing tissues, meaning that it may also be used in isolation from the adhesive agent. Furthermore, the discovery that an ADPRT decoy substrate can act as an anti-restenosis agent indicates that other ADPRT decoy substrates could be used as anti-restenosis agents or to treat or prevent other injury-related disorders. In this regard, there is described herein an organ culture system for testing the effectiveness of anti-restenosis agents.

To summarize, MIBG has anti-differentiation, anti-proliferation and antiinflammation activities that may be applicable in the treatment of certain diseases, as discussed below. While trials for cancer using MIBG specifically have been reported (as discussed above and in Taal et al, 1996, *Int J Card Imaging* 12: 305–310), it is important to note that MIBG was selected based on its activity as an antimitochondrial agent. In addition, other applications have been overlooked. As discussed herein, MIBG operates as a decoy substrate for ADPRT and prevention of protein ADP-ribosylation inhibits specific processes essential for cell proliferation and differentiation. It is therefore proposed that any compound with similar properties could also be used for this purpose. For example, these include compounds having the general structure:

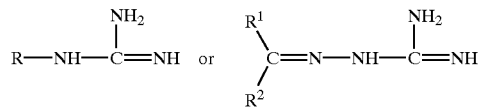

As will be appreciated by one knowledgeable in the art, these include, for example, alkylguanylhydrazones, aminoguanylhydrazones, acetylguanylhydrazones, arylguanylhydrazones, haloarylguanylhydrazones, bis(guanylhydrazones), tris(guanylhydrazones), alkyl guanidines, phenylguanidines, halophenylguanidines, benzylguanidines, aminoguanidines, mercaptylguanidines, thioetheric-guanidines, hydroxy functionalized guanidines, ether functionalized guanidines, amino functionalized guanidines, sulfonic acid functionalized guanidines, 1,3,4-thiadiazole containing guanidines, N-guanidinylamides, pyridine-containing guanidines, naphthalene-containing guanidines, alkyl halide-containing guanidines, aralkyl guanidines, bisguanidines, disubstitued guanidines, N-alkyldiguanidines, Naryldiguanidines, heterocyclic guanidines and carboxylic acid derivatives thereof.

$R$, $R^1$ and $R^2$ may be, independently, for example, H, $CH_3$, $CH_2CH_3$, $CH_2(CH_2)_{1-16}CH_3$, $C(CH_3)_3$, $CH_2C(CH_3)_3$, $CH_2C(CH_3)_3$, $CH(CH_3)CH_2CH_2CH_3$, $CH_2CH(CH_3)$ $CH_2CH_2CH_3$, $CH_2CH(CH_3)CH_2CH_2CH(CH_3)_2$, $C(CH_3)_2$ $CH_2C(CH_3)_3$, $CH_2CH_2CH(CH_3)CH_2C(CH_3)_3$, 5, 6 and 8 member carbon rings, substituted benzene rings, substituted benzyl rings, $CH_2CH_2SH$, $CH_2CH_2CH_2SH$, $CH_2CH_2SCH_3$, $CH_2CH_2SCH_2CH_3$, $CH_2COOH$, $CH_2CH_2COOH$, $CH(CH_3)COOH$, $CH_2(CH_2)_2COOH$, $CH_2(CH_2)_9COOH$, $CH(COOH)CH_2(C_6H_5)$, $CH_2CH_2CH(NH_2)COOH$, $CH_2CH_2CH_2CH(NH_2)COOH$, $CH_2(CH_2)_3CH(NH_2)COOH$, $OCH_2COOH$, $O(CH_2)_2CH(NH_2)COOH$, $CH(COOH)CH_2COOH$, $COOCH_2CH_3$, $CH_2CH_2OCO(C_6H_5)$, $CSNH_2$, $CH_2(CH_2)_3OCONHCH_3$, $CH_2(CH_2)_2OCONH_2$, $CH_2(CH_2)_2NHCOCF_3$, $NHCOCH(Cl)_2$, $CONH_2$, $CH(COOC_2H_5)CH_2OH$, $CH(CH_3)CH_2COOCH_2CH_3$, $NH_2$, $NH(CH_3)$, $OH$, $OCH_3$, $O(CH_2)_2OH$, $O(CH_2)_3OH$, $OC_6H_5$, $O(CH_2)_3C_6H_5$, $CH_2CH_2OH$, $CH_2CH(OH)C_6H_5$, $CH_2(CH_2)_2OH$, $CH_2(CH_2)_3OH$, $CH_2(CH_2)_5OH$, $CH_2CH_2NH_2$, thiadiazoles, COR (wherein R is, for example, H, $CH_3$, $C_6H_5$, $(CH_2)_{1-9}CH_3$ or a substituted benzene ring), pyridine or substituted pyridine, napthalene, substituted naphthalene, sulfonic acid, heterocyclic compounds, substituted phenyl, and phenyl. As will be appreciated by one skilled in the art, the substituents may include any of the above-listed compounds as well as Cl, Br, I, F, COOH, CN, $CF_3$, SH, $SCH_2CH_2$, $NO_2$, H, $CH_3$, $NH_2$, $OCH_3$, $SCH(CH_3)_2$, and combinations thereof at various positions around the ring structure(s).

Examples of such compounds include but are by no means limited to MIBG, NBAG (p-nitrobenzylidine aminoguanidine), GBG (glyoxal bis(guanylhydrazone)), MGAG (methylglyoxyl bis(guanylhydrazone)), MBAG (1,1'-[((methylethanediylidene) dinitro)bis(3-aminoguanidine)]), $CF_3GBG$ (trifluoromethylglyoxal bis (guanylhydrazone)), PhGBG (phenylglyoxal bis (guanylhydrazone)), dodine (dodecylguanidine monoacetate), NAP (1-(1-napthylmethyl)guanidine), NBGH (o-nitrobenzylguanylhydrazone), GAA (guanidoacetic acid), GPA (3-guanidinoproprionic acid), GBA (4-guanidinobutanoic acid), arginine, MG (methyl guanidine), agmatine, creatine, synthalin A, synthaline B and hirudonine.

In some embodiments, the ADPRT decoy substrate may in fact be a combination of two or more ADPRT decoy substrates.

ADPRT decoy substrates described herein may be synthesized using methods known in the art, see, for example, Wielend et al, 1980, *Nucl. Med.* 21 349–353; Hadrich, et al, 1999, *Med. Chem.* 42, 3101–3108; Short et al, 1963, *J Med. Chem.* 6, 275–283; and Soman et al, 1986, *Biochemistry* 25, 4113–4119.

In some embodiments, the ADPRT decoy substrate may be combined with other compounds or compositions known in the art such that the ADPRT decoy substrate is in the form of, for example, an ointment, pill, tablet, cream, suppository, lotion, gel, foam, film, barrier, wrap, paste or coating using means known in the art and as discussed below. Preferably, such films, wraps or barriers are generally less than 5, 4, 3, 2 or 1 mm thick. In some embodiments, the film may be less than 0.75 mm or 0.5 mm thick. Preferably, the films have good tensile strength and good adhesive properties.

It is of note that the ADPRT decoy substrate discussed above may be prepared to be administered in a variety of ways, for example, topically, orally, intravenously, intramuscularly, subcutaneously, intraperitoneally, intranasally or by local or systemic intravascular infusion using means known in the art and as discussed below.

It is of note that as discussed herein, the ADPRT decoy substrate may be arranged to be delivered at a dosage of about 0.01 to about 0.50 mg per kg of the subject. In other embodiments, the dosage may be about 0.04 to about 0.50 mg per kg of the subject. Alternatively, the dosage may be approximately 0.04 to about 0.2 mg per kg of the subject. In other embodiments, the dosage may be about 0.11 to about 0.2 mg per kg of the subject. Yet further, the dosage may be about 0.11 to about 0.16 mg per kg of the subject. As will be apparent to one knowledgeable in the art, the total dosage will vary according to the weight of the individual. As will be appreciated by one knowledgeable in the art, depending on the molecular weight of the ADPRT decoy substrate, this corresponds to a dosage concentration of approximately 5 mM to about 1 M. Alternatively, the concentration may be about 5 mM to about 400 mM. Furthermore, the concentration may be 10 mM to 400 mM. In other embodiments, the ADPRT decoy substrate is arranged to reside in a localized area at an effective concentration of approximately 5 uM to about 1 mM. Alternatively, the concentration may be about 5 uM to about 400 uM. Furthermore, the concentration may be about 10 uM to about 400 uM. Yet further, the concentration may be about 25 uM to about 400 uM.

In some embodiments, the ADPRT decoy substrate at concentrations or dosages discussed above may be combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly (caprolactone), celluloses, albumin, starch, casein, dextran, polyesters, ethanol, mathacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches. See, for example, *Remington: The Science and Practice of Pharmacy,* 1995, Gennaro ed.

As will be apparent to one knowledgeable in the art, specific carriers and carrier combinations known in the art may be selected based on their properties and release characteristics in view of the intended use. Specifically, the carrier may be pH-sensitive, thermo-sensitive, thermo-gelling, arranged for sustained release or a quick burst. In some embodiments, carriers of different classes may be used in combination for multiple effects, for example, a quick burst followed by sustained release.

"As discussed herein, in one embodiment, the ADPRT decoy substrate is combined with an adhesive agent. As a result of this arrangement, the ADPRT decoy substrate can be localized to the intended area, for example, a damaged vessel, thereby limiting side effects. As will be appreciated by one knowledgeable in the art, the adhesive agent is non-toxic. In one embodiment, MIBG is suspended in a non-toxic, biodegradable fibrin glue (Grecto et al, 1991, *J Biomed Mater Res* 25:39–51; Zilch and Lambiris, 1986, *Arch Orthop Trauma Surg* 106:36–41), which consists of separate fibrinogen and thrombin components purified from human or bovine plasma (Senderoffet al, 1991, *J Parenteral*

Sci Technol 45:2–6; Katz and Spera, 1998, Medical Device and Diagnostic Industry Magazine, April). One example of a fibrin glue is Tisseel™ (Immuno AG, Vienna, Austria). In addition to Tisseel, adhesive biomaterials are being manufactured by Thermogenesis (Rancho Cordova, Calif.), Fusion Medical Technologies, Inc. (Mountain View, Calif.), and CryoLife, Inc. (Kennesaw, Ga.), which offers photoactivated fibrin sealants. V.I. Technologies (New York City) is developing a fibrin sealant similar to Tisseel, as are Haemacure Corp. (Sarasota, Fla.), Convatec/Bristol-Myers Squibb (Skilhman, N.J.), and BioSurgical Corp. (Pleasanton, Calif.). Also applicable are conventional hemostatic agents that work on various stages of the coagulation cascade; for example, agents such as Surgicelg®, Gelfoam®, and Avitene® activate the first stage of the coagulation pathway. Hydrogels can also be used for this application (Dagani, 1997 Chemical & Engineering News, Jun. 9, 1997). Finally, the glue produced by mussels has received interest for bonding materials (Morgan, 1990, *The Scientist 4* (April 30):1). It has been found equal or better to fibrin glue (Pitman et al, 1989, *Bull Hosp Jt Dis Orthop Inst* 49:213–20), and is capable of attaching molecules as small as proteins to a surface (Burzio et al, 1996, *Anal Biochem.* 241:190–4). This mixture can be applied externally onto the vessel. It is of note that fibrin glues have been successfully used to deliver growth factors to promote angiogenesis (Fasol et al, 1994, *J Thorac Cardiovasc Surg* 107: 1432–1439) or inhibit intimal hyperplasia (Zarge et al, 1997, *J Vasc Surg* 25: 840–848), and to deliver antibiotics in vitro (Greco et al, 1991, *J Biomed Mater Res* 25: 39–51). This approach allows for the delivery of pharmacologically potent concentrations locally, without any significant release of the drug systemically. It is of note that other suitable biocompatible or biodegradable adhesives known in the art may also be used. Furthermore, the ADPRT decoy substrate is arranged to be delivered at a local concentration as described above.

In yet other embodiments, the ADPRT decoy substrate may be contained within or adapted to be released by a surgical or medical device, for example, stents, catheters, prostheses, sutures and the like. In these embodiments, the ADPRT decoy substrate at concentrations or dosages described above may be incorporated into nylon microcapsules and applied to the surface of the stent or device. Alternatively, the device may be coated with a film composed of, for example, cellulose, hyaluronic acid, chitosan, ethylene vinyl acetate, or poly lactic acid, impregnated with the ADPRT decoy substrate. Yet further, the device may be coated with a thermo-sensitive gel such that the ADPRT decoy substrate is released when the device is implanted.

Typically, stents are used to expand the lumen of a body passageway. This involves inserting the stent into the passageway such that the passageway is expanded. In general, a preinsertion examination, for example, either a diagnostic imaging procedure or direct visualization at the time of surgery is performed to determine the appropriate location for stent insertion. First, a guide wire is advanced through the proposed site of insertion. A delivery catheter is then passed over the guide wire, allowing insertion of the catheter into the desired position. The stent is then expanded by means known in the art.

The stent may be coated for example by spraying or dipping the stent with or in the ADPRT decoy substrate described above, or the stent may be coated with an absorption-promoting substance, such as hydrogel, first. Alternatively, the stent may be surrounded in a sleeve, mesh or other structure impregnated with the ADPRT decoy substrate and arranged to release the ADPRT decoy substrate over time.

In other embodiments, an ADPRT decoy substrate at concentrations or dosages described above may be encapsulated for delivery. Specifically, the ADPRT decoy substrate may be encapsulated in biodegradable microspheres, microcapsules, microparticles, or nanospheres. The delivery vehicles may be composed of, for example, hyaluronic acid, polyethylene glycol, poly(lactic acid), gelatin, poly(E-caprolactone), or a poly(lactic-glycolic) acid polymer. Combinations may also be used, as, for example, gelatin nanospheres may be coated with a polymer of poly(lactic-glycolic) acid. As will be apparent to one knowledgeable in the art, these and other suitable delivery vehicles may be prepared according to protocols known in the art and utilized for delivery of the ADPRT decoy substrate. In some embodiments, the delivery vehicle may be coated with an adhesive for localizing the ADPRT decoy substrate to the area of interest. Alternatively, the delivery vehicle may be suspended in saline and used as a nanospray for aerosol dispersion onto an area of interest. Furthermore, the delivery vehicle may be dispersed in a gel or paste, thereby forming a nanopaste for coating a tissue or tissue portion.

It is of note that the ADPRT decoy substrates as described above may be combined with permeation enhancers known in the art for improving delivery. Examples of permeation enhancers include, but are by no means limited to those compounds described in U.S. Pat. Nos. 3,472,931; 3,527,864; 3,896,238; 3,903,256; 3,952,099; 4,046,886; 4,130,643; 4,130,667; 4,299,826; 4,335,115; 4,343,798; 4,379,454; 4,405,616; 4,746,515; 4,788,062; 4,820,720; 4,863,738; 4,863,970; and 5,378,730; British Pat. No. 1,011,949; and Idson, "1975, J. Pharm. Sci. 64:901–924.

In some embodiments, the ADPRT decoy substrate in any suitable form as described above, may be combined with biological or synthetic targetting molecules, for example, site-specific binding proteins, antibodies, lectins or ligands, for targetting the ADPRT decoy substrate to a specific region or location.

As discussed above, the ADPRT decoy substrates inhibit cell proliferation, migration and differentiation. As such, ADPRT decoy substrates are suitable treatments for other disorders characterized by these processes, for example, injury-related disorders.

As discussed above, asthma is characterized by recurring airway obstruction involving smooth muscle cell proliferation and inflammatory cell infiltration. Given that ADPRT decoy substrates inhibit monocyte and smooth muscle cell differentiation, these substrates would likely lessen the severity of asthma attacks. That is, the ADPRT decoy substrate would accomplish one or more of the following: decrease the severity of or ameliorate symptoms, decrease the duration of attacks, increase the frequency and duration of remission periods, prevent chronic progression of dyspnea, coughing and wheezing, improve hypoxia, increase forced expiration volume in one second, and improve resistance to airflow and hypocapnea/respiratory alkalosis. In embodiments for treating asthma, the ADPRT decoy substrate may be arranged to be inhaled, for example, in a spray form, the preparation of which is described herein.

As discussed above, polycystic kidney disease is believed to be caused by proliferation of epithelial cells in tubule segments within the kidney. Given that the ADPRT decoy substrates inhibit cell proliferation, these compounds could also be used as a treatment for polycystic kidney disease. In these embodiments, the ADPRT decoy substrate may be injected or taken as a tablet or pill form. As discussed above, the ADPRT decoy substrates preferentially localize to fast-growing cells, meaning that the ADPRT decoy substrate is taken up where it is needed and will inhibit proliferation of the epithelial cells in the kidney, which will in turn reduce the severity of the disease. Specifically, the ADPRT decoy substrate will accomplish one or more of the following: ameliorating symptoms associated with the disease, prolong remission, reduce fluid accumulation, lessen inflammation, reduce the rate of cyst formation, reduce size of cysts, and/or reduce or ease kidney enlargement, As discussed above, skin diseases, such as psoriasis, are characterized by rapid skin growth followed by inflammation. As discussed above, ADPRT decoy substrates inhibit cell proliferation and migration of the inflammatory system cells as well as their differentiation, meaning that the ADPRT decoy substrates are effective treatments for skin diseases. In these embodiments, the ADPRT decoy substrates would be arranged for topical administration and may in some embodiments include permeation enhancers, as discussed above. In these embodiments, application of the ADPRT decoy substrate to the afflicted area will inhibit rapid skin growth, thereby diminishing the severity of the symptoms. Specifically, the ADPRT decoy substrate will accomplish at least one of the following: reduction in the number and/or size of skin lesions, lessening of cutaneous symptoms, for example, pain, burning and bleeding of the affected skin, inhibiting keratinocyte proliferation, and reducing skin inflammation.

As discussed above, multiple sclerosis is a chronic neurological disorder that affects the nervous system. Specifically, cell migration of a macrophage-like activity is involved in the destruction of the myelin. As discussed above, the ADPRT decoy substrates have been shown to prevent monocyte differentiation into macrophages and migration, meaning that ADPRT decoy substrates would inhibit demyelination, thereby reducing severity of the disease. That is, the ADPRT decoy substrate would accomplish at least the following: decrease the severity of symptoms, decrease the duration of disease exacerbations, increase the frequency and duration of disease remission and/or symptom free periods, prevent or attenuate chronic progression of the disease, improve visual symptoms, improve gait disorders, such as, weakness, axial instability, sensory loss, spasticity, hyperreflexia and/or loss of dexterity, improve cognitive impairment, reduce myelin loss, reduce breakdown of the blood-brain barrier and reduce perivascular infiltration of mononuclear cells. In these embodiments, the ADPRT decoy substrate may be ingested as a tablet or pill, applied topically or injected, prepared at appropriate concentrations or dosages as described herein.

Similarly, inflammatory bowel diseases are caused by intestinal inflammation and repeated inflammatory responses. As discussed above, the ADPRT decoy substrates prevent migration and differentiation of inflammatory cells, meaning that the ADPRT decoy substrates would also be an effective treatment for these disorders. That is, injection or infusion of the ADPRT decoy substrates into the bowel or intestine will inhibit migration of cells of the inflammatory system, thereby reducing the severity of the disease. Specifically, the ADPRT decoy substrate would accomplish at least one of the following: decrease the frequency of the attacks, increase the duration of remission periods, decrease the severity or duration of abscess formation, intestinal obstruction, intestinal perforation and the like as well as ameliorate or reduce symptoms such as bloody diarrhea, abdominal pain, fever, weight loss and abdominal distension.

As discussed above, arthritis is believed to be an autoimmune disease, characterized by infiltration of the joints with inflammatory system cells. As such, ADPRT decoy substrates inhibit cell migration and differentiation, indicating that these compounds would be an effective treatment for arthritis. Specifically, the ADPRT decoy substrate will accomplish at least one of the following: decrease severity of symptoms, including pain, swelling and tenderness of affected joints, weakness and fatigue, decrease severity of clinical signs, including thickening of the joint capsule, synovial hypertrophy, decreased range of motion, fixed joint deformity and soft tissue contractures, increase the frequency and duration of remission or disease-free periods and prevent or attenuate chronic progression of the disease. In these embodiments, the ADPRT decoy substrate is arranged to be injected directly into the afflicted joints or taken orally. Preparation of the ADPRT decoy substrates for injection is described herein.

Furthermore, it is known that there are inflammatory and proliferative components that contribute to the development of an arteriosclerotic lesion. For this reason, an ADPRT decoy substrate should be able to restrict progression of this condition, that is, reduce the incidence and severity of the lesions. Furthermore, the incidence or severity of symptoms associated with all vascular procedures involving grafting, puncturing or producing intimal damage can be reduced by the abovedescribed compounds, as could inflammation and/or irritation accompanying valve replacements, catheters, prosthesis, implanted devices, pacemakers, nerve stimulators, patches, organ transplants, small vessel vaculopathy, wound repair, or psoriasis. Thus, the symptoms associated with any inflammation or inflammatory disease that is localized to a defined region can be ameliorated using the ADPRT decoy substrates described above. In these embodiments, the ADPRT decoy substrate may be localized through the use of an adhesive, impregnated mesh or targeting molecule as described herein, or the device or organ may be coated or infused with the ADPRT decoy substrate as described herein.

ADPRT decoy substrates could also be sprayed or applied to tissue grafts or organs prior to transplantation. As discussed above, the ADPRT decoy substrates inhibit cell migration and differentiation, meaning that prior application of the ADPRT decoy substrates would inhibit rejection of the transplanted material. Specifically, graft rejection is characterized by lesion formation, inflammation and necrosis. The ADPRT decoy substrate will accomplish at least one of the following: prolong the life of the graft; decrease the side effects associated with immunosuppressive therapy and decrease accelerated atherosclerosis associated with transplants. In other embodiments, a mesh coated or arranged to release the ADPRT decoy substrates may be used in lieu of spray application. Alternatively, the sprays or meshes could also be used to treat, for example, venous leg ulcers, skin grafts, post-operative hypertrophy, hyperplasia, hypertrophic burn scars, hypertrophic gastropathy, cardiac hypertrophy associated with congestive heart failure and hypertrophic cardiopathy, or hypertension. For example, hypertension is an increase in smooth muscle cell volume within a blood vessel due to excessive pressure, lack of oxygen/nutrients or enhanced production of hypertrophy-inducing factors released as a result of trauma distinct from the site of action (for example, kidney disease). Also, hypertrophic cardiac disease (for example, congestive heart failure, hypertrophic cardiomyopathy, valve replacement surgery) results from an increase in cardiomyocyte volume as a result of hypoxia, surgical intervention or genetic defect. Cellular hypertrophy and inflammation occur in the region affected by the causative factor. Thus, these disorders also require cell migration and differentiation, meaning that the ADPRT decoy substrate may alleviate some of the associated symptoms.

As discussed above, the ADPRT decoy substrates are clearly acting as anti-differentiation agents. In this manner, these compounds target the earliest alteration of a process and therefore also have anti-proliferation, anti-inflammation and anti-fibrosis effects.

The invention provides kits for carrying out the methods of the invention. Accordingly, a variety of kits are provided. The kits may be used for any one or more of the following (and, accordingly, may contain instructions for any one or more of the following uses): treating arteriosclerosis, restenosis, inflammatory bowel diseases, polycystic kidney diseases, asthma, graft rejection, cutaneous fibrosis, hypertrophic disease, rheumatoid arthritis or the like in an individual, preventing an autoimmune response, vascular constriction, swelling, pain, inflammation, prolonged inflammatory response or rapid cell or tissue growth in an individual at risk of arteriosclerosis, restenosis, inflammatory bowel diseases, polycystic kidney diseases, asthma, graft rejection, cutaneous fibrosis, hypertrophic disease, rheumatoid arthritis or the like; preventing one or more symptoms of an autoimmune response, vascular constriction, swelling, pain, inflammation, prolonged inflammatory response or rapid cell or tissue growth or the like in an individual at risk of arteriosclerosis, restenosis, inflammatory bowel diseases, polycystic kidney diseases, asthma, graft rejection, cutaneous fibrosis, hypertrophic disease, rheumatoid arthritis or the like; reducing severity one or more symptoms of an autoimmune response, vascular constriction, swelling, pain, inflammation, prolonged inflammatory response or rapid cell or tissue growth in an individual; reducing recurrence of one or more symptoms of an autoimmune response, vascular constriction, swelling, pain, inflammation, prolonged inflammatory response or rapid cell or tissue growth in an individual; suppressing an autoimmune response, vascular constriction, swelling, pain, inflammation, prolonged inflammatory response or rapid cell or tissue growth in an individual at risk of arteriosclerosis, restenosis, inflammatory bowel diseases, polycystic kidney diseases, asthma, graft rejection, cutaneous fibrosis, hypertrophic disease, rheumatoid arthritis or the like; delaying development of an autoimmune response, vascular constriction, swelling, pain, inflammation, prolonged inflammatory response or rapid cell or tissue growth and/or a symptom of arteriosclerosis, restenosis, inflammatory bowel diseases, polycystic kidney diseases, asthma, graft rejection, cutaneous fibrosis, hypertrophic disease, rheumatoid arthritis or the like in an individual; reducing duration an autoimmune response, vascular constriction, swelling, pain, inflammation, prolonged inflammatory response or rapid cell or tissue growth in an individual.

The kits of the invention comprise one or more containers comprising an ADPRT decoy substrate, a suitable excipient as described herein and a set of instructions, generally written instructions although electronic storage media (e.g., magnetic diskette or optical disk) containing instructions are also acceptable, relating to the use and dosage of the ADPRT decoy substrate for the intended treatment (e.g., arteriosclerosis, restenosis, inflammatory bowel diseases, polycystic kidney diseases, asthma, graft rejection, cutaneous fibrosis, hypertrophic disease, rheumatoid arthritis or the like) . The instructions included with the kit generally include information as to dosage, dosing schedule, and route of administration for the intended treatment. The containers of the ADPRT decoy substrate may be unit doses, bulk packages (e.g., multi-dose packages) or sub-unit doses.

The ADPRT decoy substrate of the kit may be packaged in any convenient, appropriate packaging. For example, if the composition is a freeze-dried formulation, an ampoule with a resilient stopper is normally used, so that the drug may be easily reconstituted by injecting fluid through the resilient stopper. Ampoules with non-resilient, removable closures (e.g., sealed glass) or resilient stoppers are most conveniently used for injectable forms of the ADPRT decoy substrate. Also, prefilled syringes may be used when the kit is supplied with a liquid formulation of the ADPRT decoy substrate. The kit may contain the ADPRT decoy substrate in an ointment for topical formulation in appropriate packaging. Also contemplated are packages for use in combination with a specific device, such as an inhaler, nasal administration device (e.g., an atomizer) or an infusion device such as a minipump.

The following Examples are provided to illustrate, but not limit, the invention.

EXAMPLE I

Effect of the MIBG on RNA and DNA Synthesis in H4IIE Hepatoma Cells

Figure 2:
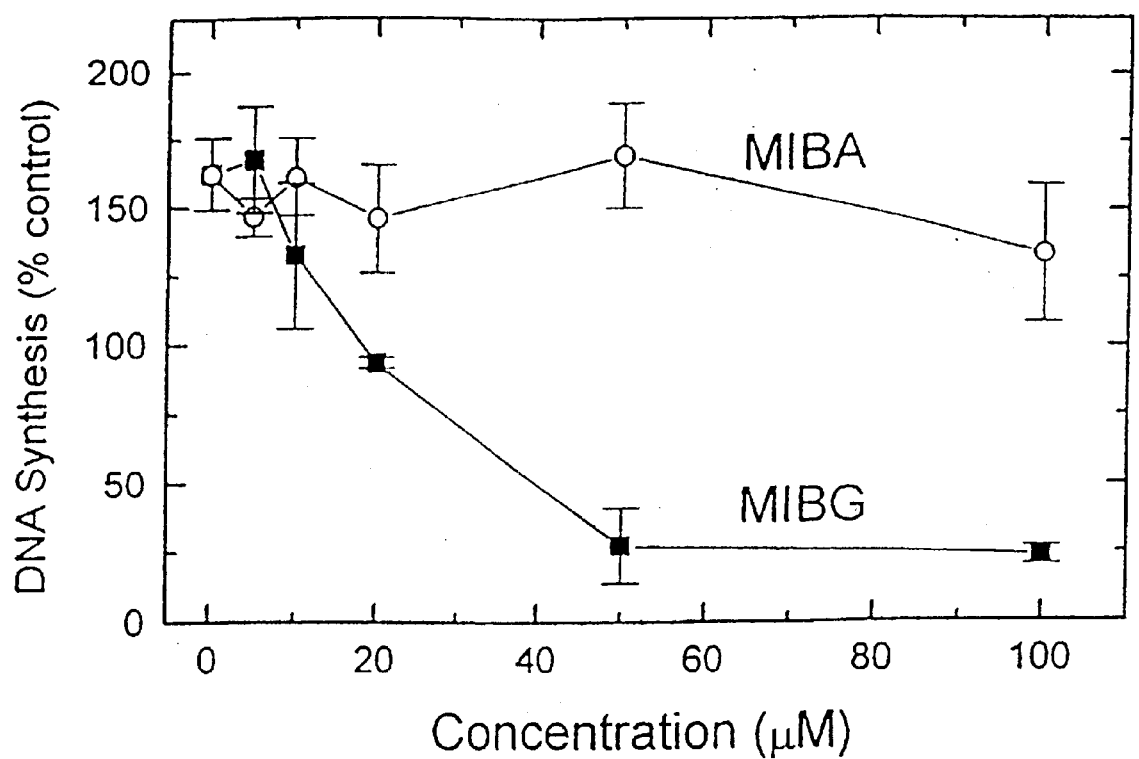
FIG. 2 is a graph showing the effect of varying concentrations of MIBG and MIBA on DNA synthesis.

Incorporation of uridine or thymidine was used to define the change in rate of DNA and RNA synthesis, respectively, in response to a mitogen such as insulin. Specifically, quiescent H4IIE cells were prepared by placing the cultures (in 24-well dishes) into serum-free a-minimal essential medium for 3 days. It is of note that the normal growth media for H4IIE cells is α-MEM containing 10% fetal bovine serum (FBS). After reaching quiescence, the cells were stimulated with 1 μM insulin and incubated for either 6 hours or 24 hours in the presence of 1 μCi/ml $^3$H-uridine or $^3$H-thymidine, respectively. Cells were subsequently lysed with detergent and the nucleic acids precipitated with 5% trichloroacetic acid. The precipitated material was collected on glass fibre filters and the radioactive content measured by scintillation counting. Initial comparisons with 3-aminobenzamide indicated that MIBG was a more potent inhibitor of cell growth, as indicated by RNA synthesis in response to insulin, as shown in FIG. 1. The ability of MIBG to inhibit DNA synthesis was also tested and is shown in FIG. 2. As can be seen, MIBG inhibits DNA synthesis whereas the MIBG analogue MIBA (meta-iodobenzylamine), which is lacking a guanidino group, does not inhibit DNA synthesis. Furthermore, while complete inhibition of DNA synthesis by MIBG is obtained at approximately 20 μM, higher concentrations decrease basal DNA synthesis below control levels. From these data, it is clear that MIBG inhibits the stimulation of RNA and DNA synthesis in response to insulin. This in turn indicates that MIBG is a potent anti-proliferation agent.

EXAMPLE II

Effect Of MIBG On Cell Number H4IIE Hepatoma Cells

Figure 3:
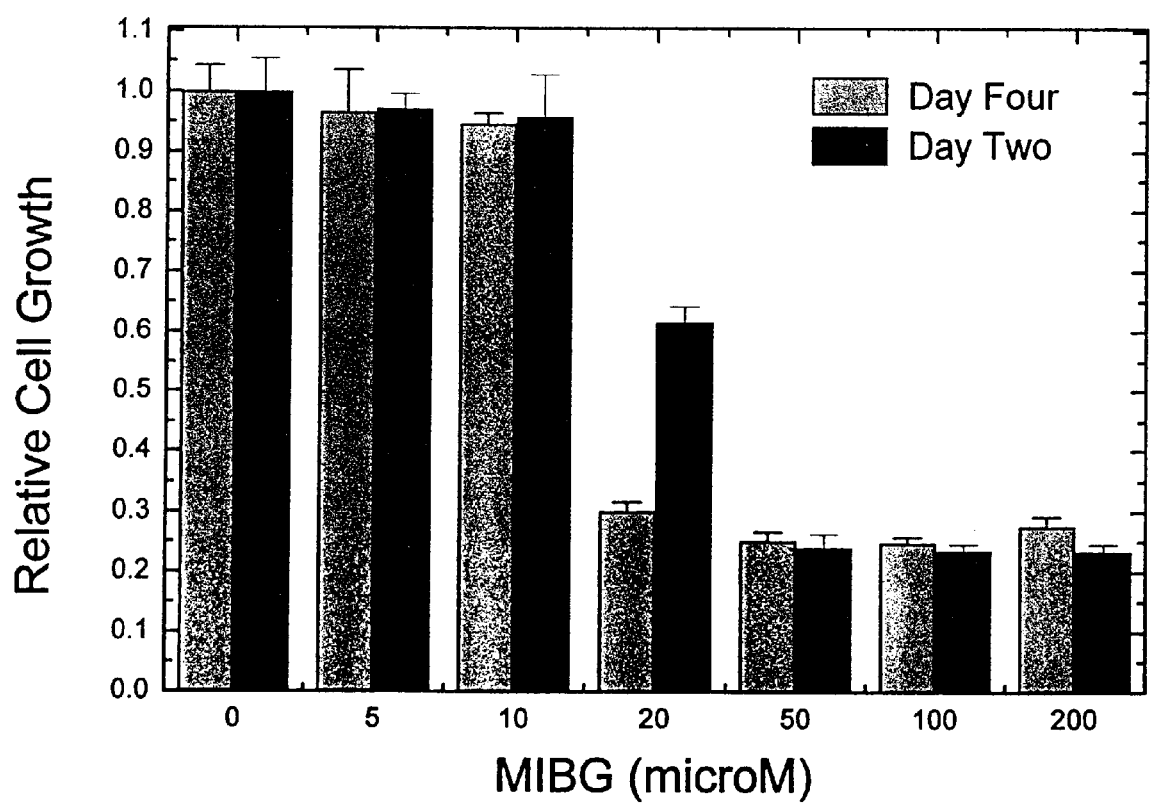
FIG. 3 is a bar graph showing the effect of MIBG on relative cell growth in H4IIE cells at two and four days after plating.

Confirmation that MIBG inhibits cell proliferation was obtained with a separate assay that involves staining viable cells with MTT [3-(4,5-dimethylthiozol-2-yl)-2,5-diphenyltetrazolium bromide], following the protocol described by Saward and Zahradka, 1997, *Circ Res* 81: 249–257, which is incorporated herein by reference. In this assay, H4IIE cells are plated on 96-well dishes, and incubated in standard growth medium. Separate plates were prepared for comparing the effects of MIBG after 2 or 4 days. At those time points, 200 μl of 5 mg/ml MTT was added to each well, and the cells were incubated an additional 4 hours. The medium was removed and cells were treated with acidified isopropanol and the absorbance read at 570 nm. Increased absorbance is indicative of increases in cell number. The results obtained in this experiment are shown in FIG. 3, wherein it is demonstrated that MIBG at 20 µM was effective in preventing increases in cell number. It is of note that at 200 µM MIBG, staining remains at 60% of control values, which indicates that cell death does not occur if cells are exposed to MIBG for up to 96 hours. This experiment therefore shows that while MIBG prevents cell proliferation, MIBG is not lethal to cells.

EXAMPLE III

Flow Cytometry of H4IIE Hepatoma Cells Treated with MIBG

Additional verification that MIBG blocked cell proliferation was obtained using flow cytometry analysis. Proliferating H4IIE cells (<40% confluent) were incubated for 48 hours in the presence or absence (untreated control or containing MIBA) of 25 µM MIBG. The cells were pulse labeled with bromodeoxyuridine (BrdU) 2 hours before harvest to label replicating DNA. Cells were released by trypsinization, collected by centrifugation and permeabilized with Triton X-100 (1%). Replicated DNA was labeled with an anti-BrdU antibody conjugated to FITC (fluorescein isothiocyanate), while total DNA was labeled with propidium iodide. The FITC and propidium iodide labels were detected at 514 nm and 600 nm, respectively, with a Coulter flow cytometer™ (excitation wavelength 488 nm), and number of cells containing these fluors were quantified. The data were plotted as cells with propidium iodide versus cells with BrdU. In the control cell population (no treatment over 48 hours), there is evidence of DNA synthesis as indicated by incorporation of bromodeoxyuridine, (y-axis of FIG. 4A), and demonstrated by the presence of cells within the boxed area in FIG. 4A. In contrast, no bromodeoxyuridine incorporation is observed in the presence of MIBG, as shown in FIG. 4B. That is, there are no cells present in the boxed area, indicating that DNA synthesis is not occurring in cells treated with MIBG. Furthermore, it is of note that the results obtained with MIBA (not shown) were identical to those observed in the control cells. To summarize, the results described above indicate that MIBG is a potent inhibitor of cell proliferation. Furthermore, the cellular process affected by MIBG is active throughout the cell cycle. This conclusion is based on the fact that there is no accumulation of cells at a specific phase of the cell cycle. In addition, it is of note that there is no apparent decrease in cell number or an increase in smaller cells, both characteristics of cell death.

EXAMPLE IV

MIBG Toxcity on H4IIE Cells

To address the issue of MIBG toxicity, lactate dehydrogenase (LDH) release was measured after incubation with MIBG or MIBA. Quiescent H4IIE cells were prepared in 96-well dishes and treated with various concentrations of either MIBG or MIBA for 96 hours. To quantify the release of LDH from the cells, which only occurs if the cells are damaged or killed by the treatment, 100 µl of culture medium was transferred to a fresh dish. To this was added 100 µl of dye/catalyst mixture (Boehringer Mannheim cytotoxicity detection kit™), and the samples were subsequently incubated for 30 minutes at 37° C. Absorbance of the solution was monitored at 490 nm. The colour intensity indicates the relative LDH content in the test samples. That is, as shown in FIG. 5, increased LDH release is detectable at a concentration of 50 µM MIBG, which is higher that the 20 µM MIBG capable of blocking cell proliferation, discussed above. Furthermore, it is of note that no increase in LDH was observed with MIBA below 200 µM. Taken in isolation, this observation suggests that MIBG is toxic to the cells when present in concentrations higher than 50 µM. However, it is important to note that as discussed above, there is no concomitant change in cell number, and microscopic observation indicates that the cells do not show significant morphological change. As a consequence, it is speculated that changes in LDH release may be coupled to non-toxic and reversible alterations in mitochondrial metabolism or membrane integrity as a result of MIBG treatment.

EXAMPLE V

Effect of MIBG on Friend and L6 Cell Differentiation

Figure 32:
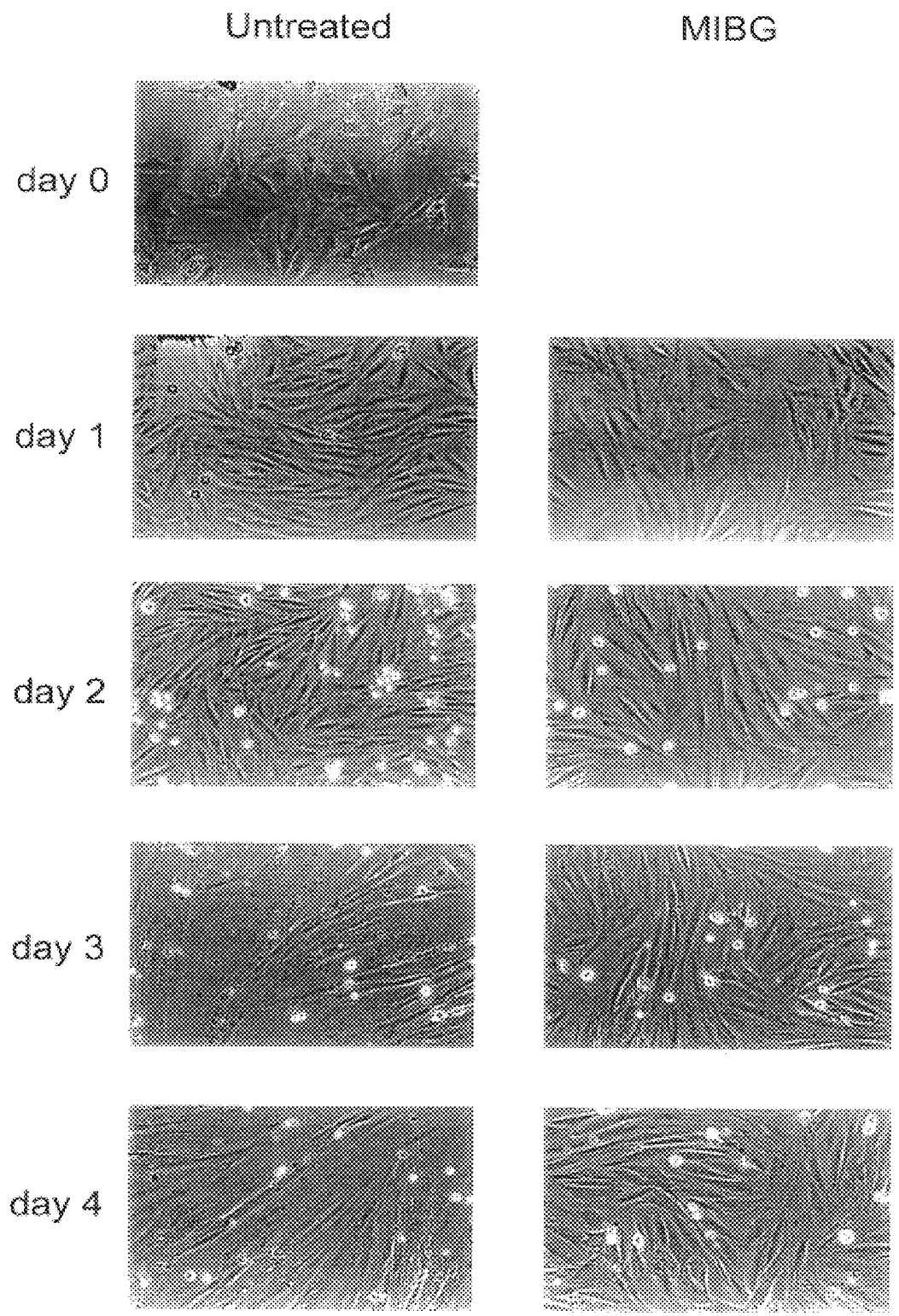
FIG. 32: Inhibition of L6 myoblast differentiation by MIBG. Proliferating L6 myoblasts, maintained in media containing 10% fetal bovine serum, were placed into media containing 2.5% horse serum±MIBG (25 $\mu$M). These conditions initiate the differentiation program leading to cell fusion and formation of myotubes. Cells were photographed daily over 4 days.

The effect of MIBG and 3-aminobenzamide on Friend cell differentiation was examined. The data show that MIBG prevents differentiation, which in turn implicates mono (ADP-ribosyl)ation in differentiation. It is of note however that MIBG acts at a point in the differentiation pathway that is distinct from 3-aminobenzamide. Specifically, MIBG inhibits Friend cell differentiation following commitment, whereas 3-aminobenzamide inhibits the commitment phase. A similar conclusion was reached with the L6 myoblast system (see FIG. 32), which recapitulates skeletal muscle differentiation. In this instance, MIBG inhibits differentiation of L6 myoblasts at an early stage, presumably by preventing the expression of the essential myogenic factor myogenin.

EXAMPLE VI

Effect of MIBG on DNA and RNA Synthesis in Smooth Muscle Cells

Smooth muscle cells were prepared for primary culture from porcine coronary arteries. The explant procedure used was as described in Saward and Zahradka, 1997, *Mol Cell Biochem* 176: 53–59, which is incorporated herein by reference. These cells proliferate in the presence of fetal bovine serum, and enter a quiescent state when placed into a serum-free, supplemented medium. Under these conditions, the cells remain in a responsive state for up to 7 days, but experiments are typically carried out with 5-day quiescent cells. In the presence of mitogens, quiescent smooth muscle cells begin to synthesize RNA and protein and, within 48 hours, initiate DNA synthesis (Saward and Zahradka, 1997, *Mol Cell Biochem* 176: 53–59). Depending upon the mitogen used, the cells eventually divide. Thus, increased DNA synthesis is used to demonstrate stimulation of the cells; however, increased cell number defines proliferation. A number of mitogens have been tested, and while serum is the most potent, bradykinin, insulin-like growth factor-1, platelet-derived growth factor, prostaglandin E2 and angiotensin II, to name a few, may also be used.

To demonstrate that MIBG inhibits smooth muscle cell proliferation, quiescent smooth muscle cells were treated with angiotensin II and serum. The stimulation of DNA and RNA synthesis, as determined by incorporation of thymidine or uridine, respectively, according to the protocol described above, showed that stimulation by both mitogens was inhibited with MIBG at concentrations of 20 to 50 μM, as shown in FIGS. 6 and 7. It is of note that MIBG has a similar effect on stimulation by bradykinin and prostaglandin E2 (data not shown). Furthermore, it is of note that MIBG alone inhibits DNA synthesis below basal levels, as shown in FIG. 8, and that the decrease does not exceed 40% of the control at the highest concentration tested. Thus, cell death does not account for the decline in basal DNA synthesis rate. In fact, the constant values seen between MIBG concentrations of 50 and 200 μM concur with the LDH release data obtained with H4IIE cells, shown in FIG. 5 and discussed above. These results are consistent with the conclusion that MIBG effectively blocks smooth muscle proliferation, in accordance with a previous report (Thyberg et al, 1995, *Differentiation* 51:388–392) and that MIBG is not cytotoxic at the levels below 200 μM.

EXAMPLE VII

Effect of MIBG on Human Smooth Muscle Cells

Figure 26:
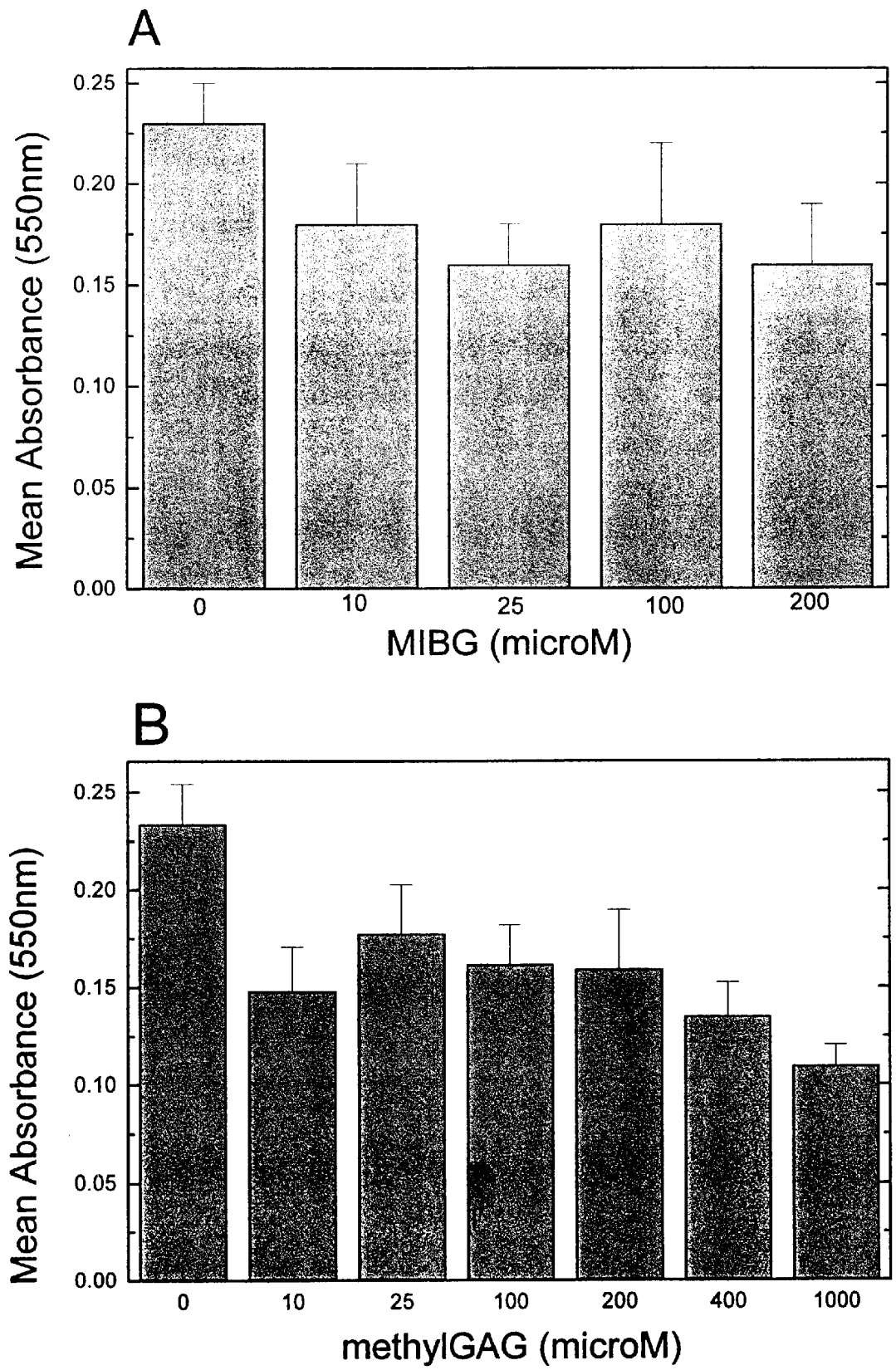
FIG. 26 is a bar graph showing the evaluation of MIBG and methylGAG cytotoxicity on human smooth muscle cells.

It is of note that similar results, including measurement of DNA synthesis and cytotoxicity, have been obtained with smooth muscle cells derived from human arterial conduits, as shown in FIG. 26A. Specifically, in this example, smooth muscle cells were prepared from explants of human internal mammary artery, radial artery and saphenous vein segments obtained during coronary bypass surgery. These data indicate that MIBG has comparable effects in both porcine and human tissues.

EXAMPLE VIII

Effect of MIBG on Smooth Muscle Cell Migration

Figure 17:
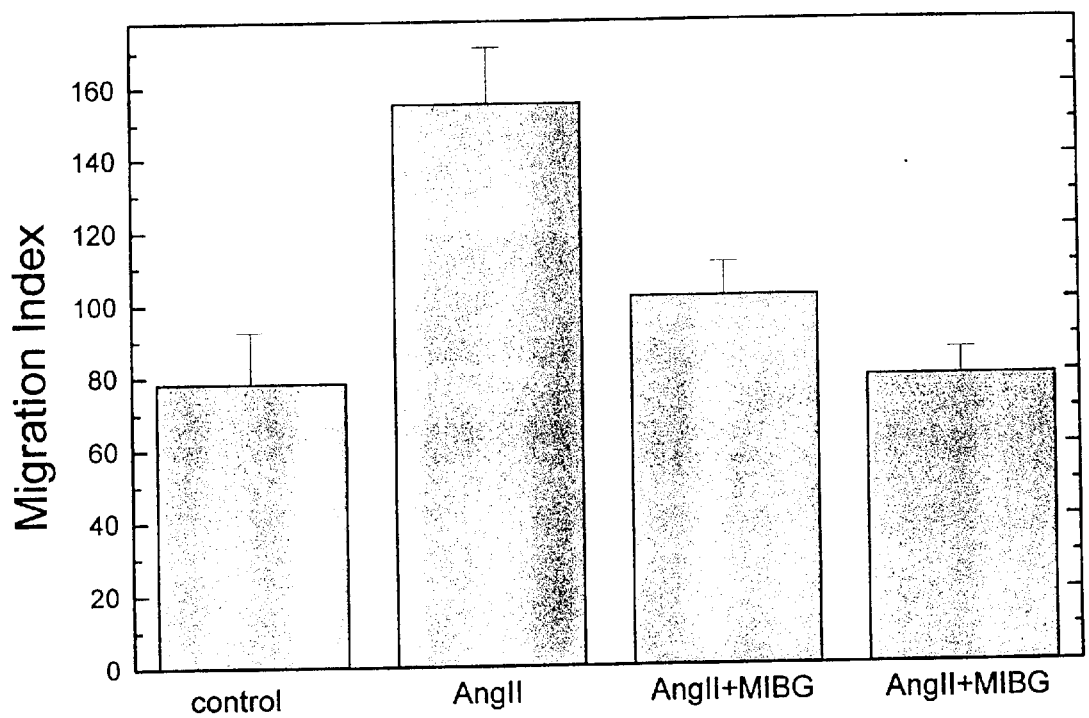
FIG. 17 is a bar graph showing the effect of MIBG and methylGAG on smooth muscle cell migration.

In addition, the effect of MIBG on smooth muscle cell migration was examined, as evidence presented herein suggests that MIBG inhibits the dedifferentiation of smooth muscle cells, an event that precedes the advent of cell proliferation. Specifically, smooth muscle cells were seeded into the upper chamber of a Boyden chamber, which consists of two compartments that are separated by a permeable membrane. The lower compartment contained 10 μM Angiotensin II, a chemoaftractant that stimulates migration of the smooth muscle cells through the pores of the membrane separating the compartments. As can be seen in FIG. 17, inclusion of 20 μM MIBG or methylGAG in the medium of the Boyden chamber inhibited smooth muscle cell migration in response to Angiotensin II. Specifically, migration to the lower compartment was determined by counting cells on the underside of the membrane. Data are presented as means ± standard error for six independent determinations. These data show that MIBG inhibits both the growth and the migration of smooth muscle cells in response to specific chemical stimulation.

EXAMPLE IX

Coronary Artery Organ Culture Test for Anti-Restenosis Activity

Figure 9:
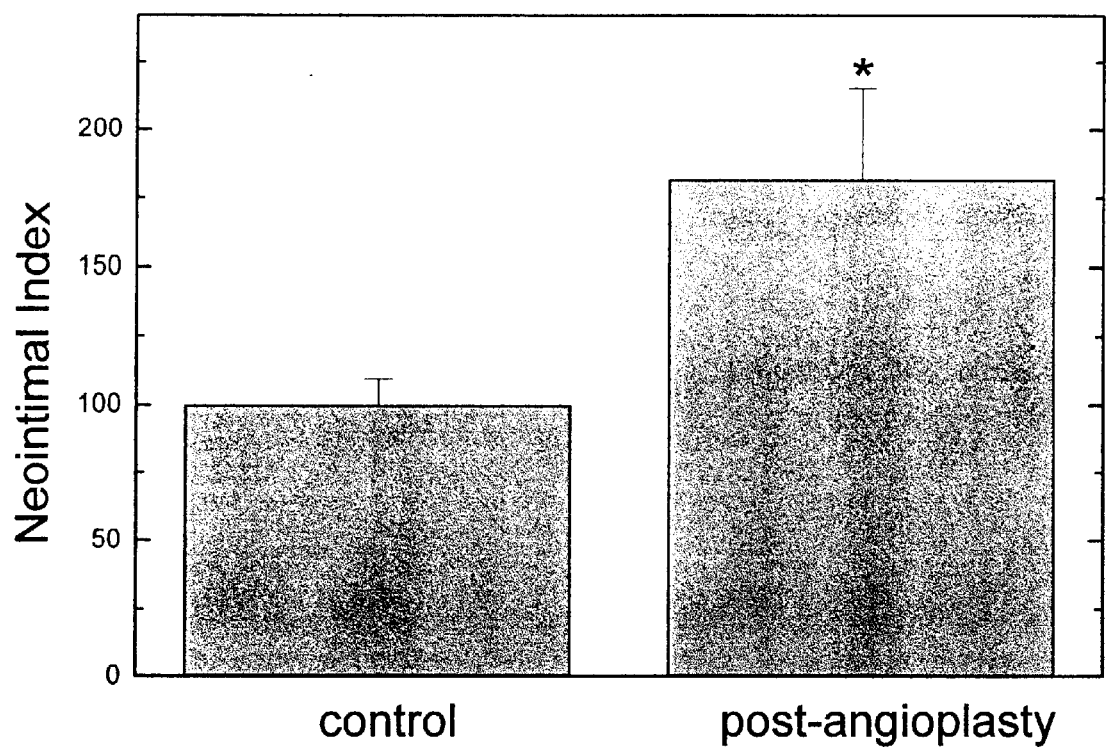
FIG. 9 is a bar graph of neointimal proliferation following balloon angioplasty in organ culture of porcine coronary arteries.
Figure 10:
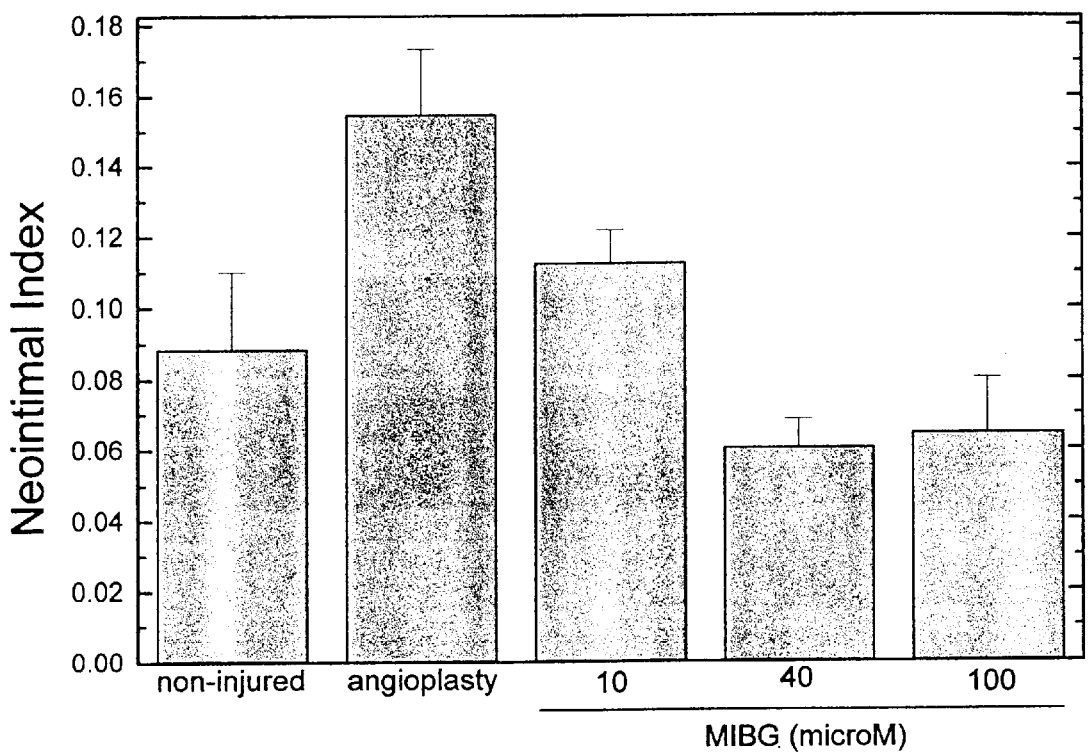
FIG. 10 is a bar graph showing the effect of varying concentrations of MIBG on neointimal proliferation following balloon angioplasty in organ culture of porcine coronary arteries.

Although smooth muscle cell cultures can be used to determine the ability of a compound to inhibit proliferation, these cells are not good indicators of a compound's ability to prevent restenosis. This statement stems from the fact that several processes, including cell migration, proliferation and synthesis of ECM degrading enzymes, must be coordinately activated in order for restenosis to occur. A novel organ culture system has therefore been developed in order to test the effectiveness of MIBG and other compounds at preventing restenosis (Wilson et al, 1999, *Cardiac Res* 42: 761–772). In brief, hearts are transported from the abattoir to the laboratory on ice. The left descending coronary artery is exposed and a balloon catheter is inserted past the first bifurcation. The balloon is inflated, and after 1 minute is deflated and withdrawn. The damaged region (approximately 20 mm in length) is excised, cut into 4 pieces of 5 mm and each piece is placed into an individual well of a culture dish. These segments can be maintained in media containing 20% serum for up to 21 days. Upon harvest of the tissue, typically after 14 days, the vessel segments are placed into resin for histological analysis. Sections are prepared from vessel segments after removal of the first 1.5 mm. This trimming is necessary to remove the cut site which undergoes restenosis from the damage inflicted by the scalpel blade. The sections are stained with Lee's methylene blue and examined microscopically. A digital camera is used to convert the microscopic image to a JPEG file. This file is imported into SigmaScan™, and staining in the areas of the intimal and medial layers quantified. The data is then presented as the neointimal index: (intimal area/medial area)×100. Specifically, the higher the value of the neointimal index, the greater the restenosis. All values are compared to data from age-matched control vessels that were not subjected to balloon angioplasty. Statistical significance between treatment conditions ($p<0.05$) is defined using Student's t-test. In the experiment examining the effect of MIBG (n=4), the neointimal index after balloon injury increased to 140% of control, as shown in FIG. 9. Addition of MIBG to the culture media over the 14 day period of an experiment leads to a concentration-dependent decrease in neointimal index relative to untreated, injured controls, as shown in FIG. 10. As can be seen, at 25 μM, MIBG effectively reduces the neointimal index to control values. It is of note that this concentration of MIBG closely matches the concentration already demonstrated as effective in preventing cell proliferation in cell culture, discussed above. Visual evidence of the histological changes produced by MIBG is shown in FIG. 11. Note the presence of an extensive neointima in the injured section, which is absent in both control and MIBG-treated samples. It is evident from these results that MIBG prevents the neointimal proliferation that results from balloon angioplasty treatment. Furthermore, the effectiveness of MIBG in preventing neointimal formation corresponds with its ability to inhibit smooth muscle cell proliferation, as discussed above.

EXAMPLE X

Bypass Graft Organ Culture

Figure 18:
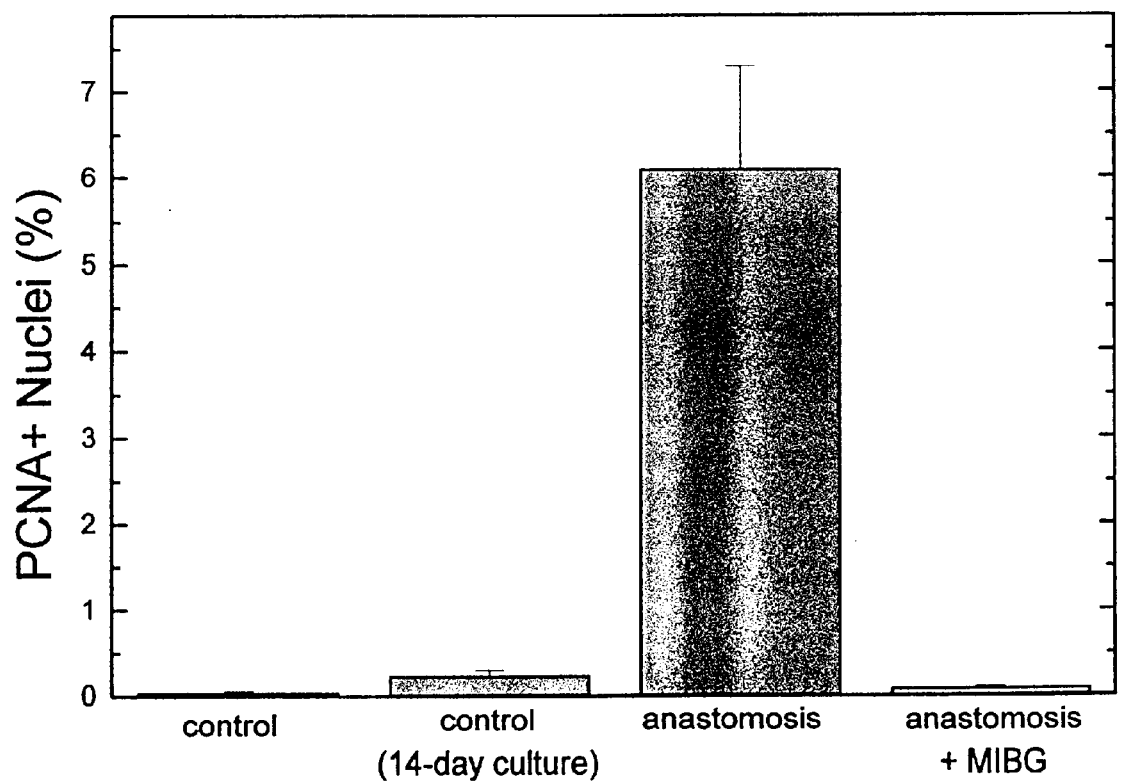
FIG. 18 is a bar graph showing the effect of MIBG on stimulation of PCNA expression after bypass grafting.

Analogous to the organ culture model described above, a model of a radial artery to coronary artery bypass graft has been developed. It is of note that the construction of this anastomosis is identical to that used clinically in a bypass operation. Specifically, porcine radial artery to coronary artery anstomoses were conducted and placed into culture for 14 days. Control segments included coronary artery dissected and immediately frozen or incubated for 14 days before freezing. Alternatively, the anastomoses were incubated in the presence of 25 μM MIBG. PCNA (proliferating cell nuclear antigen) was detected by immunostaining after cryosectioning of the vessels. Nuclei were visualized with Hoescht 55538. The numbers of nuclei and PCNA positive nuclei were determined and used to quantify the proliferation index. These data indicate construction of the anastomosis resulted in an 800-fold increase in PCNA expression at 14 days in culture. In contrast, culture of a coronary artery segment including the constructed anstomosis in the presence of MIBG (VRI-1) for 14 days, resulted in a much reduced increase (<10-fold) compared to a coronary artery segment examined immediately after dissection, which was in fact comparable to results obtained with the controls, as shown in FIG. 18.

EXAMPLE XI

Angioplasty of the Porcine Femoral Artery

Figure 19:
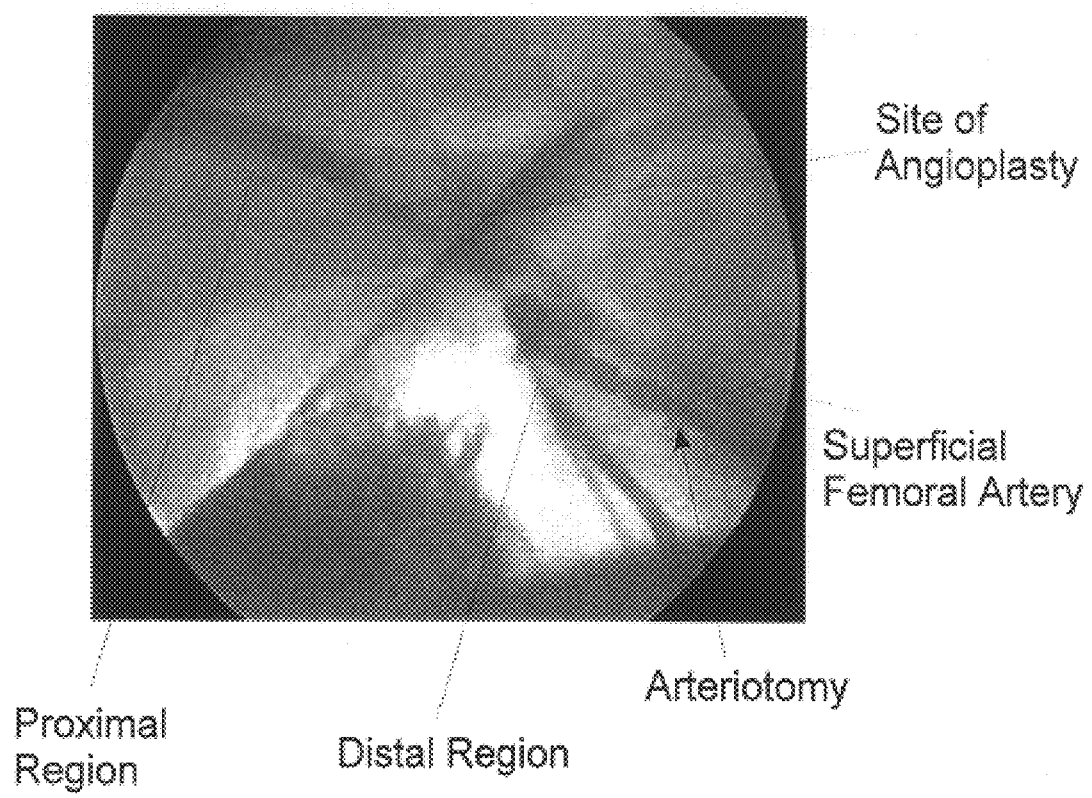
FIG. 19 shows an angiographic assessment of balloon angioplasty on lumen diameter of a porcine femoral artery.

To test the effectiveness of MIBG under in vivo conditions, this compound was applied to the femoral artery after balloon angioplasty. This model provided a means of testing both MIBG and the method of application. Specifically, male castrated farm pigs (25–30 kg) were anaesthetized and maintained on isoflurane throughout the procedure. With the pig in a supine position, the left femoral artery was exposed from the bifurcation of the femoral and superficial femoral arteries to the point of insertion of the femoral artery into the groin. A mixture of nitroglycerin and papaverine was applied to the vessel and the area was covered with a saline-soaked sponge to keep the tissues moist. The right femoral artery was also exposed, treated and covered with a sponge. The left femoral was then clamped at both groin insertion (proximal) and bifurcation (distal) points, and an arteriotomy made at the bifurcation. The balloon (6.0×20 mm) was inserted through the arteriotomy in a retrograde manner (i.e. toward the groin) to a position 20 mm from the arteriotomy and the proximal clamp removed. The balloon was inflated for 1 minute, deflated and carefully removed, and the arteriotomy was closed with 6.0 Prolene™ suture. MIBG in combination with a biocompatible glue, in this example, Tisseel®, was applied to the surface of the vessel extending from the arteriotomy to the proximal region past the site of balloon inflation. The fibrin glue ensured that MIBG slowly diffused into the vessel. Furthermore, the fibrin glue helps to retain MIBG at the site for several days. The right femoral was handled as described above. The incision, including the deep fascia, was then closed with 3.0 Vicryl™ suture and the skin stapled to close the wound. Pigs were treated with antibiotics for 5 days, and euthanized 14 days after the procedure. The extent of restenosis was subsequently monitored by morphometry. Occasionally, angiography was used prior to sacrifice of the animals to determine the extent of lumen reduction, as shown in FIG. 19. Specifically, in FIG. 19, the region used for the live animal testing of MIBG is shown via angiography. Specific points of reference are indicated on FIG. 19, wherein the arteriotomy is the site of balloon insertion and withdrawal and the site of angioplasty indicates the segment subject to balloon inflation. The surgical and data analysis teams were blinded to which artery received MIBG during each procedure. Both Tisseel and Tisseel plus MIBG were prepared for each animal and they were randomly applied to either the left or right femoral artery. Thus, each animal was used as both control and treatment. The effect of Tisseel alone was tested in a separate group of animals.

Femoral arteries were exposed and the region of balloon inflation (identified by visual examination) was marked with suture at both ends. The femoral artery was removed by dissection and divided into 4 segments: arteriotomy, distal, balloon-injured and proximal. Each segment was subsequently cut into 2 pieces which are flash frozen with a dry ice/ethanol bath in OCT and stored at −80°0 C. Sections of 7 μm were prepared with a cryostat, placed onto glass slides and kept at −80° C. until examined. For analysis, the slides were allowed to warm to ambient temperature, placed into Streck tissue fixative for 10 minutes, washed extensively with PBS and stained for 1 minute in Lee's methylene blue which enhances the visibility of the internal elastic lamina, cell nuclei and muscle tissues. The slides were serially washed with water, 70% ethanol and water before being air dried. Digital images were captured with a DAGE-MTI CCD camera and analyzed with SigmaScan Software. The neointimal and medial areas are quantified and used to calculate the neointimal index: neointimal area/medial area.

Figure 20:
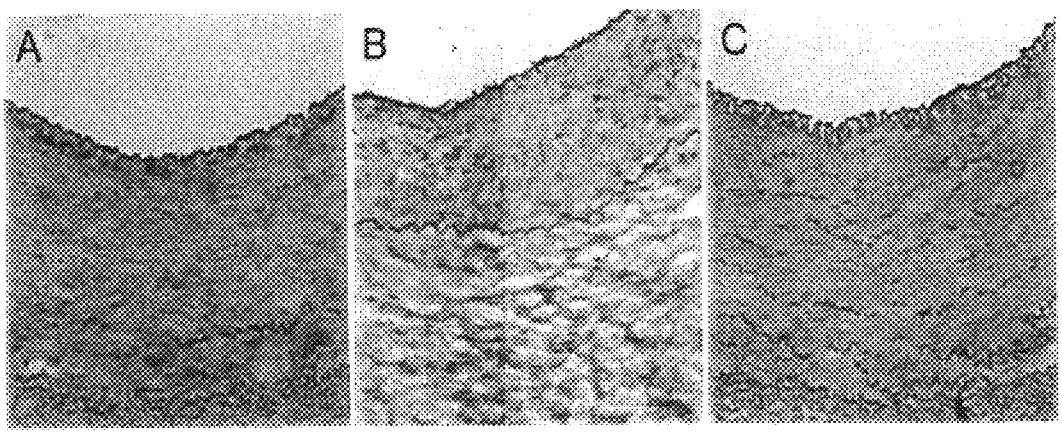
FIG. 20 shows a comparative histology of porcine femoral arteries used to assess the efficacy of MIBG. Panel A shows a typical proximal region that has not been subjected to balloon angioplasty. Panel B shows the extent of stenosis obtained 14 days after balloon angioplasty. Panel C shows the result 14 days after balloon angioplasty in the presence of MIBG.
Figure 21:
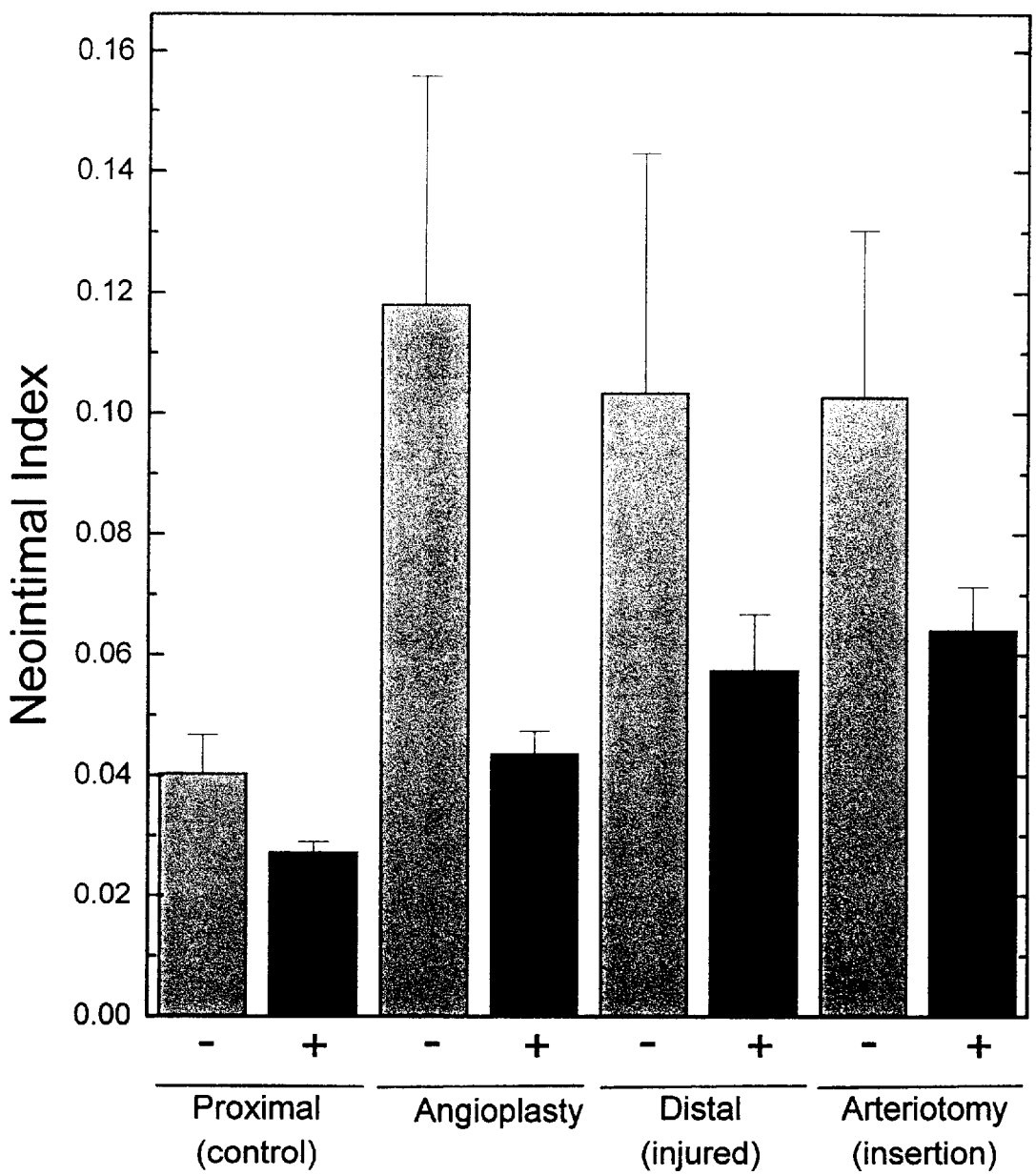
FIG. 21 is a bar graph of data summary for porcine angioplasty results.

The effect of MIBG on neointimal formation has been tested in a total of 13 pigs. The data presented in FIGS. 20 and 21 reveal two important findings. First, MIBG effectively prevents restenosis after balloon angioplasty at the concentration that was used (25 mM in a 1.0 ml Tisseel bolus). Furthermore, there is no evidence of medial fibrosis, unlike the angioplasty without MIBG treatment vessles, or cell loss (FIG. 20). The only distinction from the non-injured control is the lack of endothelial cells. The time period of the experiment (14 days) is insufficient for reendothelialization to occur. Second, the vehicle we have used to apply MIBG maintains the compound at an effective concentration over a sufficiently long period. Our organ culture experiments had shown an exposure time of 4 to 7 days was necessary for MIBG to be effective. Even though the vehicle cannot be detected after 14 days, we conclude that it remains for the minimum period necessary.

EXAMPLE XII

Effect of MIBG Analogues on Smooth Muscle Cell Proliferation

Although MIBG is considered primarily a norepinephrine analogue, it also belongs to a class of compounds distinguished by a guanidino moiety. This guanidino group is the functional portion of MIBG with respect to modification by ADP-ribosylation. Guanidino compounds that have cytostatic activity include for example, methylGAG (methylglyoxal bis (guanylhydrazone)), guanidinoproprionic acid, methylguanidine and guanidinosuccinic acid (Yokozawa et al, 1989, *Nephron* 51: 388–392; Loesberg et al, 1991, *Biochem Pharmacol* 42: 793–798; Shainkin-Kesenbaum et al, 1986, *Nephron* 44: 295–298; Alhonen-Hongisto, 1980, *Biochem J* 188: 491–501). While it is of note that methylGAG has been demonstrated to operate as a substrate for ADPRT (Soman et al, 1983 , *Anal Biochem* 134: 101–110), it has also become apparent that many guanidino compounds have similar properties (Oppenheimer, 1984, *Meth Enz* 106: 399–403).

EXAMPLE XIII

Effect Of MethylGAG on DNA Synthesis

Figure 12:
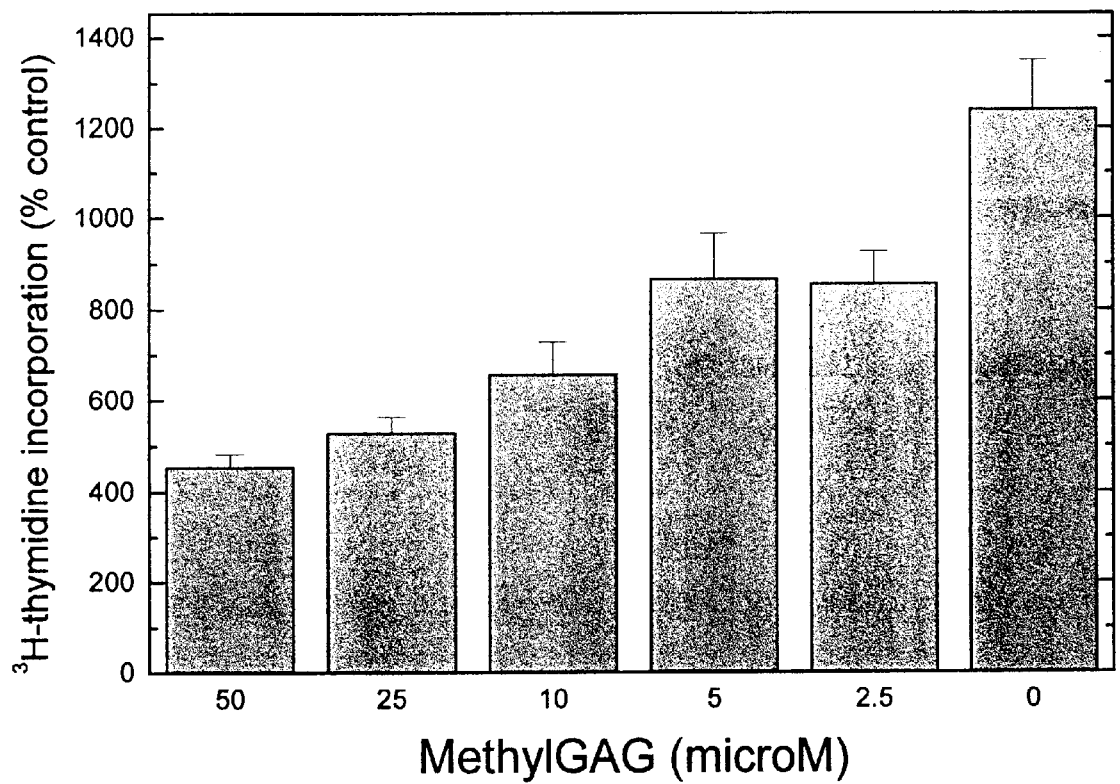
FIG. 12 is a bar graph showing the effect of methylGAG on basal DNA synthesis in quiescent porcine coronary artery smooth muscle cells.
Figure 13:
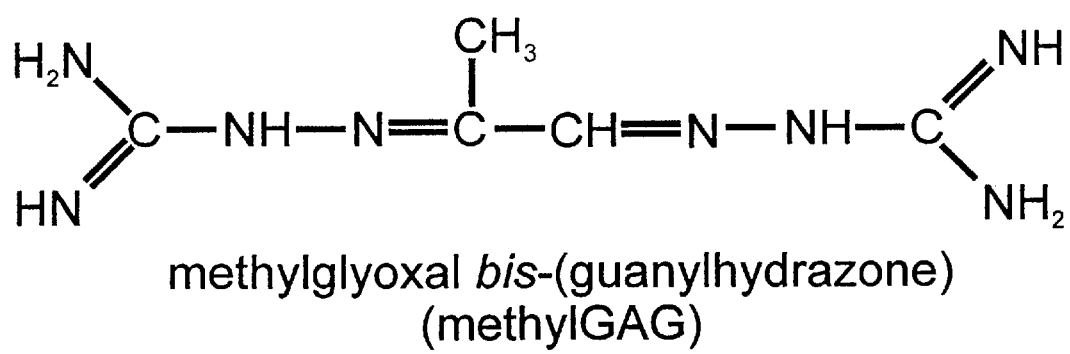
FIG. 13 shows the chemical structure of meta-iodobenzylguanidine (MlBG).
Figure 14:
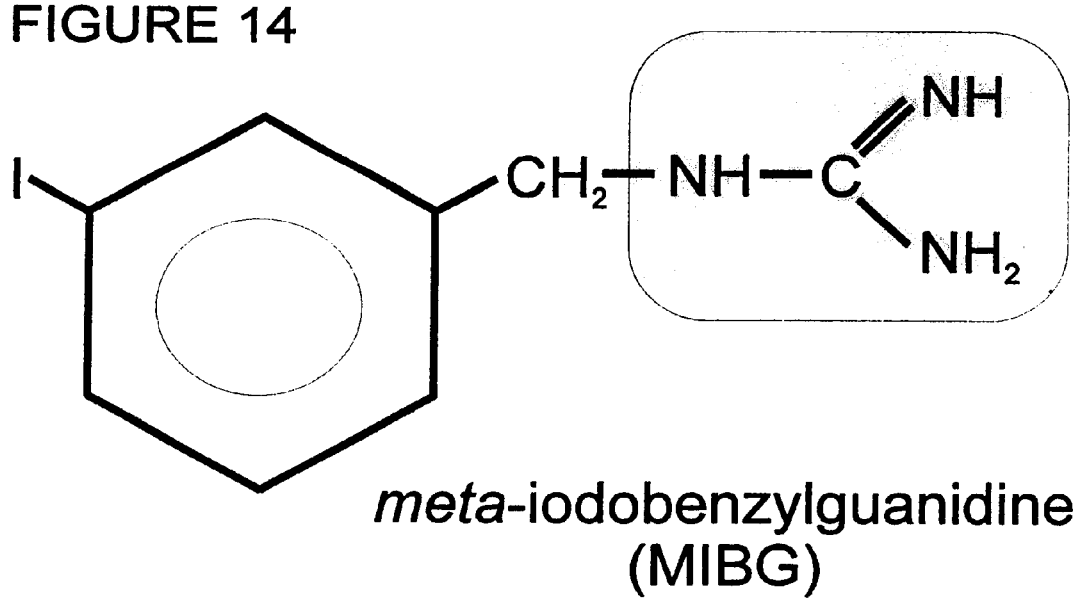
FIG. 14 shows the chemical structure of methylglyoxal bis-(guanylhydrazone) (methylGAG).
Figure 15:
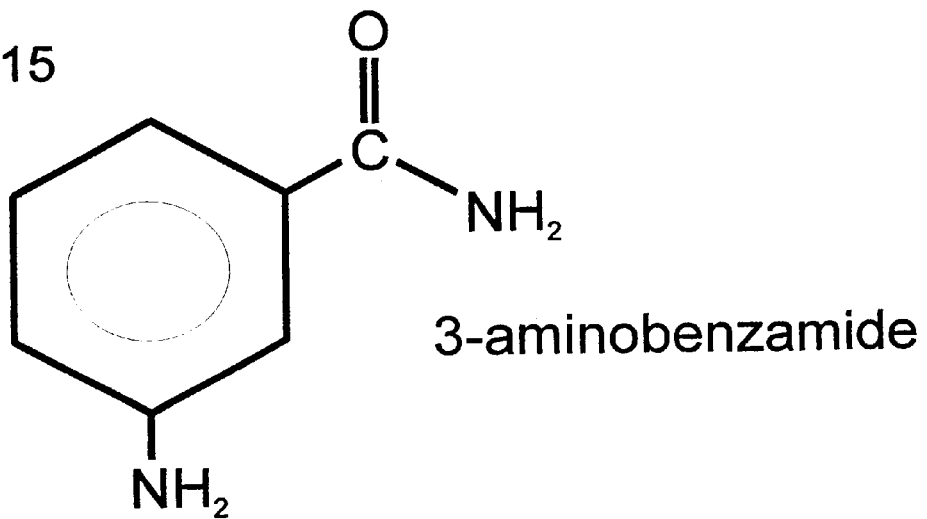
FIG. 15 shows the chemical structure of 3-aminobenzamide.

Since there is a strong possibility that inhibition of cell proliferation by guanidino compounds involves the same mechanism utilized by MIBG, that is, inhibiting ADP-ribosylation, the ability of methylGAG to inhibit smooth muscle cell proliferation was tested. Using thymidine incorporation as the index of proliferation, the data indicate that methylGAG is in fact a slightly more potent inhibitor than MIBG, as shown in FIG. 12. This finding provides support for methylGAG acting through the same intracellular system as MIBG, since methylGAG has 2 guanidino moieties (FIG. 14) compared to the single guanidino group present on MIBG. That is, that methylGAG, like MIBG, is inhibiting an essential ADPRT.

EXAMPLE XIV

Effect of 3-Aminobenzamide and MIBG on map Kinase

Figure 27:
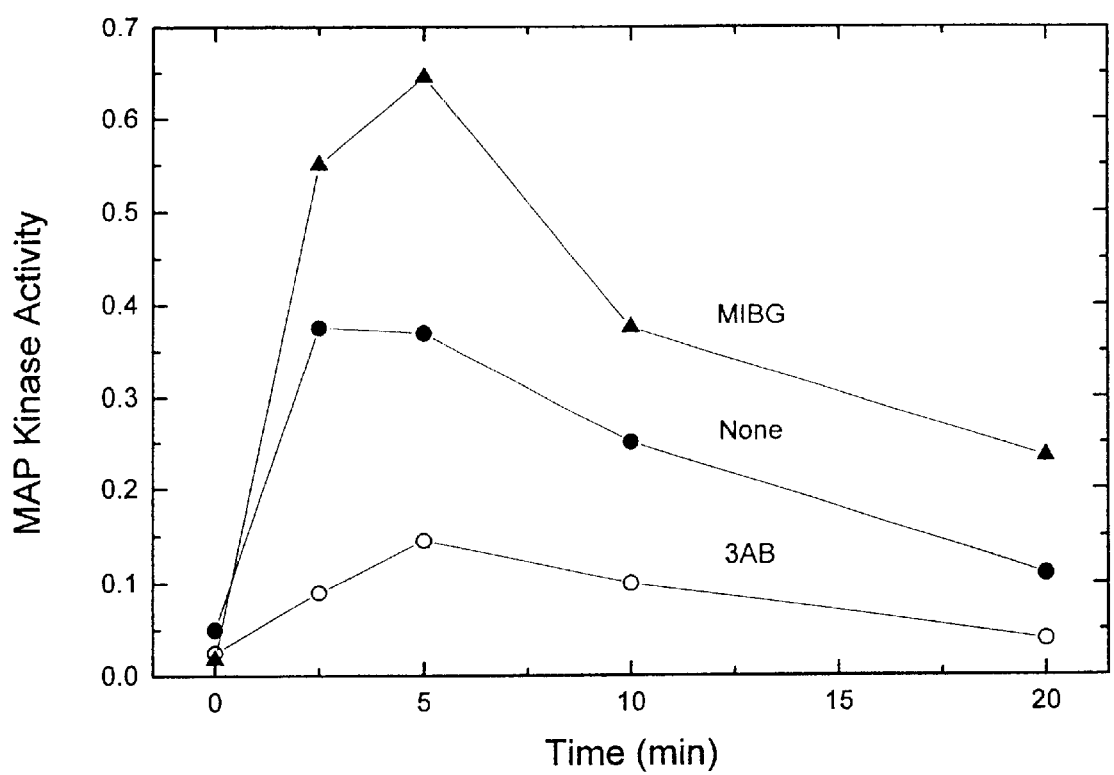
FIG. 27 is a graph of MAP kinase activity over time in cells treated with 3-aminobenzamide and meta-iodobenzylguanidine.

As can be seen in FIG. 27, MIBG, unlike 3-aminobenzamide, does not inhibit MAP kinase activation by insulin. Quiescent H4IIE cells, prepared in 100 mm diameter dishes were stimulated with insulin (1 μM) in the presence of 3-aminobenzamide (1 mM) or MIBG (50 μM). Extracts were prepared at 2, 5, 10 and 20 minutes after insulin addition. MAP kinase activity was measured using an activity gel protocol with myelin basic protein polymerized in the separating gel, as described in Yau and Zahradka, 1997, *Mol Cell Biochem* 172: 59–66. Scanning densitometry was used to quantify the band intensities. The location of the 42 and 44 kDa MAP kinase bands was confirmed by Western blot analysis. Thus, as MIBG does not prevent the stimulation of MAP kinase by mitogens, it is clear that the c-ras system is not a target for MIBG, as was suggested by Thyberg et al.

EXAMPLE XV

Anti-Proliferative Activity of Guanidines and Guanylhydrazones

Figure 24:
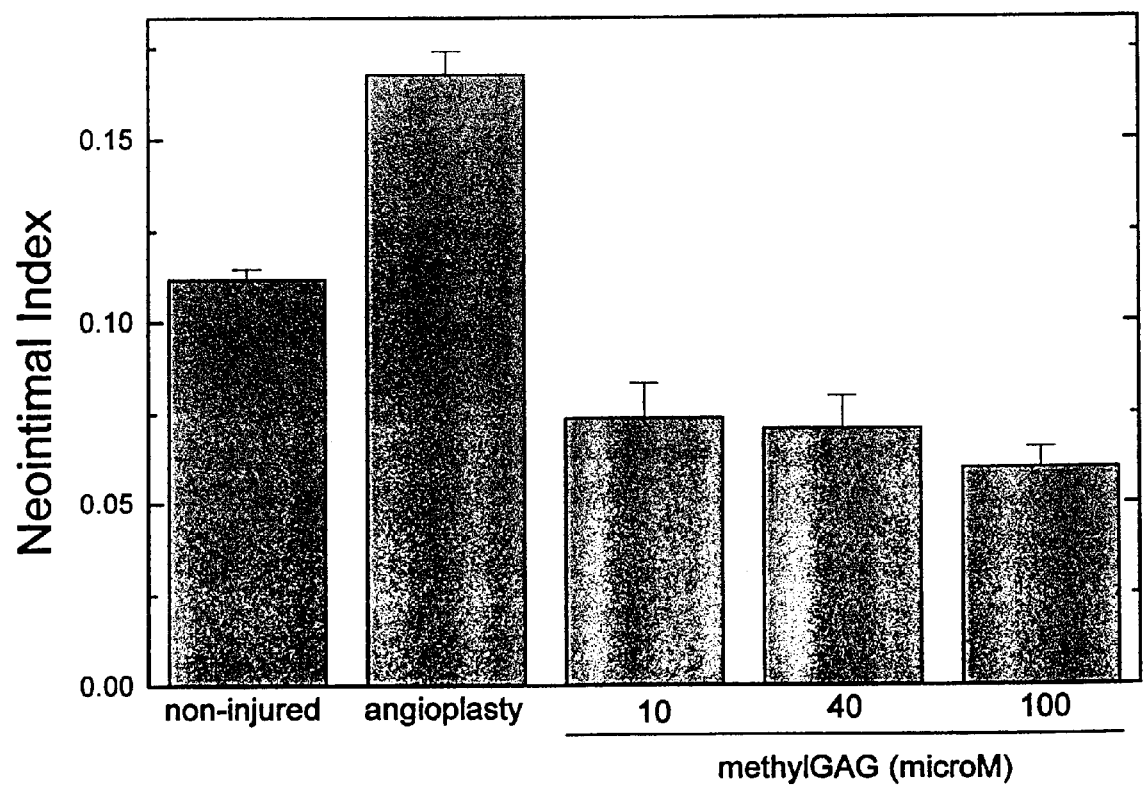
FIG. 24 is a bar graph showing the effect of methylGAG on neointimal formation in organ culture.
Figure 25:
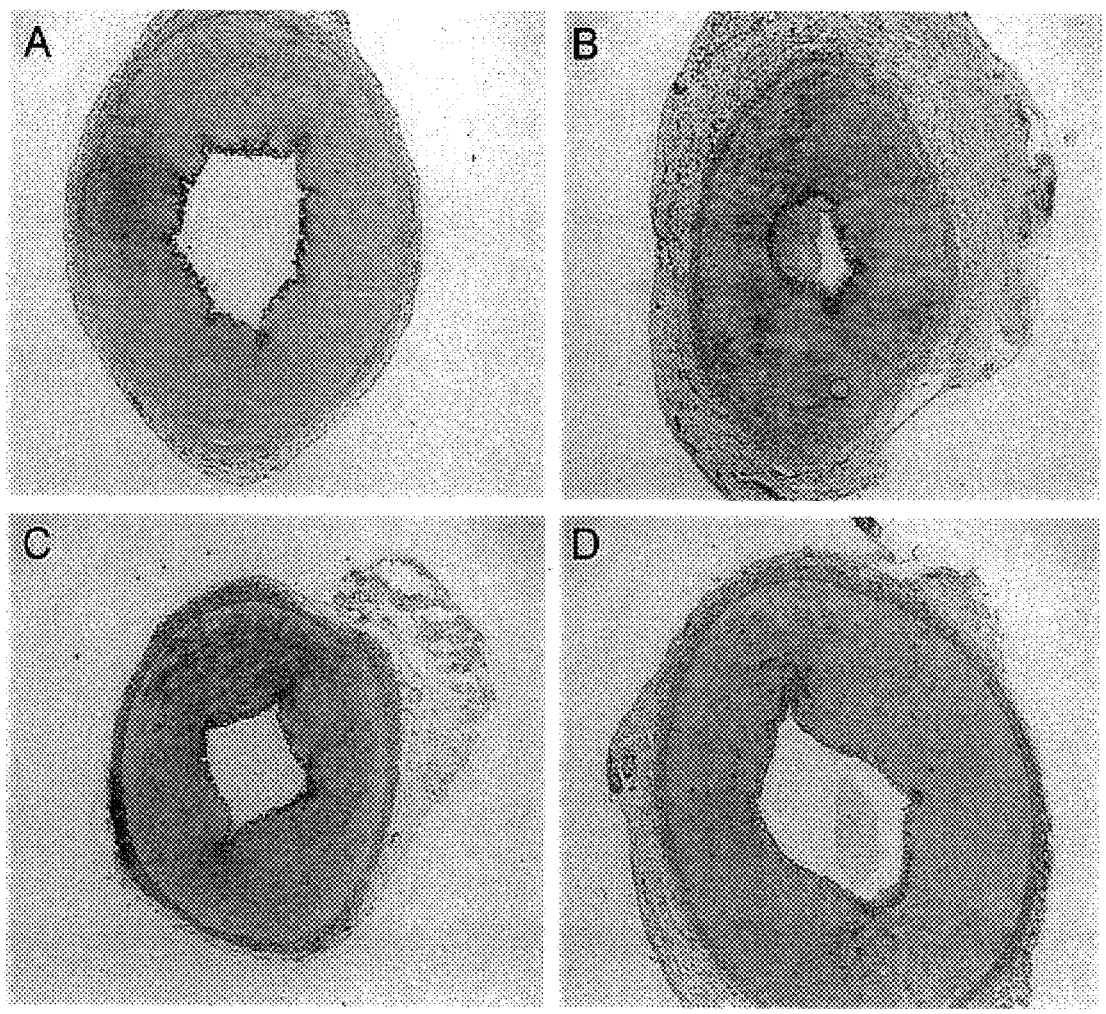
FIG. 25 shows a comparison of arteries that have been treated with methylGAG. Panel A shows the non-balloon injured artery; Panel B shows the balloon injured artery from the same animal; Panel C shows the non-balloon injured artery from a second animal; Panel D shows the balloon injured artery from the same animal as Panel C but with methylGAG treatment.

We have examined other compounds which contain the same functional moiety as MIBG, generally termed guanidines, the general structure of which is shown in FIG. 22. Identification of methylGAG as a possible functional analogue of MIBG was based on the presence of 2 guanidine moieties in this compound. Although it falls into a separate chemical grouping, specifically, guanylhydrazones, the general structure for which is shown in FIG. 23, it nevertheless contains the same functional group as MIBG. In all model systems tested, including H4IIE cells, smooth muscle ells, organ culture and in vivo femoral angioplasty, as well as functional tests, methylGAG has proven as effective as MIBG in preventing cell growth, migration and neointimal formation, as shown in FIGS. 17, 24 and 25. Furthermore, this compound exhibited less toxicity to both porcine and human cells (FIG. 26B), and human studies indicate a higher threshold of tolerance for methylGAG relative to MIBG (Taal et al, 1996, *J Clin Oncol* 14: 1829–1838; Knight et al, 1983, *Invest New Drugs* 1: 235–237).

EXAMPLE XVI

MIBG Inhibits Induction of c-fos Gene Expression

Figure 28:
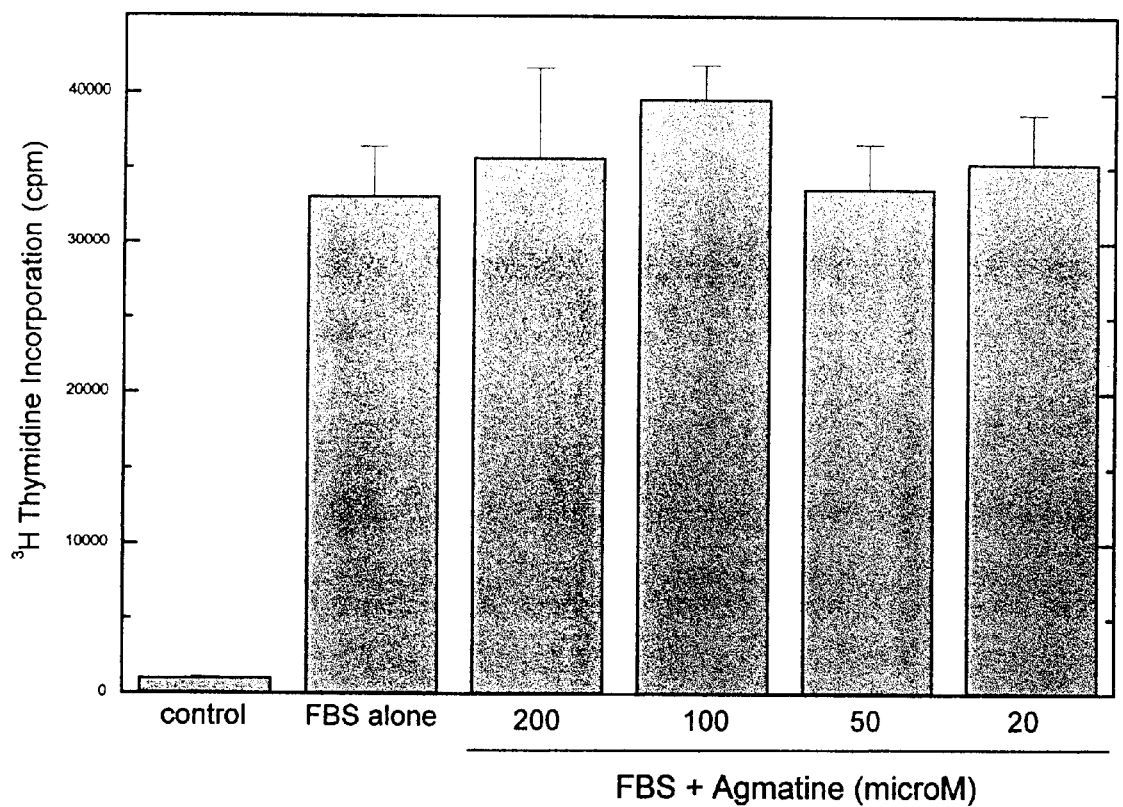
FIG. 28 is a bar graph of $^3$H-thymidine incorporation at various agmatine concentrations.

Human smooth muscle cells were prepared from explants of excess coronary bypass conduits as described previously. Cells were placed into serum-free supplemented medium for 5 days. The quiescent cells were stimulated for 15 minutes with 0.1 M IGF-1 in the presence or absence of 25 μM MIBG, and total RNA extract with TRIZO1™ reagent (Gibco BRL). As shown in FIG. 28, an equivalent amount (1 μg) of RNA from each sample (lane 1—quiescent; lane 2—IGF-1 stimulated; lane 3—MIBG pretreated (10 minutes) then IGF-1 stimulated; and lane M—molecular mass markers) was subjected to amplification by reverse transcriptase polymerase chain reaction (RT-PCR) with oligonucleotide primers specific for the human c-fos sequence. The products were separated according to size by electrophoresis in 2,0% agarose and visualized by staining with ethidium bromide. Specific RT-PCR amplification of c-fos generated a unique product of 238 base pairs, and the relative band intensity correlates with the amount of mRNA present in the cell. The data show that IGF-1 increased c-fos mRNA levels by approximately 5 fold (FIG. 28, lane 2) over basal unstimulated conditions (FIG. 28, lane 1). Pretreatment with MIBG, however, results in c-fos mRNA levels (FIG. 28, lane 3) that are equivalent to or below basal. Since c-fos is among the first genes activated in response to stress, mitogens, chemotactic factors, interleukins and a number of additional stimuli, these data show that MIBG operates at a very early stage in the processes leading to cell proliferation, migration and inflammation.

EXAMPLE XVII

Thymdine Uptake in H4IIE Cells and Smooth Muscle Cells

Figure 30:
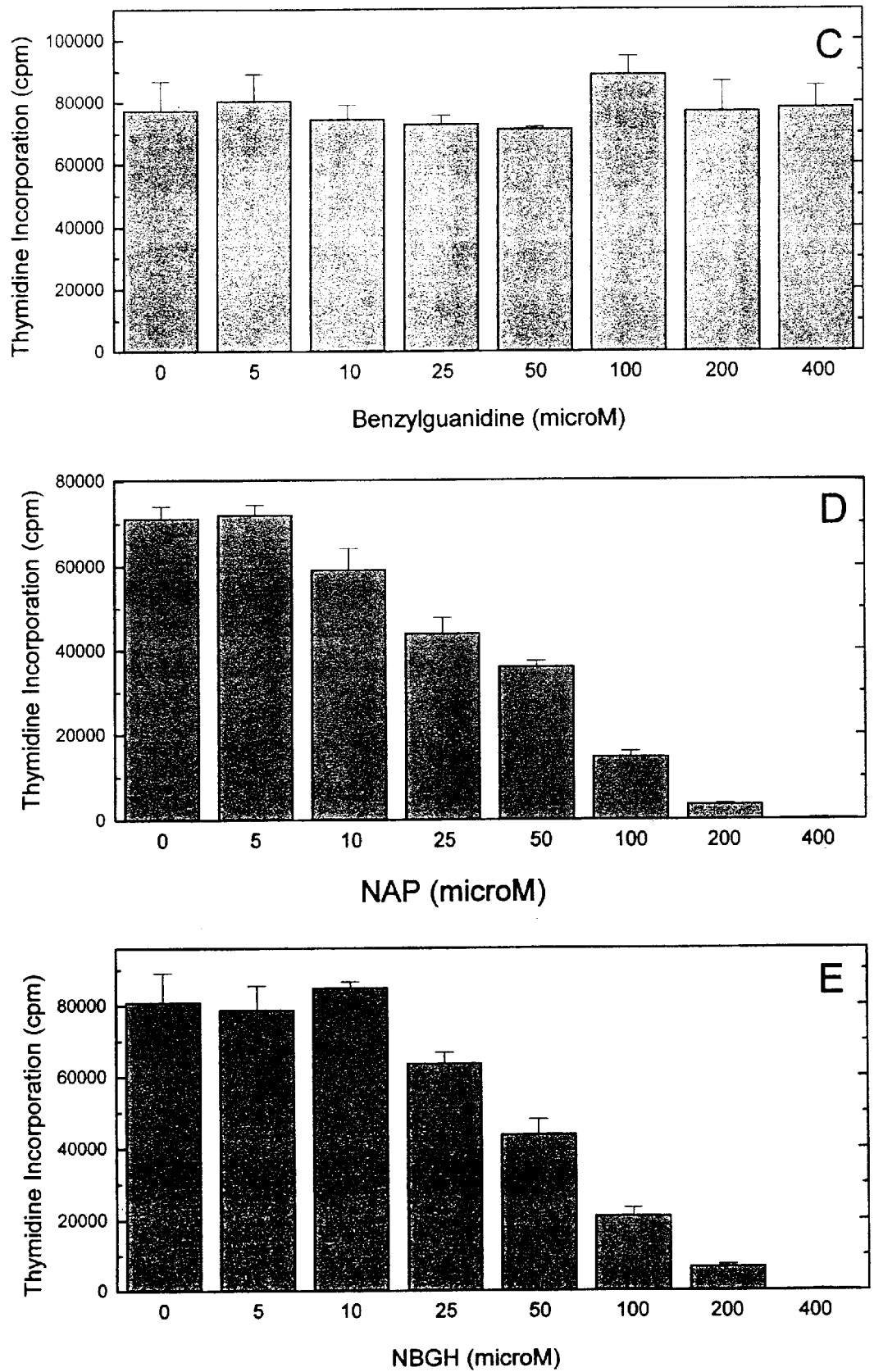
FIG. 30 is a bar graph of thymidine incorporation in smooth muscle cells at various concentrations of (A) MIBG, (B) synthesized MIBG, (C) BG, (D) NAP and (E) o-nitrobenzylguanylhydrazone.
Figure 31:
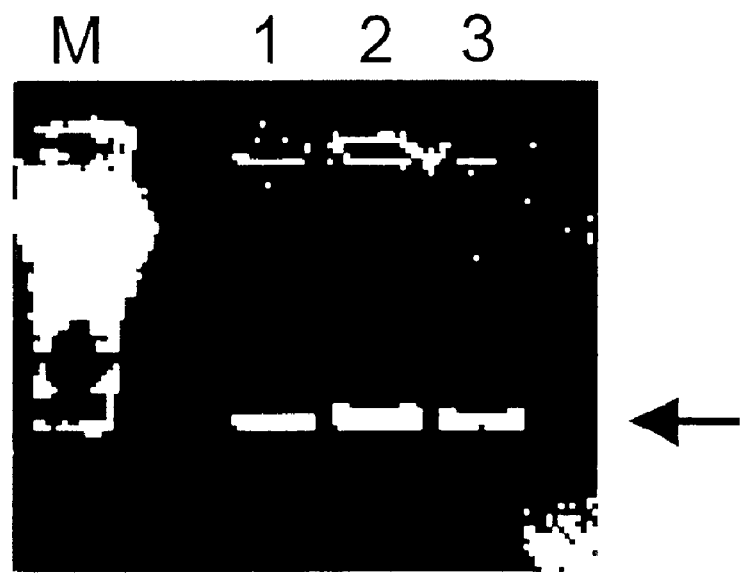
FIG. 31: Effect of MIBG on c-fos gene expression. Total RNA was extracted from human smooth muscle cells and RT-PCR amplified with primers specific for the c-fos proto-oncogene. A specific band of 293 bp was obtained (indicated with arrow), as confirmed by the mobility of the band relative to molecular size markers (lane M). Treatments of the quiescent cell population include: no treatment (lane 1), 10 ng/mL PDGF-BB (lane 2), and 10 ng/mL PDGF-BB after pretreatment (10 min) with 25 $\mu$M MIBG (lane 3).

As can be seen in FIGS. 30 and 31, BG did not inhibit thymidine incorporation. To be effective, a pharmaceutical must enter the cell it is to influence. Several distinct criteria determine whether a compound is capable of cell entry. The most physiologically relevant is the presence of a receptor or transporter that mediates passage of a chemical through the cell membrane. Although transportermediated entry of MIBG has been reported, as discussed earlier, this transport mechanism is absent in many cells capable of accumulating MIBG. Thus MIBG, and most guanidine compounds, must be capable of simple diffusion in order to exert their effects. The structural requirements for this property include the presence of a lipophilic group (eg. aliphatic chain as present in methylGAG, or aryl substituent of MIBG) and the absence of charged groups. Thus agmatine, which is an effective acceptor of ADP-ribose, has limited capacity for cell entry by diffusion. This would explain why agmatine is ineffective as an inhibitor of cell proliferation, as discussed above. It is important to note however that a pharmaceutical composition containing agmatine or another ADPRT decoy substrate that does not readily diffuse into some cells could be encapsulated or otherwise arranged for enhanced cell entry.

Similarly, benzylguanidine is also a poor inhibitor of cell proliferation; however, it is structurally similar to MIBG and should be capable of diffusion into a cell. Benzylguanidine, however, is lacking the electron donating group (eg. nitro) required for activation of the guanidine moiety as an ADP-ribose acceptor (Soman et al, 1986, *Biochemistry* 25: 4113–4119). It has been proposed that this class of substituent is necessary for reducing the pKa of the guanidine to a physiological range. Thus the charge carrier by the guanidine will influence its ability to function as a decoy substrate for ADPRT.

The differential effects of MIBG versus methylGAG in terms of toxicity and anti-proliferative activity suggests these properties result from different cellular targets. First, the near equivalence in growth inhibitory concentrations suggests this action represents a common target. Given the structural differences, ADP-ribose acceptor function is the likely common factor. Second, the greater toxicity observed with MIBG relative to methylGAG, in contrast, suggests this aspect of MIBG on a cell is driven by a different mechanism. Since the toxic concentration (>100 uM) is higher than the concentration required to inhibit cell proliferation (10–50 uM), toxicity is presumed unrelated to ADPRT activity. This view is supported by the lack of toxicity observed with methylGAG. In contrast, MIBG has been reported to decrease mitochondrial function. This may also explain the discrepancy noted with respect to the MTT and LDH cytotoxicity assays, which suggest MIBG causes cell death at concentrations of >100 uM, and microscopic observations of the treated cells which suggest they are unaffected by MIBG. A reduction in mitochondrial activity will be reflected by a decrease in MTT reduction and thus an impression of decreased cell number (i.e. death). Reduced mitochondrial activity also leads to acidification of the intracellular environment, resulting in increased lactate production. Lactate dehydrogenase levels will subsequently increase. Our observed increase in LDH release may therefore be a consequence of this corrective measure, and thus unrelated to cell death. Since methylGAG does not affect mitochondrial metabolism, there is no appearance of toxicity. Apparent toxicity and anti-proliferative activity are therefore distinct properties of MIBG, and may not be applicable to other guanidine compounds such as methylGAG.

EXAMPLE XVIII

Discussion

As discussed above, meta-iodobenzylguanidine (MIBG) inhibits arginine-dependent mono(ADP-ribosyl)ation (Loesberg et al, 1990, *Biochim Biophys Acta* 1037: 92–99). Since mono(ADP-ribosyl)transferase (ADPRT) activity increases following mitogen stimulation, and inhibition of this enzyme prevents cell proliferation (Yau et al, 1998, *Eur J Biochem* 253: 91–100), the anti-differentiation actions of MIBG are likely to be mediated through ADPRT. Studies indicate that MIBG blocks cell proliferation by preventing the post-translational modification of specific protein molecules critical for signal transmission following growth factor stimulation.

Figure 16:
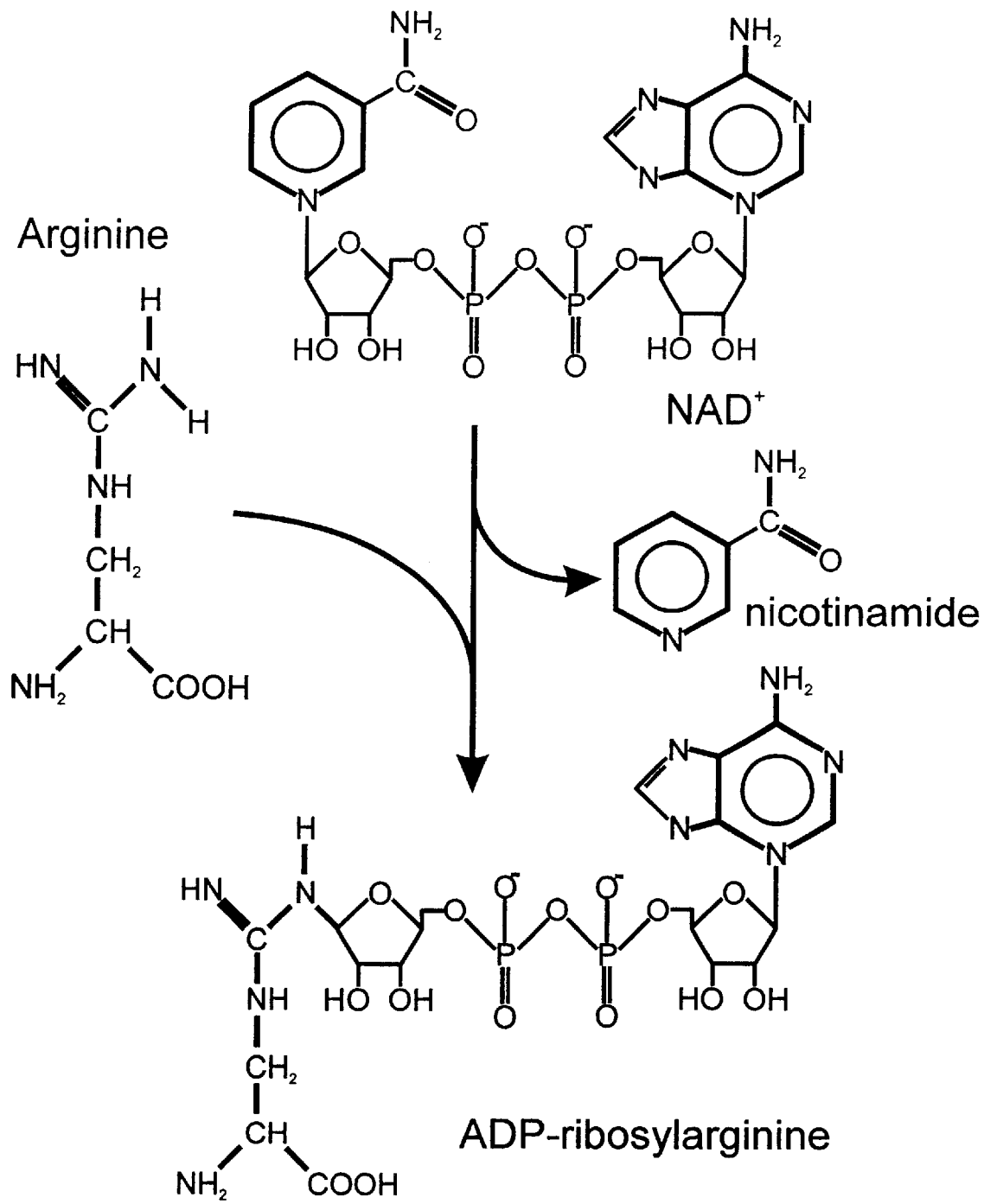
FIG. 16 shows the mechanism of argininine-dependent ADP ribosylation.

Studies conducted with H4IIE hepatoma cells were designed to survey a variety of cellular processes to determine whether they were mediated by argininedependent mono(ADP-ribosyl)ation (FIG. 16). The assumptions applied to this work were: i) an effect observed with high concentrations of the nicotinamide analogue 3-aminobenzamide were indicative of mono(ADP-ribosyl)ation reactions rather than poly(ADP-ribosyl)ation, and ii) MIBG was a specific inhibitor of arginine-dependent ADPRTs. The first assumption was based on prior studies wherein it was demonstrated that ADPRT was affected by 3-aminobenzamide concentrations of 1 mM or greater (Rankin et al, 1989, *J Biol Chem* 264: 4312–4317; Banasik et al, 1992, *J Biol Chem* 267: 1569–1575). Using this value as the lower limit for detecting ADPRT, the literature was searched to determine what cellular processes were sensitive to 3-aminobenzamide at concentrations of 1 mM or higher. It must be stated that prior to publication of Zahradka and Yau, 1994, *Mol Cell Biochem* 138: 91–91, inhibition by 3-aminobenzamide was primarily considered a marker for the involvement of poly(ADPribose) polymerase (PARP). It is now evident from transgenic animal models that the absence of PARP is not lethal, and the only altered phenotype detected in these animals is a heightened sensitivity to DNA damaging agents (Trucco et al, 1998, *NAR* 26: 2644–2649). Thus there is no data suggest that PARP is required for cell proliferation events. These findings therefore support the statement that ADPRT is the target for 3-aminobenzamide when discussing cell growth inhibition. It is also of note that mitogen stimulation results in elevated ADPRT activity (Yau et al, 1998, *Eur J Biochem* 253: 91–100).

The results presented above clearly show that MIBG inhibits cell proliferation. Of note is the fact that MIBG accumulation occurs in the presence of excess norepinephrine, indicating an independence from receptor-mediated processes. Furthermore, it is of note that there have been reports that MIBG accumulates in the smooth muscle cells of a small intestinal sarcoma devoid of neuronal innervation, which provides confirmation of an interaction between MIBG and smooth muscle cells independent of neuronal cells (Akle et al, 1997, *Eur J Nucl Med* 24: 1196).

The flow cytometry data presented above and in FIG. 4 shows that MIBG completely inhibits cell proliferation even in the presence of fetal bovine serum. This is an important fact, since serum contains multiple mitogenic factors. Thus, the process affected by MIBG is one commonly employed by all mitogens. Furthermore, the specific enzymatic target for MIBG is essential for cell cycle progression at multiple points. The latter conclusion is based on the observation that cells do not accumulate in a specific phase of the cell cycle in the presence of MIBG.

As discussed above, MIBG was synthesized as an analogue of norepinephrine. Uptake into neuroblastoma cells was found to involve two mechanisms, one saturable and therefore receptor-mediated, and the other non-saturable and therefore receptor-independent (Smets et al, 1990, *Biochem Pharmacol* 39: 1959–1964). There has been difficulty in defining the relative contribution of each uptake mechanism since the adrenergic receptor antagonists that are the most effective in blocking MIBG uptake (for example, propranalol, phenoxybenzamine) appear to also influence general membrane function (Babich et al, 1997, *Eur J Nucl Med* 24: 538–543). It is of note however, that among the compounds capable of reducing MIBG uptake is guanethidine (Babich et al, 1997, *Eur J Nucl Med* 24: 538–543), a guanidino derivative that is structurally related to MIBG and which may also be a substrate for ADP-ribosylation.

The importance of the guanidino moiety of MIBG for its inhibitory function is demonstrated by the different properties exhibited by MIBG when compared with those exhibited by MIBA. While structurally related, except for the guanidino group, MIBG is at least 100 times more effective as an anti-tumor agent (Smets et al, 1988, *Cancer Chemother Pharmacol* 21:9–13). Support for the importance of the guanidino group is provided by the fact that benzylguanidine and the various isomers of MIBG (p-IBG, o-IBG) retain a similar efficacy as cytotoxic agents (that is, within a factor of 5). Furthermore, it has been established that guanylhydrazones, like MIBG, are substrates for mono (ADP-ribosyl)ation (Soman, 1983). In addition, a number of guanylhydrazones and diguanidines have been found to exhibit anti-proliferative activity (Alhonen-Hongisto, 1980; Mihich, E, in Handbook of Experimental Pharmacology (Springer, Berlin: 1975) pp 766–788). Of these compounds, methylGAG has been tested extensively for its application to anti-cancer therapy (Knight et al, 1983, *Invest New Drugs* 1: 235–237). It is of note that methylGAG is, as discussed above, a substrate of mono(ADP-ribosyl)ation (Soman, 1983) and that high concentrations of 3-aminobenzamide and nicotinamide produced similar effects provides further evidence that ADPRT is the target of the antiproliferative activity.

A major advantage of MIBG is the fact that it accumulates in target tissues. To date, it has been assumed that increased cellular levels of MIBG occur as a result of entry into catecholamine storage granules (Gasnier et al, 1986, *Mol Pharmacol* 29: 275–280). On the other hand, accumulation in cells lacking this mechanism does occur (Akle, 1997), and other guanidino compounds exhibit the same property (Yokozawa, 1989; Mandel and Flintoff, 1978, *J Cell Physiol* 97: 335–343). Specifically, it has been noted that MIBG can attain a concentration 15 times higher in the non-neuronal cell line L1210 than in the surrounding medium (Smets et al, 1990, *Biochim Biophys Acta* 1054: 49–55), despite the fact that these cells lack the uptake mechanism for catecholamines that are present in neuronal cells. Therefore, the increase in intracellular MIBG cannot be due to transfer into storage granules. Since MIBG can be modified by ADPRT, resulting in ADP-ribosylated MIBG, an alternative mechanism can be proposed for MIBG accumulation. As MIBG enters the growing cells, ADPRT modifies the compound. This modification adds two negative charges to the molecule, and thus prevents its passage through the plasma membrane and out of the cell. In addition, the MIBG modification effectively removes it from the intracellular MIBG pool, thus permitting further diffusion from extracellular sources. Thus, the anti-proliferative properties of MIBG are enhanced as a result of its status as an ADPRT substrate, since depletion of the MIBG pool by ADP-ribosylation leads to continued MIBG entry into the target cell even in the presence of modest extracellular MIBG concentrations.

Several mechanisms for MIGB's actions have been proposed. However, none of these mechanisms have been reported as directly linked or unlinked from its role as an ADPRT decoy substrate. Furthermore, there are several potential mechanisms by which MIGB may influence cell proliferation.

For example, the mitochondria may be a major site for MIBG function. It has been reported that ATP production is blocked by MIBG via its effects on malate and succinate-dependent complex I and II respiration (Cornelissen et al, 1995, *Biochem Pharmacol* 49:471–477). Along similar lines, mitochondrial calcium levels are increased in cells subjected to MIBG (Juedes et al, 1992, *FEBS Lett* 313:39–42). The latter report has implicated ADPRT simply by the fact that MIBG inhibits this enzyme. Each of these actions, however, may account for the changes observed in MTT production, shown in FIG. 3, since conversion of MTT to the spectrophotometrically detectable coloured compound occurs in the mitochondria. Membrane effects, specifically involving ion leakage, are also possible mechanisms by which MIBG could influence ATP production. This possibility is raised on the basis of reports that MIBG increases lipid peroxidation of mitochondrial membranes (Mihich, 1975). Changes in lipid oxidative state may also account for the increased release of LDH, shown in FIG. 5, even though cell death is not evident microscopically. Plasma membrane effects are also indicated by the action of MIBG on histamine-receptor interactions (Jonsson et al, 1998, *Biochim BiophysActa* 1379: 143–150). Similarly, the reduction in cellular pH, suggested recently as a major factor in MIBG's anti-proliferative actions (Kuin et al, 1999, *Br J Cancer* 79: 793–801), can be linked to changes in membrane integrity. The involvement of ADPRT in mitochondrial processes has not been extensively pursued; however, the fact that MIBG and methylGAG have similar effects on cell proliferation, as shown in FIG. 12, yet they are distinct in their actions on mitochondrial respiration and polyamine synthesis (Loesberg et al, 1991), suggests they operate through the same mechanism.

MIBG has been found to influence other systems as well. The synthesis of prostacyclins by endothelial cells is inhibited by MIBG (Halldorsson et al, 1992, *FEBS Lett* 314: 322–326). Since guanethidine has a similar effect, ADPRT has been suggested as an important factor in this process. It is important to note that prostanoids are important mediators of cell proliferation, and can operate as secondary growth factors of smooth muscle cells following mitogen stimulation (Saward and Zahradka, 1996, *J Mol Cell Cardiol* 28: 499–506; Mallat et al, 1998, *J Biol Chem* 273: 27300–27305). It is noteworthy that viral DNA replication is also inhibited by MIBG, presumably through a requirement for coat protein ADP-ribosylation (Child and Hruby, 1993, *Biochim BiophysActa* 1157: 217–228). Furthermore, experimental results in another study have suggested that MIBG plays a role in insulin-dependent events (Yau et al, 1998), which suggests that ADP-ribosylation is important for intracellular signalling. MIBG has also been shown to inhibit protein phosphorylation in response to lipopolysaccharide (LPS) treatment (Hauschildt et al, 1998, *Prog Clin Biol Res* 397: 147–155). In fact, inhibition of phosphorylation may represent the mechanism by which MIBG prevents LPS-dependent TNF-α and IL-6 production. Two other obvious systems which may be influenced by MIBG have not been examined. It is known that MIBG will bind to adrenergic receptors. While no post-receptor activity is evident with MIBG, the signalling molecule most likely to increase is cAMP, since adrenergic receptors are coupled to adenylate cyclase. It is well established that cAMP inhibits smooth muscle cell proliferation in response to most mitogens (Giasson et al, 1997, *J Biol Chem* 272: 26879–26886). This route, however, is not independent of ADPRT, since the G proteins that regulate adenylate cyclase activity are targets for ADP-ribosylation (Tanuma et al, 1988, *J Biol Chem* 263: 5485–5489; Inageda et al, 1991, *Biochem Biophys Res Commun* 176: 1014–1019). The relevance of adrenergic receptor activation, however, may be minimal given the fact that methylGAG and other guanidino compounds that exhibit anti-proliferative activity are structurally distinct from MIBG and therefore unlikely to bind the receptor. Alternatively, it is known that arginine and similar guanidino containing molecules are substrates for nitric oxide synthase. Arginine is therefore necessary for nitric oxide (NO) production. While it is unclear whether MIBG may serve the same function, it has been clearly established that NO has anti-proliferative activity (Sarkar et al, 1997, *Am J Physiol* 272: H1810–H1818). Furthermore, nitric oxide synthase expression may be regulated by ADP-ribosylation (Pellat-Deceunynck et al, 1994, *Biochem J* 297: 53–58). Interestingly, nitric oxide synthase activity is inhibited by MIBG in vitro, but only at concentrations much higher than those that prevent cell proliferation (Kuin et al, 1998, *Cancer Chemother Pharmacol* 42: 37–45).

The inhibition of c-fos gene expression by MIBG permits speculation about the mode by which this compound is capable of inhibiting multiple, yet apparently independent, cellular processes such as proliferation, migration, inflammation and differentiation. There are two possible scenarios by which MIBG could influence so many cellular processes. First, it has been demonstrated that c-fos, functioning through AP-1 transcription factor, is essential for both proliferation and differentiation (Chen et al, 1996, *Mol Carcinog* 15: 215–226; Lehtinen et al, 1996, *Biochem Biophys Res Comm* 229: 36–43; Lassar et al, 1989, *Cell* 58: 659–667; Rahm et al, 1989, *J Cell Physiol* 139: 237–244). Therefore, a reduction in c-fos mRNA could affect both processes under the appropriate conditions. Alternatively, MIBG operates through the TCFs (ternary complex factors) that regulate c-fos gene expression. Since MIBG does not inhibit the activation of MAP kinase, the likely TCF target for MIBG would be SRF, the serum response factor, rather than Elk-1. SRF has also been shown to be essential for proliferation and differentiation, albeit via a mechanism independent of its action on the c-fos gene (Wei et al, 1998, *J Biol Chem* 273: 30287–30294). In either case, MIBG decreases the ability of a key transcription factor to stimulate the expression of genes critical to the processes of both proliferation and differentiation. It is in this manner that MIBG can influence all of these diverse cellular processes.

Finally, it has been proposed that agmatine inhibits smooth muscle cell proliferation through imidazoline receptors (Regunathan and Reis, 1997, *Hypertension* 30: 295–300). While imidazolines are believed to operate through $I_1$ and $I_2$ receptors, it is also known that they can bind with high affinity to adrenergic receptors (Bousquet, 1997, *Neurochem Int* 30: 3–7; Regunathan and Reis, 1996, *Annu Rev Pharmacol Toxicol* 36: 511–544). As indicated above, adrenergic ligands can inhibit cell proliferation by elevating cAMP. Therefore, it is plausible that the imidazoline ligands influence smooth muscle cell proliferation by this mechanism. This premise is supported by published evidence showing inhibition of cell proliferation by idozoxan (an imidazoline receptor agonist) is prevented by an adrenergic receptor antagonist, but not by an imidazoline receptor antagonist (Regunathan et al, 1996, *J Pharmcol Expt Ther* 276: 1272–1282). Although agmatine has been shown to interfere with binding of idazoxan to imidazoline receptors, no publication has shown that agmatine affects cell function by this mechanism. This concept is justified by the fact that agmatine has not been shown to affect binding to adrenergic receptors. For this reason, it remains most likely that inhibition of smooth muscle cell proliferation by agmatine occurs via inhibition of ADPRT. Furthermore, it is of note that contrary to this published report, FIG. 28 shows that agmatine does not inhibit DNA synthesis by smooth muscle cells in response to serum treatment.

Furthermore, while the relevance of the finding that MIBG (FIG. 32) prevents the differentiation of Friend erythroleukemia cells and L6 myoblasts to restenosis may not be evident, they are critical to understanding the entire restenosis process. To date, we have focused our attention on the role of smooth muscle cells in vascular injury. It is noteworthy, however, that the physical injury caused by angioplasty produces an inflammatory response (Komowski et al, 1998, *J Am Coll Cardiol* 31: 224–230). This response is initiated by secretion of specific chemotactic proteins (for example, MCP-1) from the damaged cells leading to the recruitment of monocytes to the site of injury (Furukawa et al, 1999, *Circ Res* 84: 306–314). The monocytes subsequently infiltrate the tissues and differentiate into macrophages that produce the matrix metalloproteinases required for cell migration, as well as growth factors that stimulate smooth muscle cell proliferation (Libby et al, 1992, *Circulation* 86(supplement 6): 11147–11152). Similarly, smooth muscle cells must alter their phenotype prior to migration and proliferation (Walsh and Perlman, 1996, *Semin Interv Cardiol* 1: 173–179). This differentiation process, which is inherently required for restenosis, results in cells distinct from those present in the normal medial layer, since they are capable of secreting matrix metalloproteinases and undergoing cell division. Based on the results obtained with the Friend cell and L6 myoblast models discussed above, it is likely that MIBG will also inhibit monocyte and smooth muscle differentiation. Since mono(ADP-ribosyl)ation has been reported to participate in the skeletal muscle differentiation process (Kharadia et al, 1992, *Exp Cell Res* 201: 33–42), it may be suggested that the positive actions of MIBG on vascular remodelling reflect its combined action on both cell differentiation and cell proliferation.

While the preferred embodiments of the invention have been described above, it will be recognized and understood that various modifications may be made therein, and the appended claims are intended to cover all such modifications which may fall within the spirit and scope of the invention.

What is claimed is:

1. A method of inhibiting restenosis comprising:

applying an effective amount of a pharmaceutical composition comprising meta-iodobenzylguanidine (MIBG) and a pharmaceutically acceptable excipient to a damaged vessel.

2. The method according to claim 1, wherein said composition inhibits smooth muscle cell differentiation, migration and proliferation.

3. The method according to claim 1, wherein said composition further comprises an adhesive agent.

4. The method according to claim 3, wherein said adhesive agent is biodegradable.

5. The method according to claim 4, wherein said adhesive agent is fibrin glue.

6. The method according to claim 1, wherein said composition is coated on a vascular stent.

* * * * *